(12) United States Patent
Kellar et al.

(10) Patent No.: US 12,303,405 B2
(45) Date of Patent: May 20, 2025

(54) KNEE ARTHROPLASTY METHOD

(71) Applicant: Little Engine, LLC, Belmont, NC (US)

(72) Inventors: Franz W. Kellar, Gastonia, NC (US); Harold L. Crowder, Concord, NC (US); Franz Austen Kellar, Gastonia, NC (US)

(73) Assignee: Dynamic Balancer Systems LLC, Belmont, NC (US)

( * ) Notice: Subject to any disclaimer, the term of this patent is extended or adjusted under 35 U.S.C. 154(b) by 0 days.

(21) Appl. No.: 18/933,463

(22) Filed: Oct. 31, 2024

(65) Prior Publication Data

US 2025/0134678 A1 May 1, 2025

Related U.S. Application Data

(60) Provisional application No. 63/595,238, filed on Nov. 1, 2023.

(51) Int. Cl.
*A61F 2/46* (2006.01)
*A61B 90/00* (2016.01)
*A61B 17/02* (2006.01)

(52) U.S. Cl.
CPC .............. *A61F 2/461* (2013.01); *A61B 90/39* (2016.02); *A61B 2017/0268* (2013.01);
(Continued)

(58) Field of Classification Search
CPC ........... A61B 17/025; A61B 2017/0268; A61F 2/461
See application file for complete search history.

(56) References Cited

U.S. PATENT DOCUMENTS

| | | | |
|---|---|---|---|
| 4,124,026 | A | 11/1978 | Berner et al. |
| 5,713,897 | A | 2/1998 | Goble et al. |

(Continued)

FOREIGN PATENT DOCUMENTS

| | | |
|---|---|---|
| WO | 2014188184 | 11/2014 |
| WO | 2017195046 | 11/2017 |

OTHER PUBLICATIONS

Attune Knee System, CAS Surgical Technique, Published 2014, accessed at "http://synthes.vo.Ilnwd.net/o16/LLNWMB8/US%20Mobile/Synthes%20North%20America/Product%20Support%20Materials/Technique%20Guides/DSUS-JRC-0514-0141%20ATTUNE_CAS_ST.pdf".

(Continued)

*Primary Examiner* — Andrew Yang
(74) *Attorney, Agent, or Firm* — Shumaker, Loop & Kendrick, LLP; Jonathan M. Hines

(57) ABSTRACT

A method of evaluating a knee joint including a femur, a tibia, and ligaments, includes: inserting into the joint a tensioner-balancer; moving the joint while using the tensioner-balancer to maintain predetermined distraction force or distraction height, and collecting height and force data; deriving ligament displacement data and load data from the height and distraction data; processing the data into a digital model of the joint, including a characterization curve for a plurality of flexion angles; importing into the model implant geometry having femoral and tibial components, each having a back surface; updating the model with a location of femoral and tibial cuts, positioned such that when the components are placed in the joint with their back surfaces against the respective cuts, the implant will position the joint to function in a selected portion of the curve; and storing the model.

30 Claims, 42 Drawing Sheets

(52) U.S. Cl.
CPC .................. *A61B 2090/3916* (2016.02); *A61F 2002/4633* (2013.01); *A61F 2002/4666* (2013.01)

(56) References Cited

U.S. PATENT DOCUMENTS

| | | | |
|---|---|---|---|
| 5,935,129 | A | 8/1999 | McDevitt et al. |
| 6,022,377 | A | 2/2000 | Nuelle et al. |
| 6,080,154 | A | 6/2000 | Reay-Young et al. |
| 6,162,234 | A | 12/2000 | Freedland et al. |
| 6,205,411 | B1 | 3/2001 | DiGioia, III et al. |
| 6,859,661 | B2 * | 2/2005 | Tuke .................. A61B 90/36 606/130 |
| 7,070,598 | B2 | 7/2006 | Lim et al. |
| 7,849,751 | B2 | 12/2010 | Clark et al. |
| 10,076,377 | B2 | 9/2018 | Bonutti et al. |
| 10,405,849 | B1 | 9/2019 | Cole et al. |
| 10,478,171 | B1 | 11/2019 | Cole et al. |
| 10,555,729 | B1 | 2/2020 | Cole et al. |
| 11,602,443 | B1 | 3/2023 | Cole et al. |
| 11,642,148 | B2 | 5/2023 | Ujihira |
| 2001/0008971 | A1 | 7/2001 | Schwartz et al. |
| 2003/0032983 | A1 | 2/2003 | Bonutti et al. |
| 2004/0064191 | A1 | 4/2004 | Wasielewski |
| 2005/0222488 | A1 | 10/2005 | Chang et al. |
| 2005/0267485 | A1 | 12/2005 | Cordes et al. |
| 2008/0051798 | A1 | 2/2008 | Colquhoun et al. |
| 2008/0114367 | A1 | 5/2008 | Meyer |
| 2008/0288060 | A1 | 11/2008 | Kaye et al. |
| 2010/0007140 | A1 | 1/2010 | Duquette et al. |
| 2010/0249659 | A1 | 9/2010 | Sherman et al. |
| 2010/0250571 | A1 | 9/2010 | Pierce et al. |
| 2010/0256612 | A1 | 10/2010 | Dell'Oca |
| 2011/0093081 | A1 | 4/2011 | Chana et al. |
| 2012/0095515 | A1 | 4/2012 | Hamilton |
| 2013/0102929 | A1 | 4/2013 | Haight et al. |
| 2013/0131737 | A1 | 5/2013 | Cheng et al. |
| 2013/0226189 | A1 | 8/2013 | Young |
| 2013/0261502 | A1 * | 10/2013 | Sherman ............... A61F 2/4657 600/587 |
| 2014/0025081 | A1 | 1/2014 | Lorio et al. |
| 2014/0094715 | A1 | 4/2014 | Stein et al. |
| 2014/0194907 | A1 | 7/2014 | Bonutti et al. |
| 2014/0257381 | A1 | 9/2014 | Palese |
| 2014/0277526 | A1 | 9/2014 | Stein et al. |
| 2014/0296979 | A1 | 10/2014 | Delfosse et al. |
| 2015/0105782 | A1 | 4/2015 | D'Lima et al. |
| 2016/0007909 | A1 | 1/2016 | Singh et al. |
| 2016/0030156 | A1 | 2/2016 | Cole |
| 2016/0106409 | A1 | 4/2016 | Moholkar |
| 2016/0278754 | A1 * | 9/2016 | Todorov .................. A61B 90/06 |
| 2016/0278944 | A1 | 9/2016 | D'Lima et al. |
| 2016/0338751 | A1 | 11/2016 | Kellar et al. |
| 2017/0035409 | A1 | 2/2017 | Fallin et al. |
| 2017/0065438 | A1 | 3/2017 | Burnikel |
| 2017/0172624 | A1 | 6/2017 | Brunner et al. |
| 2017/0312099 | A1 | 11/2017 | Paszicsnyek |
| 2018/0049622 | A1 | 2/2018 | Ryan et al. |
| 2018/0116278 | A1 | 5/2018 | Lang |
| 2018/0153599 | A1 | 6/2018 | Daly et al. |
| 2018/0177612 | A1 | 6/2018 | Masei et al. |
| 2018/0185100 | A1 | 7/2018 | Weinstein et al. |
| 2018/0199952 | A1 | 7/2018 | Cole |
| 2018/0296232 | A1 | 10/2018 | Nielsen et al. |
| 2019/0076273 | A1 | 3/2019 | Goodchild et al. |
| 2019/0167447 | A1 | 6/2019 | Angibaud |
| 2019/0183554 | A1 | 6/2019 | Pedicini |
| 2019/0358056 | A1 | 11/2019 | Lerat et al. |
| 2020/0155135 | A1 | 5/2020 | Cole et al. |
| 2020/0237441 | A1 | 7/2020 | Zuhars et al. |
| 2023/0390073 | A1 | 12/2023 | Kellar et al. |
| 2023/0390080 | A1 | 12/2023 | Cole et al. |

OTHER PUBLICATIONS

Bathis et al., "Flexion Gap Configuration in Total Knee Arthroplasty Following Hight Tibial Osteotomy", published online Sep. 30, 2004, International Orthopaedics (SICOT) 28: 366-369.

M. J. Winemaker, MD, FRCS (C), "Perfect Balance in Total Knee Arthroplasty, The Elusive Compromise", The Journal of Arthroplasty vol. 17. No. 1 2002, 2002, Churchill Livingstone, Canada.

International Search Report and Written Opinion from the International Searching Authority for International Patent Application No. PCT/US2019/061668 on Jan. 14, 2020.

International Search Report and Written Opinion from the International Searching Authority for International Patent Application No. PCT/US2021/018545 on May 6, 2021.

International Search Report and Written Opinion from the International Searching Authority for International Patent Application No. PCT/US2021/031961 on Sep. 10, 2021.

* cited by examiner

Lateral Collateral Ligament Cross Section

Medial Collateral Ligament Cross Section

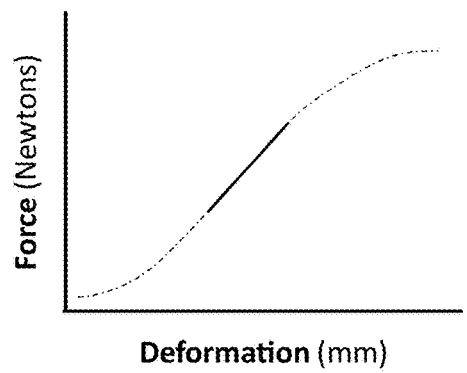
Fig. 40
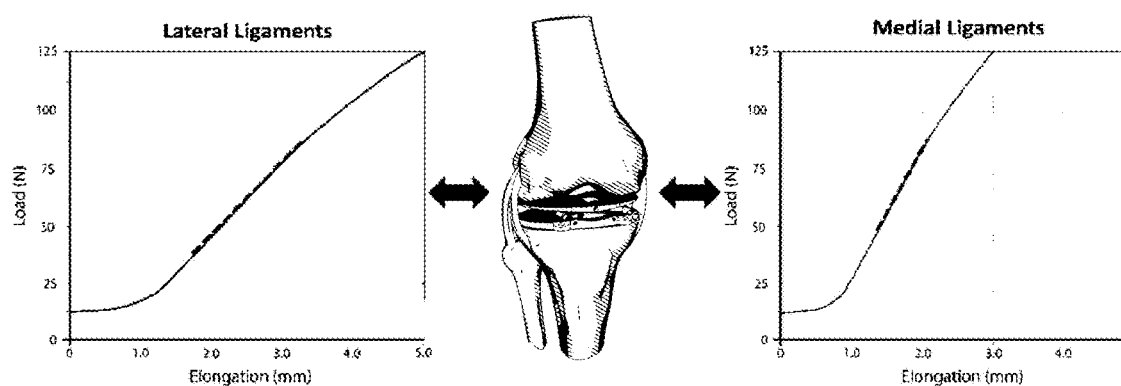
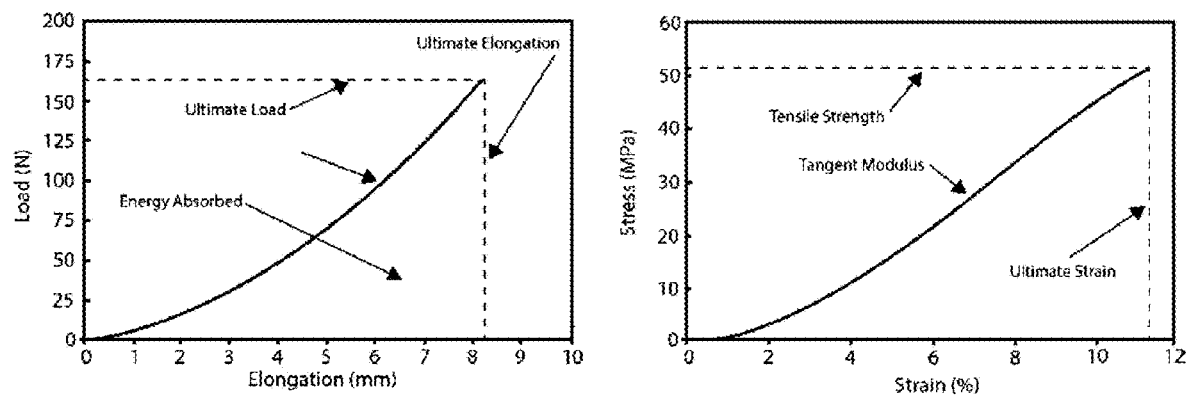

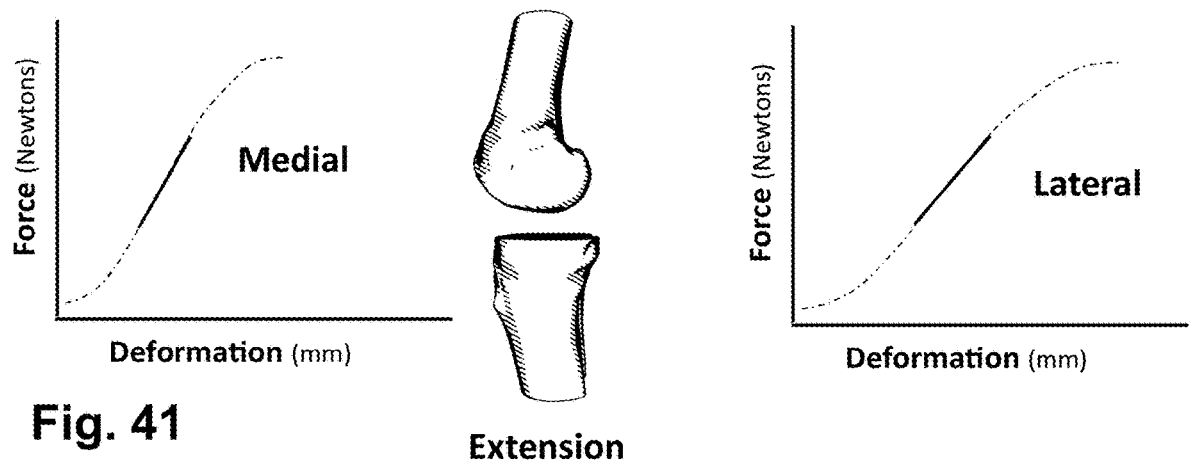
Fig. 41  Extension
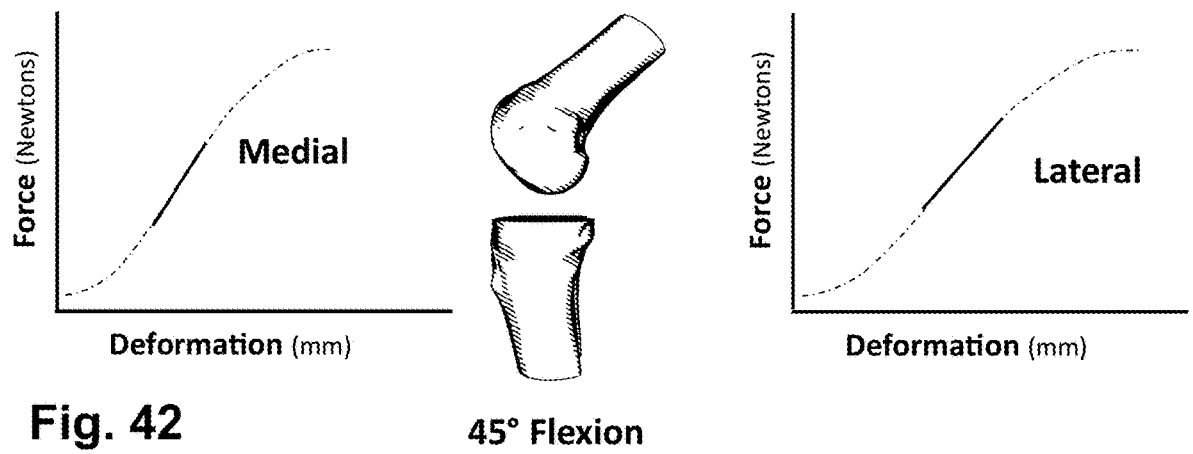
Fig. 42  45° Flexion
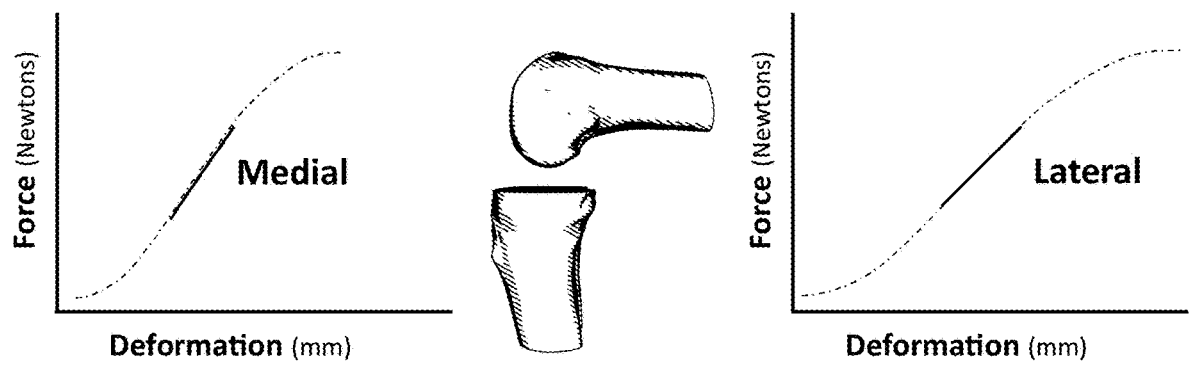
Fig. 43  90° Flexion

KNEE ARTHROPLASTY METHOD

BACKGROUND

This invention relates generally to medical devices and instruments, and more particularly to methods for soft tissue evaluation.

Total knee arthroplasty ("TKA") is a procedure for treating an injured, diseased, or worn human knee joint. In a TKA, an endoprosthetic joint is implanted, replacing the bearing surfaces of the joint with artificial members. Proper alignment of the joint and substantially equal tension in the soft tissues surrounding the joint are important factors in producing a good surgical outcome.

A human knee joint "J" is shown in FIGS. 1-4. The joint J is prepared for implantation by cutting away portions of the femur "F" and the tibia "T". FIGS. 1 and 2 show the joint in extension, with cutting planes for a tibial cut 1 and a distal femoral cut 2. The tibial cut 1 and the distal femoral cut 2 cooperate to define an extension gap "EG". FIGS. 3 and 4 show the joint J in flexion, with a cutting plane 3 shown for a posterior cut. The tibial cut 1 and the posterior cut 3 cooperate to define a flexion gap "FG".

FIG. 5 depicts an exemplary endoprosthetic 10 (i.e., implant) of a known type. The endoprosthetic 10 includes a tibial component 12 and a femoral component 14. The tibial component 12 is made up of a tibial tray 16 and an insert 18. The insert 18 has a back surface 20 which abuts the tibial tray 16 and an opposed articular surface 22. The tray includes a prominent keel 24 protruding in the inferior direction (i.e. down a longitudinal axis of the tibia). The tibial tray 16 may be made from a hard, wear-resistant material such as a biocompatible metal alloy. The insert 18 may be made from a low-friction material such as a biocompatible plastic.

The femoral component 14 includes a back surface 28 shaped to abut a surface of the femur F that has been appropriately shaped and an articular surface 30 comprising medial and lateral contact surfaces 32 and 34, respectively. The femoral component 14 may be made from a hard, wear-resistant material such as a biocompatible metal alloy.

The back surface 28 includes multiple faces collectively defining a rough "U" or "J" shape. The back surface 28 includes protruding locator pins 36.

The tibial tray 16 is implanted into the tibia T and the femoral component 14 is implanted into the femur F. The insert 18 is placed into the tibial tray 16. The articular surface 22 of the insert 18 bears against the articular surface 30 of the femoral component 14, defining a functional joint.

In the illustrated example, the endoprosthesis 10 is of the cruciate-retaining ("CR") type. It includes a cutout or notch 38 in the posterior aspect of the tibial component 12 which provides a space for the posterior cruciate ligament ("PCL").

At the discretion of the surgeon, various types of tibial component 12 may be used in conjunction with a given femoral component 14, thereby providing different postoperative knee characteristics. For example, this may be accomplished by providing different tibial inserts 18 to be placed into the tibial tray 16. Examples of these tibial components are shown in FIGS. 6-11. FIGS. 6 and 7 show lateral and medial aspects, respectively, of a constrained-type tibial component 13. FIGS. 8 and 9 show lateral and medial aspects, respectively, of a medial pivot type tibial component 15. FIGS. 10 and 11 show lateral and medial aspects, respectively, of a posterior-stabilized tibial component 17. In this type, a post 19 protrudes from the articular surface between the condyles.

A goal of total knee arthroplasty is to obtain symmetric and balanced flexion and extension gaps FG, EG (in other words, two congruent rectangles). These gaps are generally measured in millimeters of separation, are further characterized by a *varus* or valgus angle measured in degrees, and are measured after the tibia cut, distal femoral cut, and posterior femoral cut have been done (to create flat surfaces from which to measure). It follows that, to achieve this balance, the ligament tension in the lateral and medial ligaments would be substantially equal on each side or have a surgeon-selected relationship, and in each position.

One problem with prior art arthroplasty techniques is that it is difficult and complex to achieve the proper balance. Current state-of-the-art gap balancing devices do not enable balancing with the patella in-place and are large, overly-complicated devices that work only with their respective knee implant systems.

BRIEF SUMMARY OF THE INVENTION

The above-noted problems are addressed by a method for knee arthroplasty using an instrumented tensioner-balancer to measure bone and soft tissue parameters of a joint.

According to one aspect of the technology described herein, a method is described of evaluating a human knee joint which includes a femur bone, a tibia bone, and ligaments, wherein the ligaments are under anatomical tension to connect the bones together. The method includes: inserting into the knee joint a tensioner-balancer that includes: a femoral interface surface and a tibial interface surface; and a means of applying a distraction force to the knee joint; moving the knee joint through at least a portion of its range of motion; while moving the knee joint, using the tensioner-balancer to maintain a predetermined distraction force or a predetermined distraction height, and collecting distraction height data and distraction force data of the femur bone relative to the tibia bone from at least one sensor; deriving ligament displacement data and load data from the distraction height data and distraction force data of the femur bone relative to the tibia bone; processing the collected data to produce a digital geometric model of the knee joint, wherein the model includes a ligament force versus ligament displacement characterization curve for each of a plurality of flexion angles of the femur bone relative to the tibia bone; selecting a portion of the characterization curve that represents a specific level of ligament tautness desired; importing into the digital geometric model an implant geometry having a femoral component and a tibial component, each of the components having an articular surface and an opposed back surface; updating the digital geometric model by computing a location of a femoral bone cut and a tibial bone cut, the cuts being positioned such that when the components are placed in the joint with their articular surfaces in contact with each other and their back surfaces against the respective bone cuts, the implant will position the knee joint to function in the selected portion of the characterization curve; and storing the digital geometric model for further use.

BRIEF DESCRIPTION OF THE DRAWINGS

The invention may be best understood by reference to the following description taken in conjunction with the accompanying drawing figures in which:

FIG. 40 is a group of charts showing measured force vs. deformation in the medial and lateral soft tissue complexes of a knee joint, and the related stress vs. strain;

FIG. 41 is a diagram showing measured force vs. deformation in the medial and lateral soft tissue complexes of a knee joint, in an extended position;

FIG. 42 is a diagram showing measured force vs. deformation in the medial and lateral soft tissue complexes of a knee joint, in a 45 degree flexed position;

FIG. 43 is a diagram showing measured force vs. deformation in the medial and lateral soft tissue complexes of a knee joint, in a 90 degree flexed position;

DETAILED DESCRIPTION OF THE INVENTION

Figure 12:
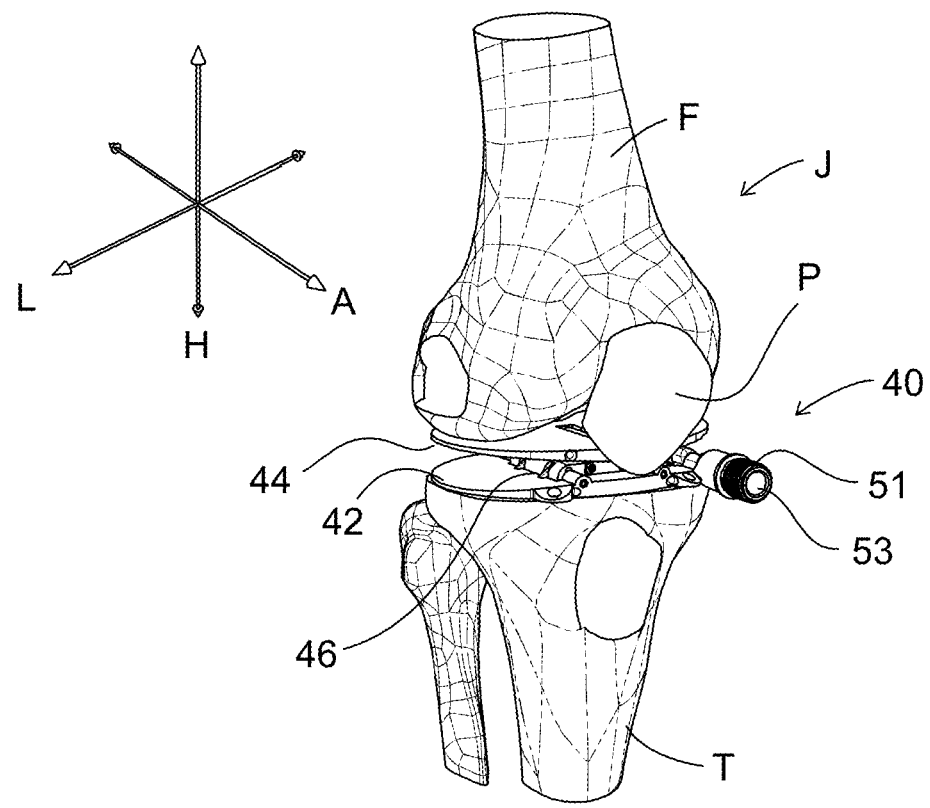
FIG. 12 is a perspective view of a human knee joint in an extended position, with a tensioner-balancer inserted therein.
Figure 13:
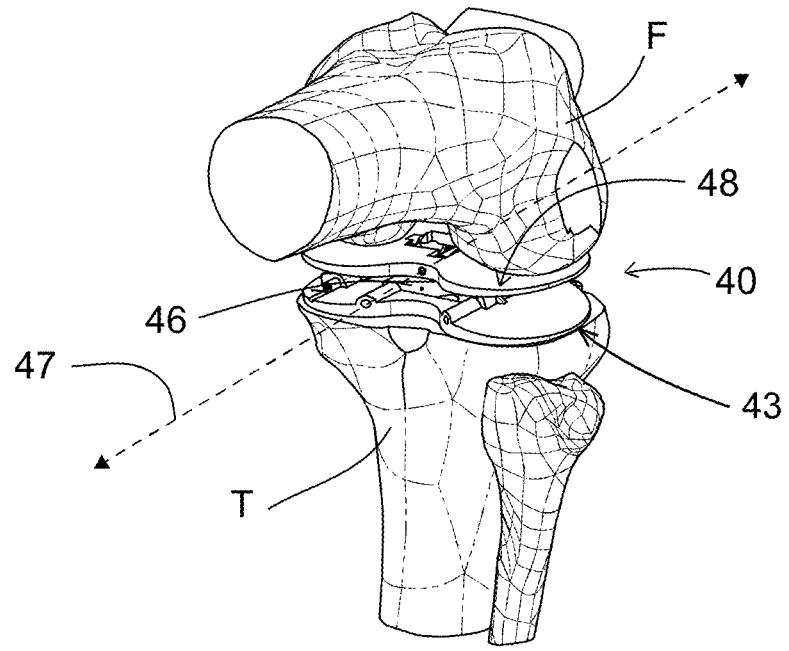
FIG. 13 is a view of the knee joint and tensioner-balancer of FIG. 12, in a flexed position.

Now, referring to the drawings wherein identical reference numerals denote the same elements throughout the various views, FIGS. 12 and 13 depict an exemplary embodiment of a tensioner-balancer 40 (alternatively referred to in various embodiments as a gap balancer, distractor, distractor-tensioner, or jack) which is useful for balancing a gap in a human knee joint as part of a total knee arthroplasty and for other therapeutic procedures.

Solely for purposes of convenient description, the tensioner-balancer 40 may be described as having a length extending along a lateral-to-medial direction "L", a width extending along an axial direction "A", and a height extending along a vertical direction "H", wherein the lateral direction, the axial direction, and the vertical direction are three mutually perpendicular directions. These directional terms, and similar terms such as "top", "bottom", "upper", "lower" are used merely for convenience in description and do not require a particular orientation of the structures described thereby.

In one aspect, the tensioner-balancer 40 may be described as having the ability to control the movement of one degree of freedom (e.g., translation along H) and measure the movement of a second degree of freedom (rotation about A) while constraining or fixing the remaining four degrees of freedom (translation along A and L; rotation about H and L).

The tensioner-balancer 40 comprises a baseplate 42 and a top plate 44 interconnected by a linkage 46. The linkage 46 and the tensioner-balancer 40 are movable between a retracted position in which the top plate 44 lies close to or against the baseplate 42, and an extended position in which the top plate 44 is spaced away from the baseplate 42. As described in more detail below, a means is provided to actuate the linkage 46 in response to an actuating force in order to separate the baseplate 42 and the top plate 44 in a controllable manner. This separation enables it to extend so as to apply a load to a knee joint. While the illustrated tensioner-balancer 40 includes a mechanically-operated linkage 46, it will be understood that this is just one operative example of a "distracting mechanism" operable to move the tensioner-balancer between retracted and extended positions. It is envisioned that the mechanical linkage could be replaced with other types of mechanical elements, or electrical, pneumatic, or hydraulic devices.

The top plate 44 includes a femoral interface surface 48 and is mounted to the linkage 46 in such a manner that it can freely pivot about pivot axis 47 (an axis corresponding to a *varus*/valgus angulation of the knee).

The baseplate 42 includes a tibial interface surface 43. The baseplate 42 includes a tensioner-balancer coupler 51 having a first interface 53. In the illustrated example, the first interface 53 is configured as a mechanical coupling. The coupler 51 is interconnected to the linkage such that an actuating force applied to the coupler 51, such as a torque, actuates the linkage 46. A drive shaft (not shown) passes through this coupler and connects with the linkage.

Optionally, the tensioner-balancer 40 may incorporate means for measuring a force input. For example, the coupler 51 may incorporate a sensor (not shown) such as a strain gage operable to produce a signal representative of the torque applied to the coupler 51.

As a further option, the tensioner-balancer 40 may incorporate a separate measuring linkage (not shown) connected to the top plate and arranged to follow the movement of the top plate 44. The measuring linkage would be connected to a crank which would be in turn connected to an indicating shaft coaxial to the coupler. The measuring linkage may be arranged such that pivoting movement of the top plate results in rotation of the indicating shaft. The movement of the indicating shaft may be observed visually, or it may be detected by a sensor such as an RVDT or rotary encoder or resolver, which may be part of an instrument described below. This permits measurement of plate angle and/or vertical position.

The tensioner-balancer may be supplied with an appropriate combination of transducers to detect physical properties such as force, tilt angle, and/or applied load and generate a signal representative thereof. For example, the tensioner-balancer may be provided with sensors operable to detect the magnitude of extension (i.e. "gap height"), the angle of the top plate about the pivot axis 47 (i.e. *varus*/valgus), and/or the applied force in the extension direction. Nonlimiting examples of suitable transducers include strain gages, load cells, linear variable differential transformers ("LVDT"), rotary variable differential transformers ("RVDT"), or linear or rotary encoders or resolvers, or 6 DOF sensors showing relative motion.

Figure 14:
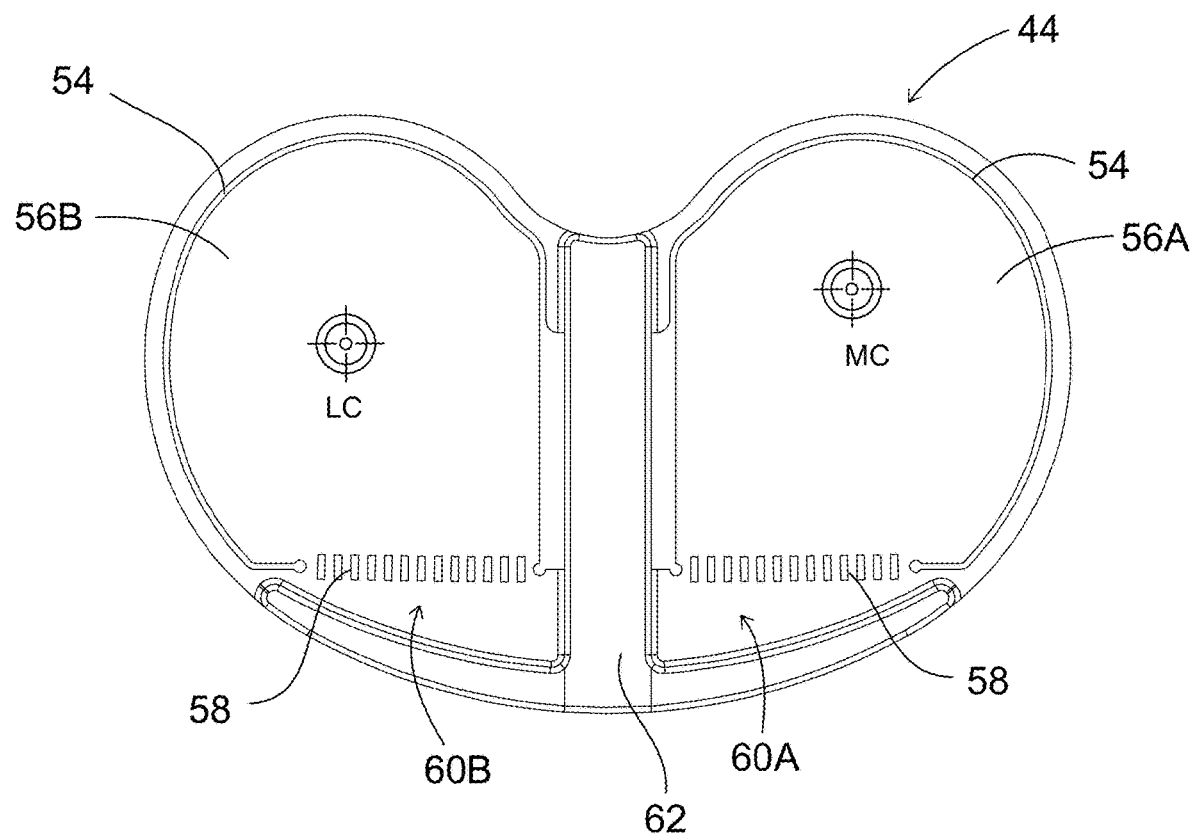
FIG. 14 is a top plan view of a top plate of the tensioner-balancer of FIG. 12.
Figure 15:
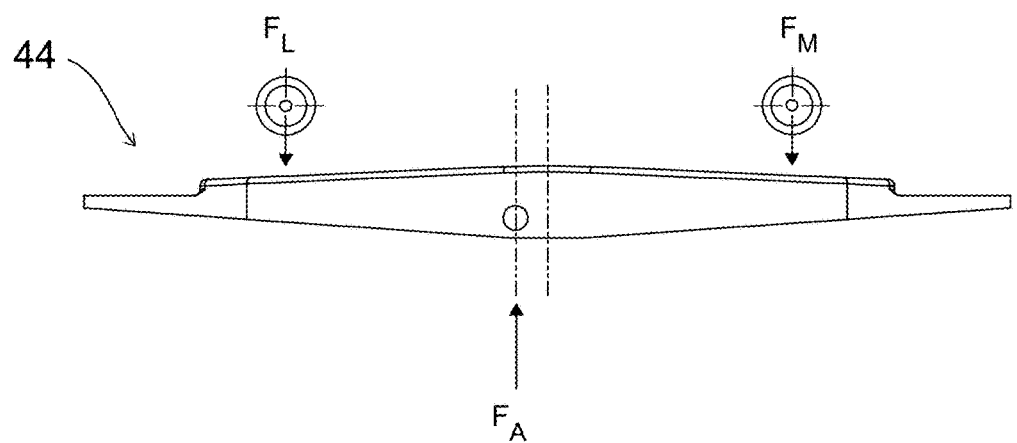
FIG. 15 is a front elevation view of the top plate of FIG. 12.

FIGS. 14 and 15 illustrate an exemplary configuration in which the top plate 44 includes grooves 54 which define medial and lateral cantilevered pads 56A, 56B respectively. One or more strain gages 58 are mounted to the top plate 44 in a first left-right row 60A at the intersection between the medial pad 56A and the forward portion 62 of the top plate 44. One or more strain gages 58 are mounted to the top plate 44 in a second fore-aft row 60B at the intersection between the lateral pad 56B and the forward portion 62 of the top plate 44.

Figure 16:
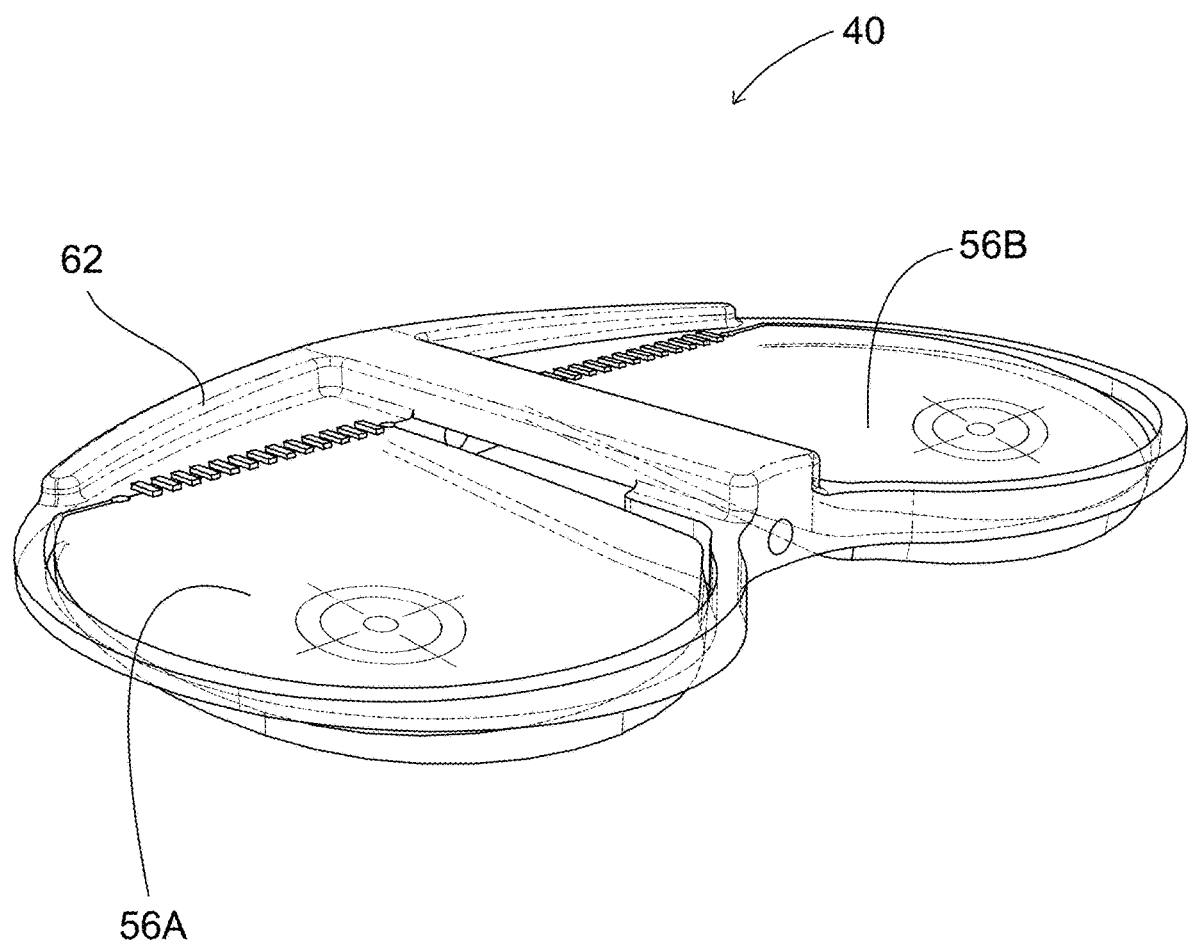
FIG. 16 is a perspective view of the top plate of FIG. 12, in a deflected position.

FIG. 16 shows the medial and lateral cantilevered pads 56A, 56B in a deflected position under load. The magnitude of deflection is greatly exaggerated for illustrative purposes.

Referring to FIG. 14, when the knee joint is articulated it is possible to identify an instantaneous point of peak contact pressure. There is one such point for each of the condyles. These positions are mapped onto the medial and lateral cantilevered pads 56A, 56B and labeled "MC" (standing for "medial load center") and "LC" (standing for "lateral load center").

Figure 17:
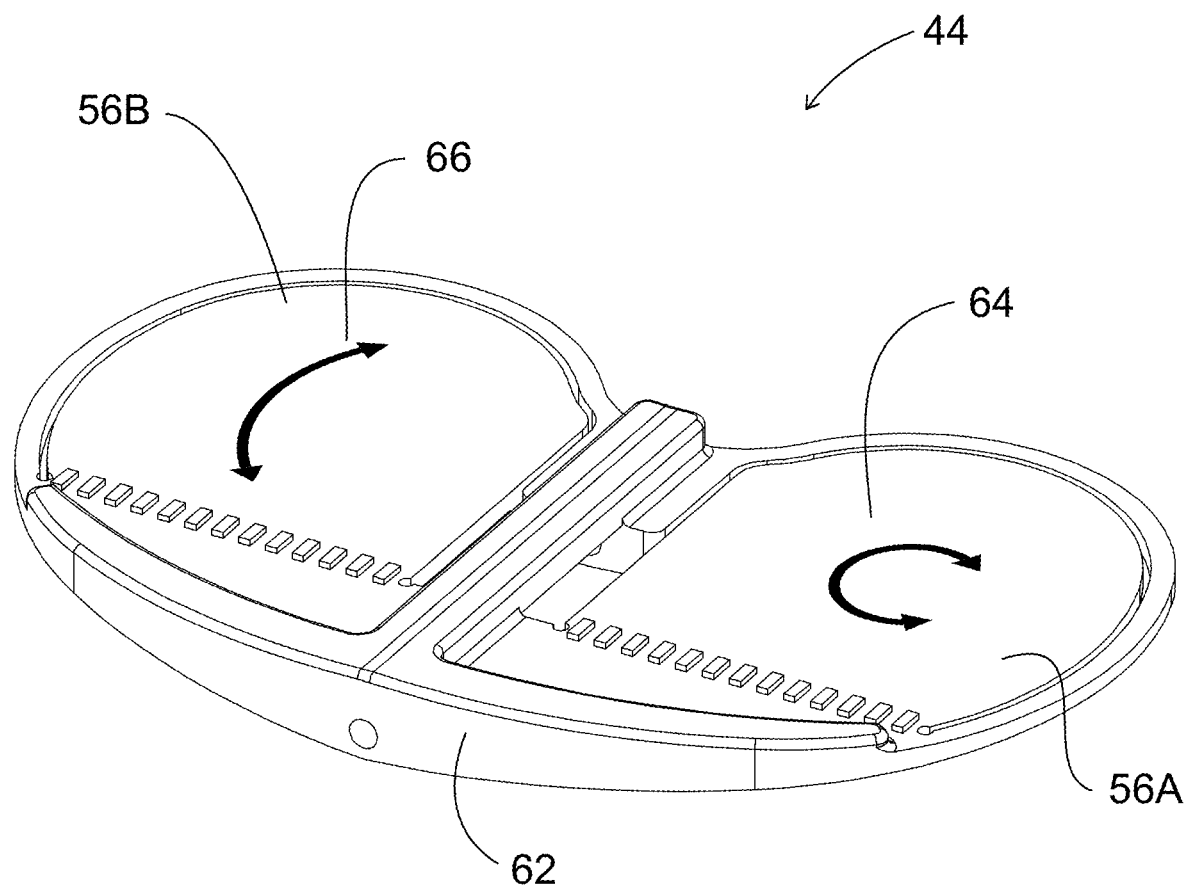
FIG. 17 is a perspective view of the top plate of FIG. 12, showing movement of contact points superimposed thereon.

Analysis by the inventors has shown that using the depicted configuration, with one or more strain gauges provided for each of the cantilevered pads 56A, 56B, it is possible to resolve the position of the load centers LC, MC in two axes. Stated another way, using this hardware, it is possible to identify the instantaneous lateral-medial and anterior-posterior position of the load centers LC, MC. More complex sensors may permit the resolution in two axes using one or more strain gages for each cantilevered pad. Referring to FIG. 17, and as will be described further below, this enables the ability of the tensioner-balancer 40 to track certain relative movements of the femur F. One of these is referred to as "medial pivot" shown by arrow 64 and the other is referred to as "rollback", shown by arrow 66.

Figure 18:
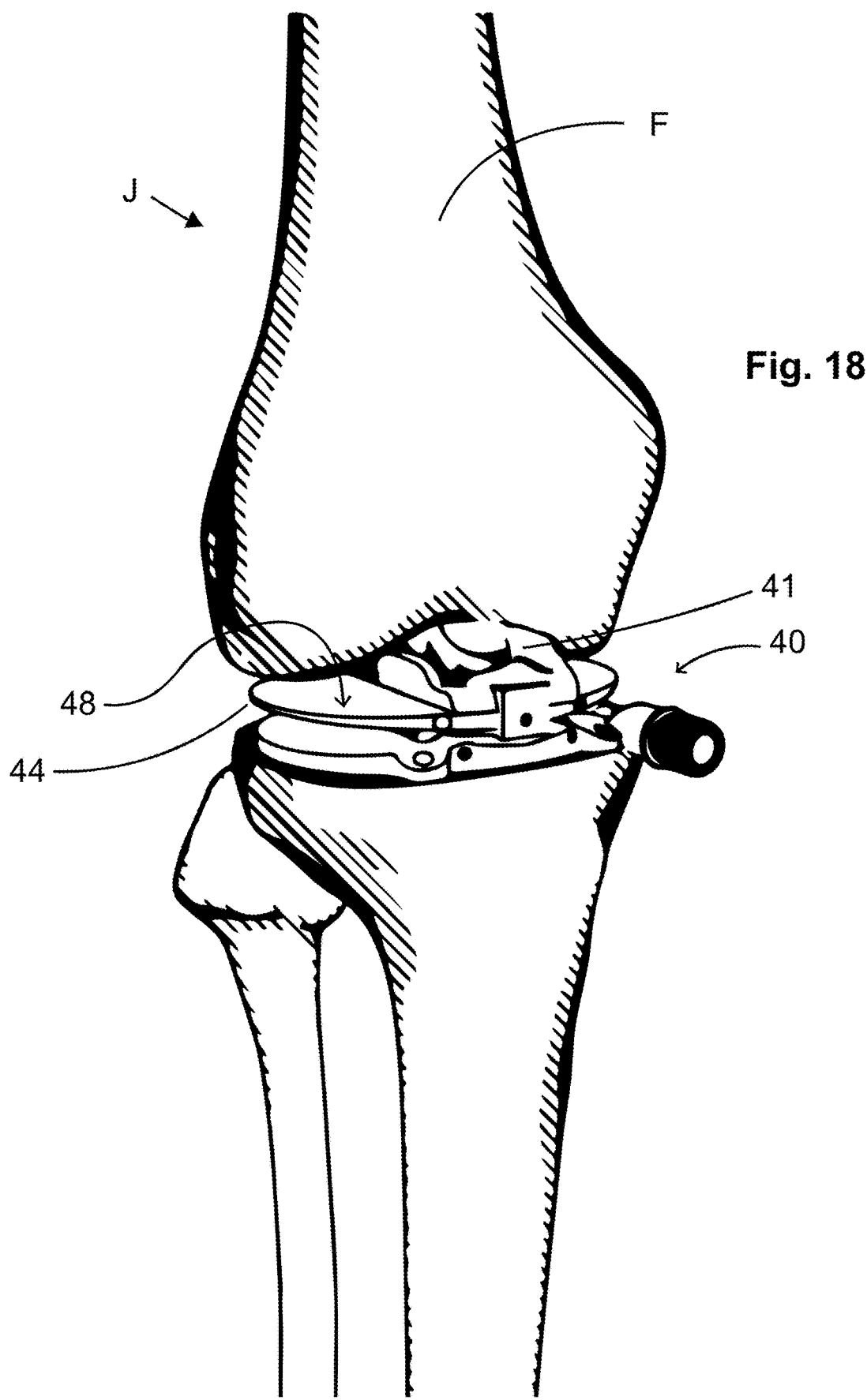
FIG. 18 is a perspective view of a human knee joint with a modified version of a tensioner-balancer inserted therein.

Optionally, the tensioner-balancer 40 may be modified to provide additional stability and accuracy when measuring the knee joint J. FIG. 18 illustrates a tensioner-balancer 40 inserted into a knee joint J. A clip 41 is attached to the femoral interface surface 48 of the top plate 44. It may be secured such that it does not move relative to the top plate 44. The clip 41 has a convex shape which is generally sized and shaped to fit into the trochlear groove of the femur F. The interface of the convex shape and the trochlear groove provides assurance that the tensioner-balancer 40 will remain centered while positioned in the joint J.

Figure 19:
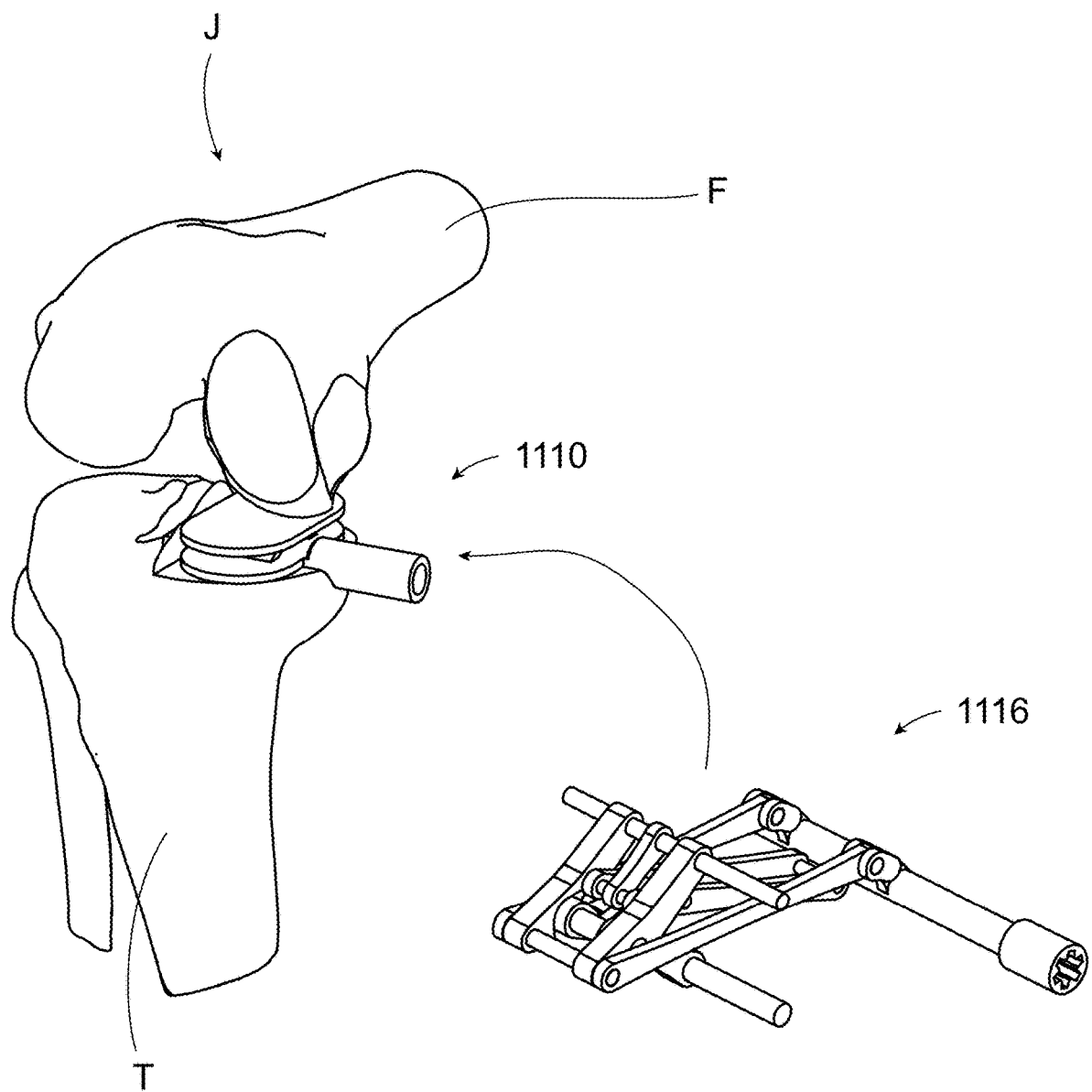
FIG. 19 is a perspective view of a human knee joint with a uni-compartmental tensioner-balancer inserted therein.

In some surgical procedures, the arthroplasty may be uni-compartmental, i.e., only involving the medial or lateral compartment of the joint J. In that case, one smaller-scale tensioner-balancer 1110 (FIG. 19) may be used for either the medial or lateral compartment. Optionally, by suitable orientation of its operating linkage 1116 the tensioner-balancer 1110 may be configured to permit approach of an instrument (not shown) from the medial or lateral aspect of the joint J as opposed to the anterior aspect.

Figure 20:
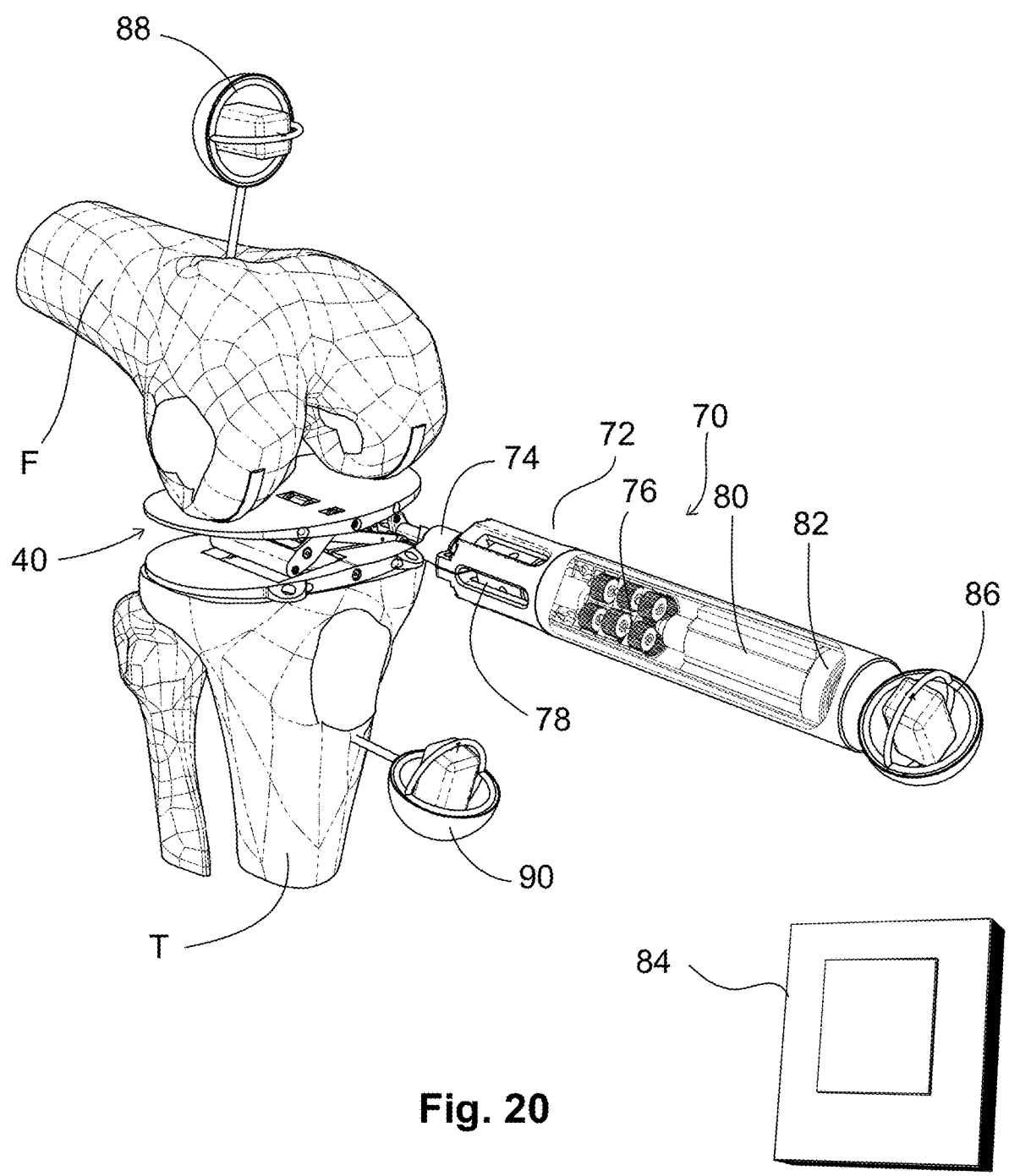
FIG. 20 is a perspective view of a human knee joint with a tensioner-balancer inserted therein and coupled to a instrument.

FIG. 20 illustrates an exemplary actuating instrument 70 for use with the tensioner-balancer 40. The actuating instrument 70 includes a barrel 72 with an instrument coupler 74 at its distal end defining a second interface (hidden in this view) which is complementary to the first interface 53 of the tensioner-balancer 40. The interior of barrel 72 includes an appropriate internal mechanism to apply torque to the instrument coupler 74, through a shaft 78, such as a servo or stepper motor 80 with related control electronics including a rotary encoder coupled to a planetary gearset 76 that interconnects the servo motor 80 and shaft 78.

The internal mechanism is operable to apply an actuating load to the tensioner-balancer 40. The actuating instrument 70 includes an electronic data transceiver, shown schematically at 82. The transceiver 82 may operate over a wired or wireless connection. The actuating instrument 70 may be supplied with an appropriate combination of transducers (not shown in FIG. 20) to detect physical properties such as force, tilt angle, and/or applied load and generate a signal representative thereof. For example, the tensioner-balancer 40 may be provided with sensors operable to detect the magnitude of extension (i.e. "gap height"), the angle of the top plate about the pivot axis (i.e. *varus*/valgus), and/or the applied force in the extension direction. Nonlimiting examples of suitable transducers include strain gages, load cells, linear variable differential transformers ("LVDT"), rotary variable differential transformers ("RVDT"), or linear or rotary encoders or resolvers.

Displacement of the tensioner-balancer 40 may be derived from the encoder signals, knowing the kinematics of the linkage 46. The transceiver 82 is operable to transmit the signal.

A remote display 84 is configured to receive the signal and produce a display of the transducer data. As one example, the remote display 84 may be embodied in a conventional portable electronic device such as a "smart phone" or electronic tablet with suitable software programming. Optionally, the remote display 84 or other suitable transmitting device may be used to send remote operation commands to the actuating instrument 70.

In use, the remote display 84 permits the surgeon to observe the physical properties of the tensioner-balancer 40 in real time as the actuating instrument 70 is used to operate the tensioner-balancer 40.

Optionally, the actuating instrument 70 may incorporate a tracking marker 86. The tracking marker 86 is operable such that, using an appropriate receiving device, the position and orientation of the receiving device relative to the tracking marker 86 may be determined by receipt and analysis at the receiving device of signals transmitted by the tracking marker 86.

As illustrated, the tracking marker 86 may be configured as an inertial navigation device including one or more accelerometers and gyroscopic elements capable of providing angular rate information and acceleration data in 3D space.

In an alternative embodiment which is not illustrated, the tracking marker may include one or more tracking points which may be configured as transmitting antennas, radiological markers, or other similar devices.

Six degree-of-freedom, local NAV, non-line-of sight, tracking markers 86 and appropriate receivers are known within the state-of-the-art.

A tracking marker 88 would be attached to the femur F in such a way that it has a substantially fixed position and orientation relative to the femur F. For example, a tracking marker 88 may be attached directly to the femur F.

In addition to the femur-mounted tracking marker 88, at least one additional tracking marker is provided which has a substantially fixed position and orientation relative to the tibia T. Where the actuating instrument 70 is rigidly coupled to the tensioner-balancer 40, the tibial tracking function may be provided by the tracking marker 86 of the actuating instrument 70. Alternatively, a tracking marker 90 may be attached directly to the tibia T.

The apparatus described above is suitable for various surgical procedures.

In one procedure, the tensioner-balancer 40 is used to evaluate the knee and to model and digitize the articular surfaces of the knee over its range of motion.

More particularly, the locus of points of contact of the femur F and the top plate 44 are modeled as a medial spline and a lateral spline.

To carry out this modeling, the tensioner-balancer is inserted between the femur F and the tibia T. In the example shown in FIG. 20, this is accomplished after having first made the tibial plateau cut. However, the tibial plateau cut is not mandatory. For example, a relatively thin tensioner-balancer (not shown) using means other than a mechanical linkage 46 for distraction could be used. For example, hydraulic or pneumatic means could be used to provide distraction force.

The actuating instrument 70 is coupled to the tensioner-balancer 40. Femoral tracking marker 88 is implanted to the femur F. At least one of a tibial tracking marker 90 and an instrument tracking marker 86 is placed.

The tensioner-balancer 40 is extended to apply a load to the knee joint. While different modes of operation are possible, one exemplary mode is to extend the tensioner-balancer 40 until a predetermined distraction load is applied. Feedback control or mechanical spring preload may then be used to maintain this distraction load, while the top plate 44 is permitted to pivot freely and translate vertically while the degrees of pivot and vertical displacement are measured, tracked, and recorded by the feedback control hardware and software. One example of a suitable distraction load is approximately 130 N (30 lb.) to 220 N (50 lb.). Another exemplary mode is to extend the tensioner-balancer 40 until a predetermined distraction distance is applied. Feedback control may then be used to maintain this distraction distance, while the top plate 44 is permitted to pivot freely and while the degrees of pivot and distraction load are measured, tracked, and recorded by the feedback control hardware and software.

Figure 21:
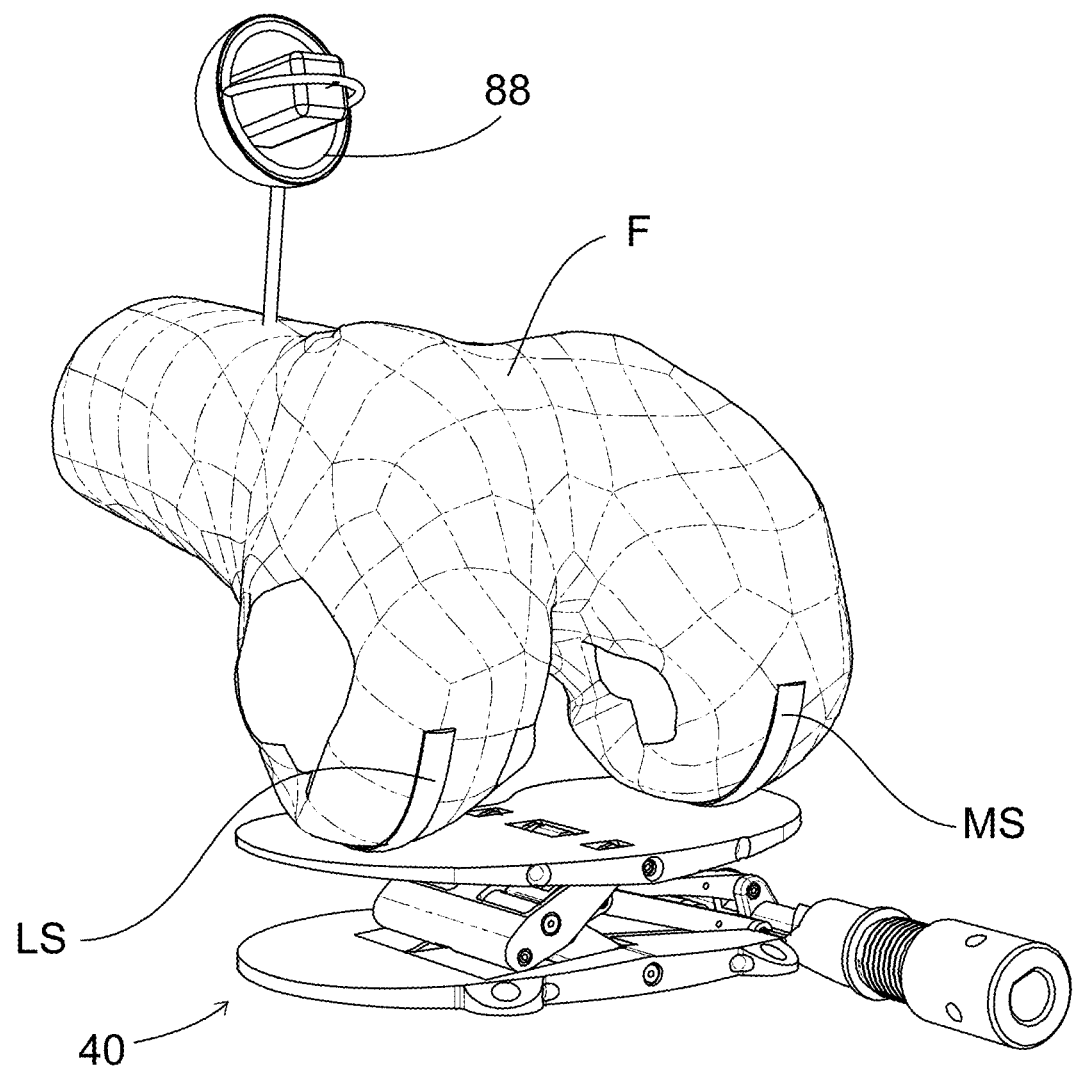
FIG. 21 is a perspective view showing a femur in contact with a tensioner-balancer.
Figure 22:
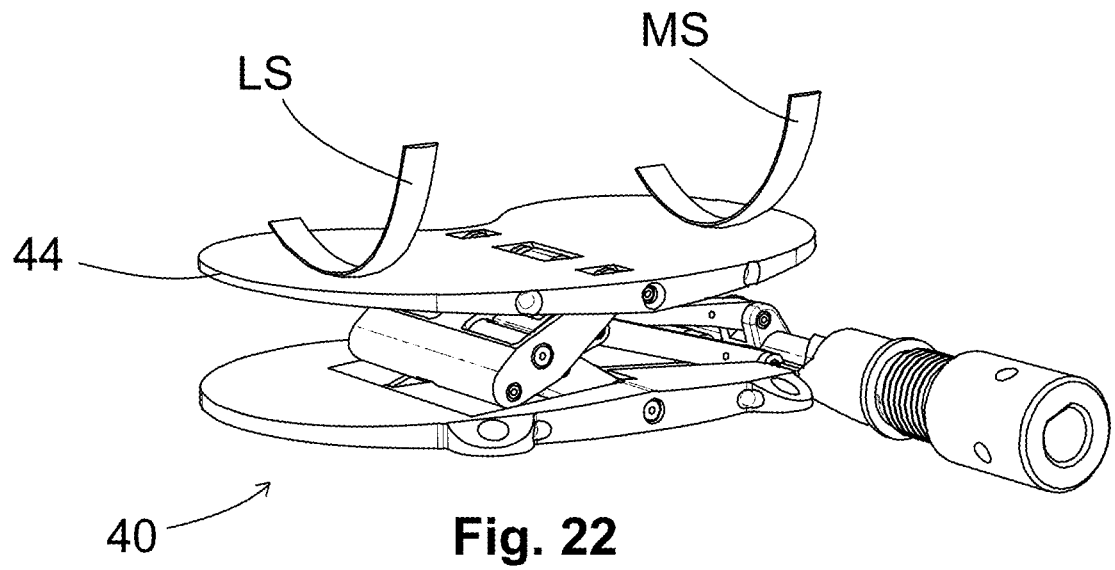
FIG. 22 is a perspective view showing plots of collected spline data superimposed on the top plate of a tensioner-balancer.
Figure 23:
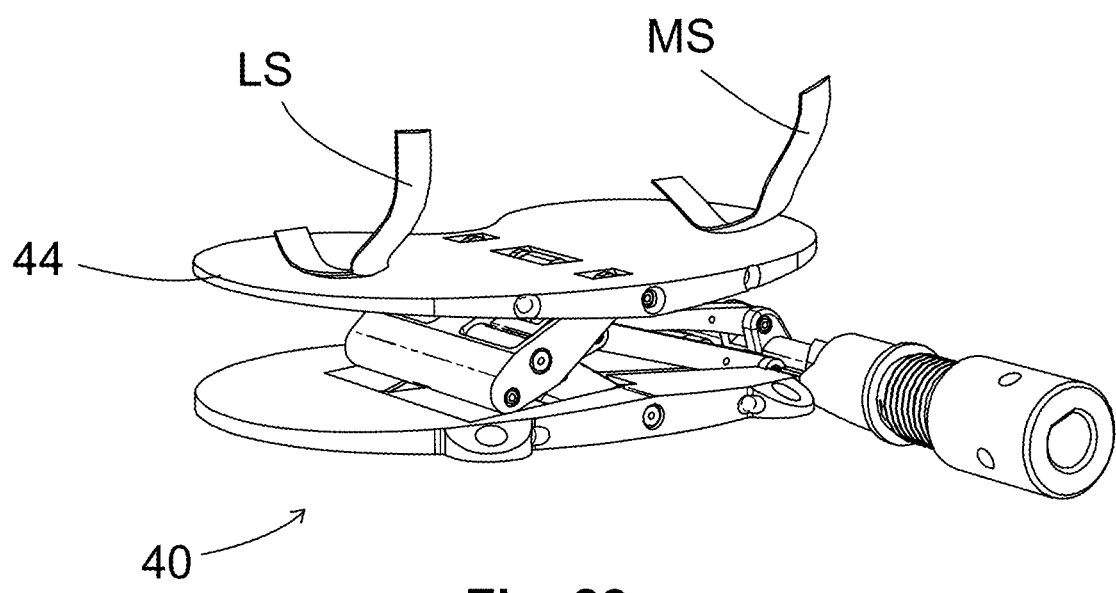
FIG. 23 is another perspective view showing plots of collected spline data superimposed on the top plate of a tensioner-balancer.

The knee joint J is then moved through its range of motion from full extension to full flexion while collecting data from the tensioner-balancer 40 and tracking markers 86, 88, and/or 90. Specifically, the instantaneous location of the load centers LC and MC are recorded and correlated to the flexion angle of the knee joint (as determined from the tracking marker data). The recorded data is represented by the medial spline "MS" and the lateral spline "LS" as shown in FIG. 21. FIGS. 22 and 23 show the splines superimposed on the top plate of the tensioner-balancer 40. FIG. 22 illustrates idealized or nominal shape splines. FIG. 23 illustrates splines indicative of discontinuities, "notching", articular irregularities and incongruencies which may be found in an actual or pathological knee joint J. The splines may be characterized by two or more points (a starting point and terminal point, with zero or more intermediary points in between), each with a location (defined by Cartesian or polar coordinates relative to a fixed reference point defined by tracker on the tensioner-balancer baseplate), a direction, and a first and second derivative. Each spline point may also have an associated flexion angle and load. Given the datum of the tibia cut surface, and the fact that the tensioner balancer is fixed relative to the tibia and fixed relative to the tibia cut surface, the tracking system is functional with tracker 86 or 90 individually, or using both synchronously.

The spline information may be used to select an appropriate endoprosthetic, specifically a femoral component. Multiple femoral components of different sizes and articular surface profiles may be provided, and the one which has the best fit to the splines MS, LS may be selected for implantation. Alternatively, the spline information may be used to generate a profile for manufacture of a patient-specific femoral component.

The spline information may be used in conjunction with other information to determine appropriate cutting planes for the femur F. For example, the back surface 28 of the femoral component 14 has a known relationship to the articular surface 30. The desired final location and orientation of the articular surface 30 is known in relation to the top plate 44 of the tensioner-balancer 40, which serves as a proxy for the tibial component 12. The final location of the tibial component 12 is known in relationship to the position of the tibial tracking marker 90. Finally, the actual orientation and location of the femur F in relation to the other parts of the joint J is known from the information from the femoral tracking marker 88. Using appropriate computations, the orientation and location of the cutting planes of the femur F can be calculated and referenced to the position the tensioner-balancer 40 or its tracker 86, or referenced to the position of the tibia or its tracker 90.

Figure 24:
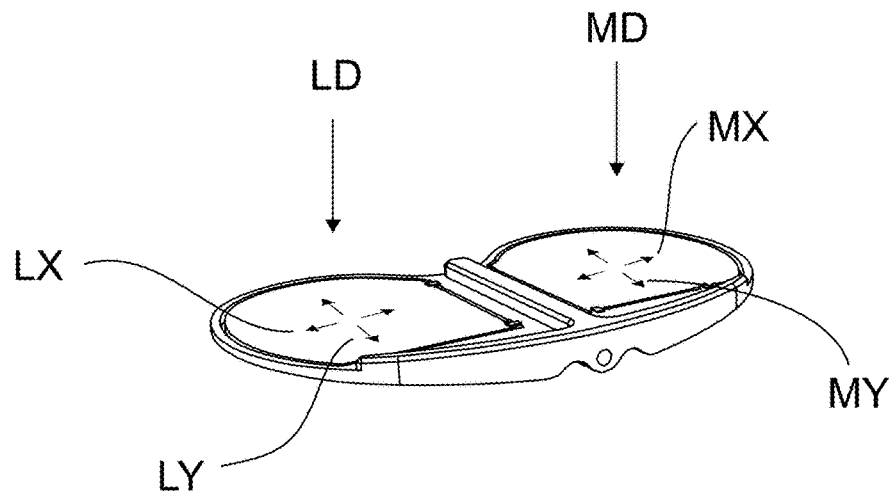
FIG. 24 is a diagram showing a tensioner-balancer labeled with data parameters.
Figure 25:
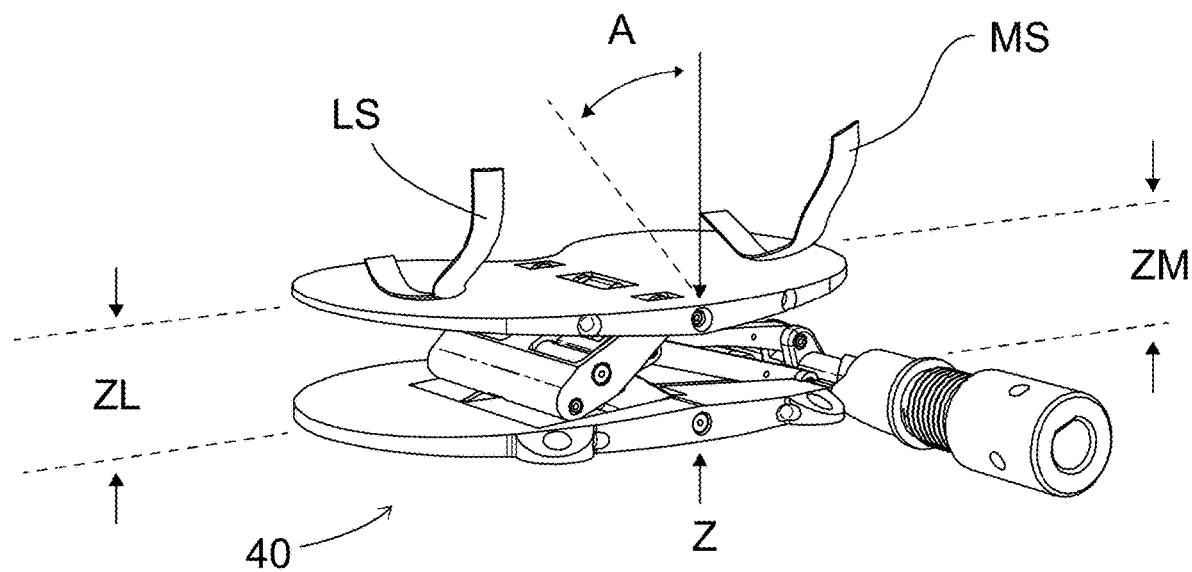
FIG. 25 is a diagram showing a tensioner-balancer labeled with data parameters.
Figure 26:
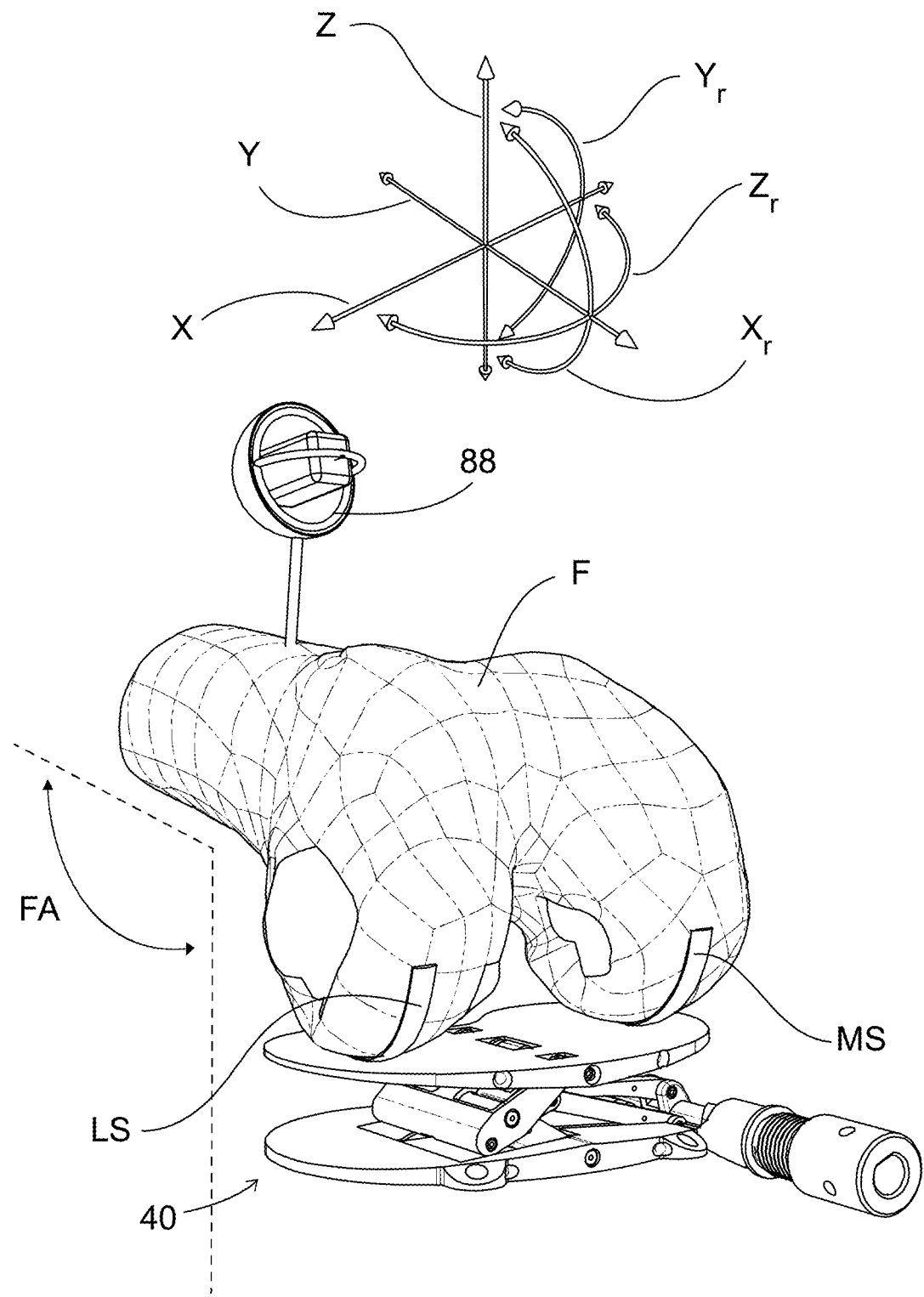
FIG. 26 is a diagram showing a knee joint and tensioner-balancer labeled with data parameters.

With reference to FIGS. 24-26, it will be understood that the tensioner-balancer 40 and associated tracking apparatus may be used to collect the following data related to the knee joint: distraction height "Z" of the top plate 44, tilt angle "A" (i.e., *varus*-valgus) of the top plate 44), medial and lateral distraction heights "ZM", "ZL" (e.g., derived from the top plate distraction height and top plate tilt angle), the medial and lateral spline data, the position of the contact points of the femur F on the top plate (medial-lateral and anterior-posterior) (MX, MY, LX, LY), the distraction load on the medial and lateral condyles (MD, LD), the knee joint flexion angle "FA", and the abovementioned 6-DoF position data for each tracking marker (X, Y, Z position and Xr, Yr, Zr rotation).

In collecting the spline information and tracking information, it is helpful to make reference to one or more positional datums. Each datum is a 6 DoF reference (e.g. position and orientation about three mutually perpendicular axes). The datum may refer to a geometrical construct as well as a virtual software construct. In one example, the datums described herein may be established by physically registering landmarks on at least one of the tensioner-balancer, the femur bone, and the tibia bone.

Figure 27:
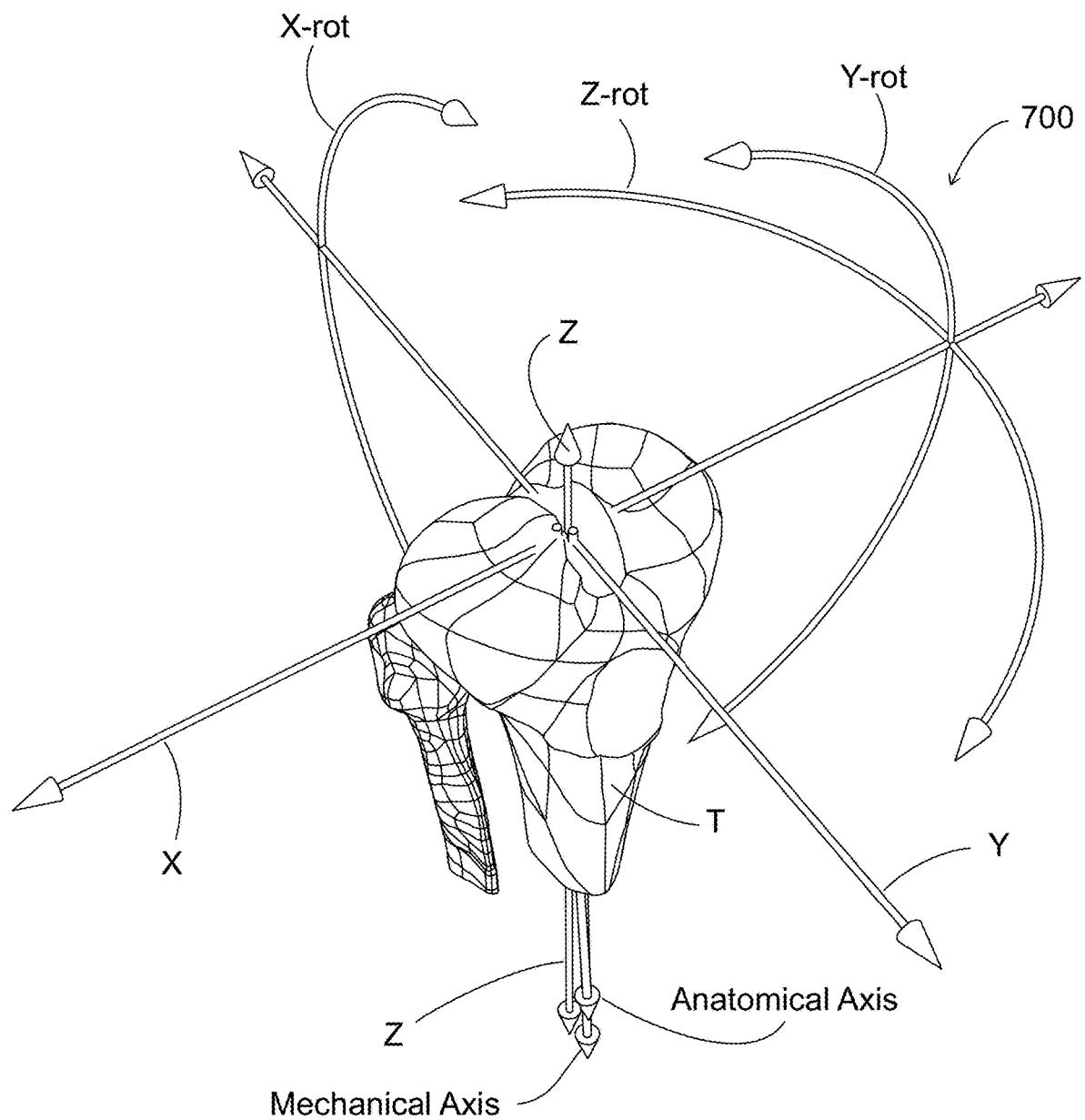
FIG. 27 is a perspective view of a tibia having a reference datum superimposed thereupon.

FIG. 27 shows an example of a datum 700 superimposed on a tibia T. As illustrated, the datum 700 is a coordinate framework with X, Y, and Z axes, as well as rotations about each of those three axes. Some respects of the position and orientation of the datum 700 relative to the tibia T may be arbitrary selected. In one example, the Z-axis may be positioned in a predetermined relationship to a known anatomical reference such as the tibia anatomical axis or tibia mechanical axis. The XY plane may be positioned normal to the Z axis and intersecting the tibia at the position of an actual or assumed tibial plateau cutting plane, or oriented at some defined angular displacement relative to an actual or assumed tibia cutting plane. Thus positioned, the datum 700 provides a reference for measurements using the tracking markers and/or the tensioner-balancer 40.

Figure 28:
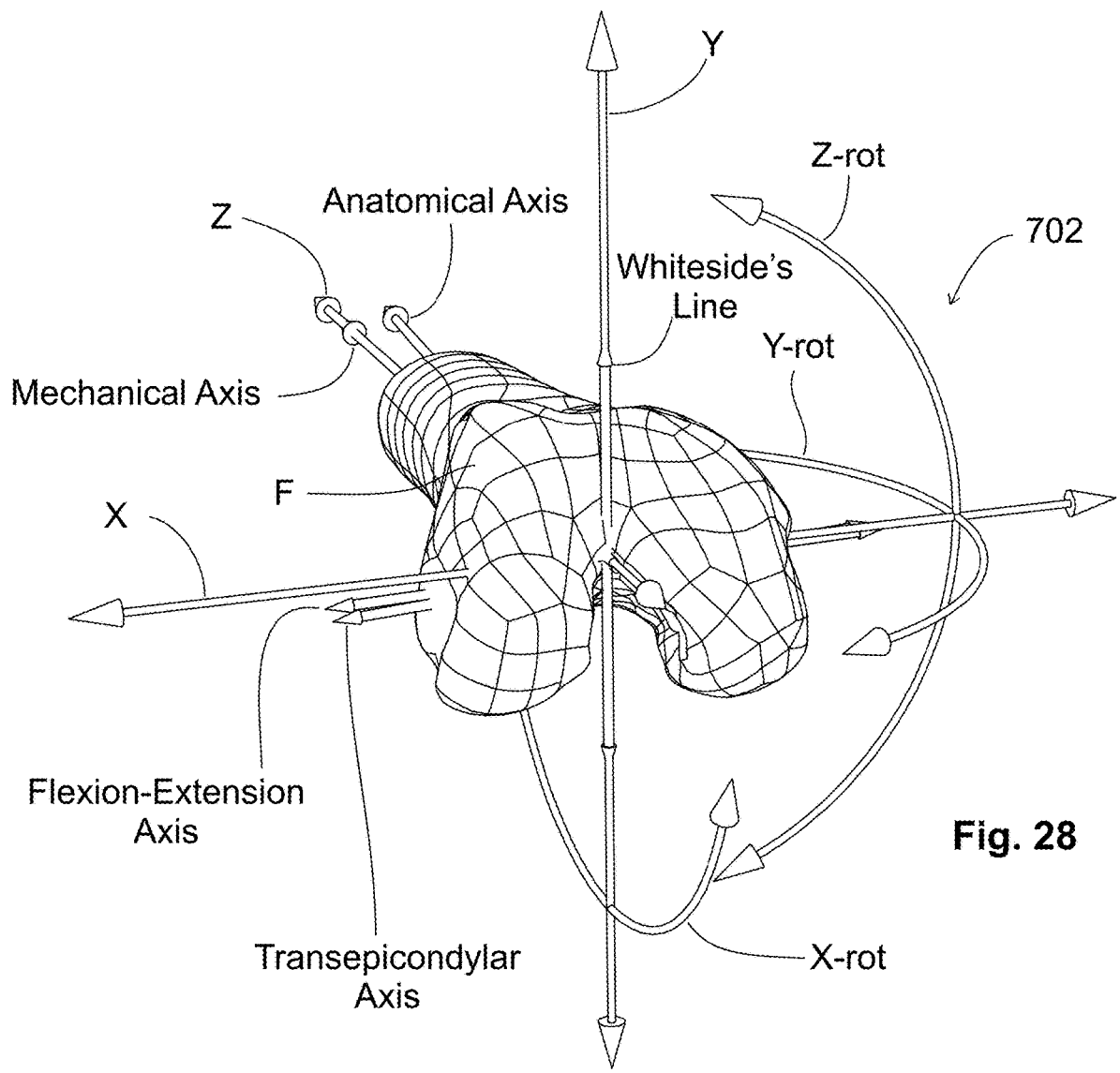
FIG. 28 is a perspective view of a femur having a reference datum superimposed thereupon.

FIG. 28 shows an example of a datum 702 superimposed on a femur F. As illustrated, the datum 702 is a coordinate framework with X, Y, and Z axes, as well as rotations about each of those three axes. Some respects of the position and orientation of the datum 702 relative to the femur F may be arbitrary selected. In one example, the Z-axis may be positioned in a predetermined relationship to a known anatomical reference such as the femur anatomical axis or femur mechanical axis. The XY plane may be positioned normal to the Z axis. Longitudinally, the XY plane may be positioned, for example intersecting a anatomical reference such as Whiteside's line. Thus positioned, the datum 702 provides a reference for measurements using the tracking markers and/or the tensioner-balancer 40.

Figure 29:
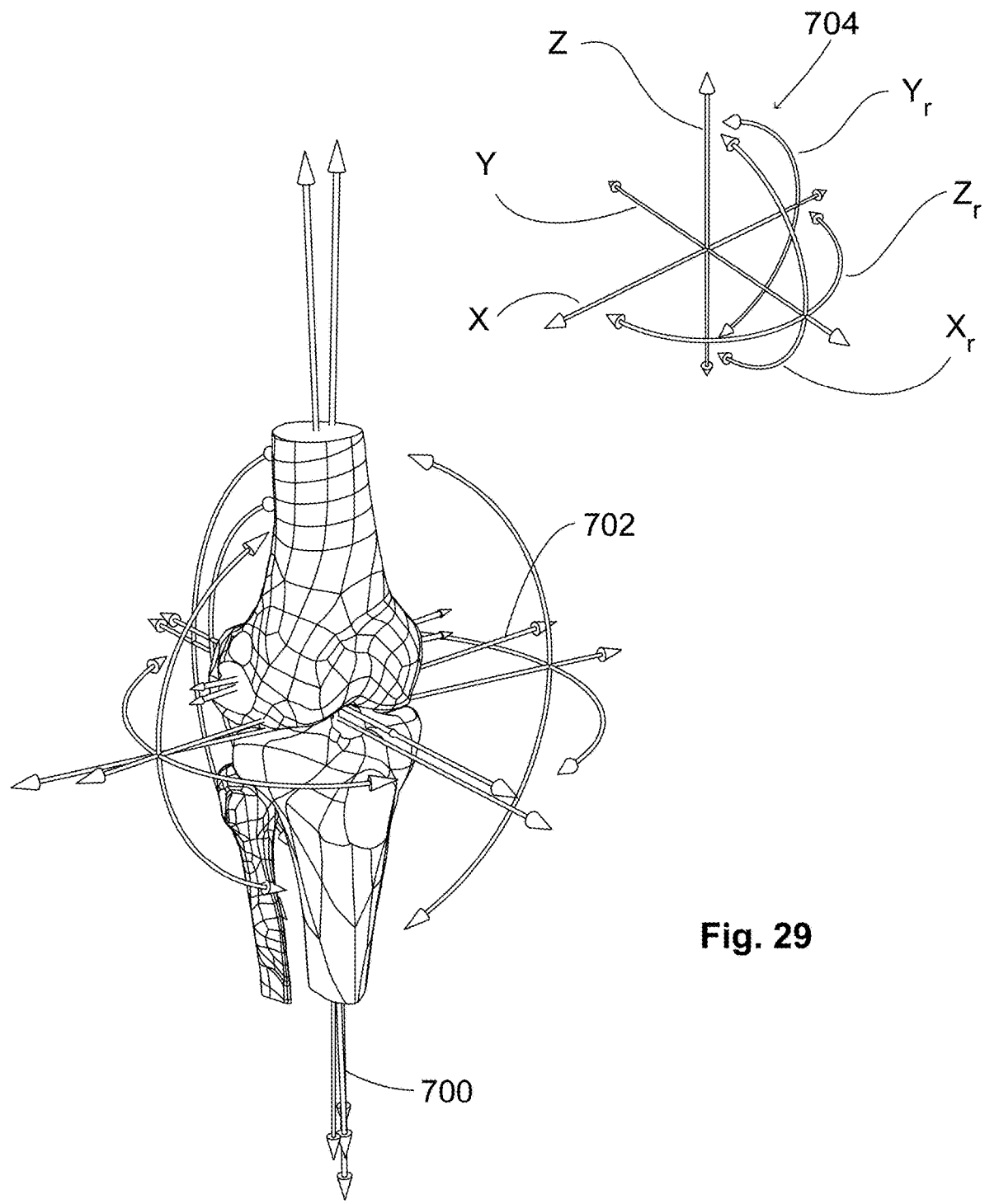
FIG. 29 is a perspective view of a knee joint having reference datums superimposed thereupon.

FIG. 29 shows the assembled knee joint J with the two datums 700, 702. For measurement and computational purposes, one of the datums may be designated a "primary" datum, with the remaining datums being designated as "secondary" datums. In one example, the datum 700 associated with the tibia T may be designated a primary datum. With the position and orientation of the datum 700 known in space (i.e., from tracking marker information), the position and orientation of the datum 702 associated with the femur F may be reported as a relative position and orientation to the datum 700 (primary data). It is noted that, as a supplement or as an alternative to information from the tracking markers described above, other types of measurement apparatus may be used to collect position and orientation data of the datums. Nonlimiting examples of measurement apparatus include devices such as optical systems, radiofrequency-based systems, radiographic systems, and LIDAR.

In another example, an arbitrary primary datum 704 may be positioned at arbitrary predetermined location outside of the body. With the position and orientation of the primary datum 704 known in space, the position and orientation of the datum 700 associated with the tibia T (considered a secondary datum in this case) may be reported as a relative position and orientation to the datum 704. In this example, the position and orientation of the datum 702 associated with the femur F would also be considered a secondary datum and would be reported as a relative position and orientation to the datum 704.

Figure 30:
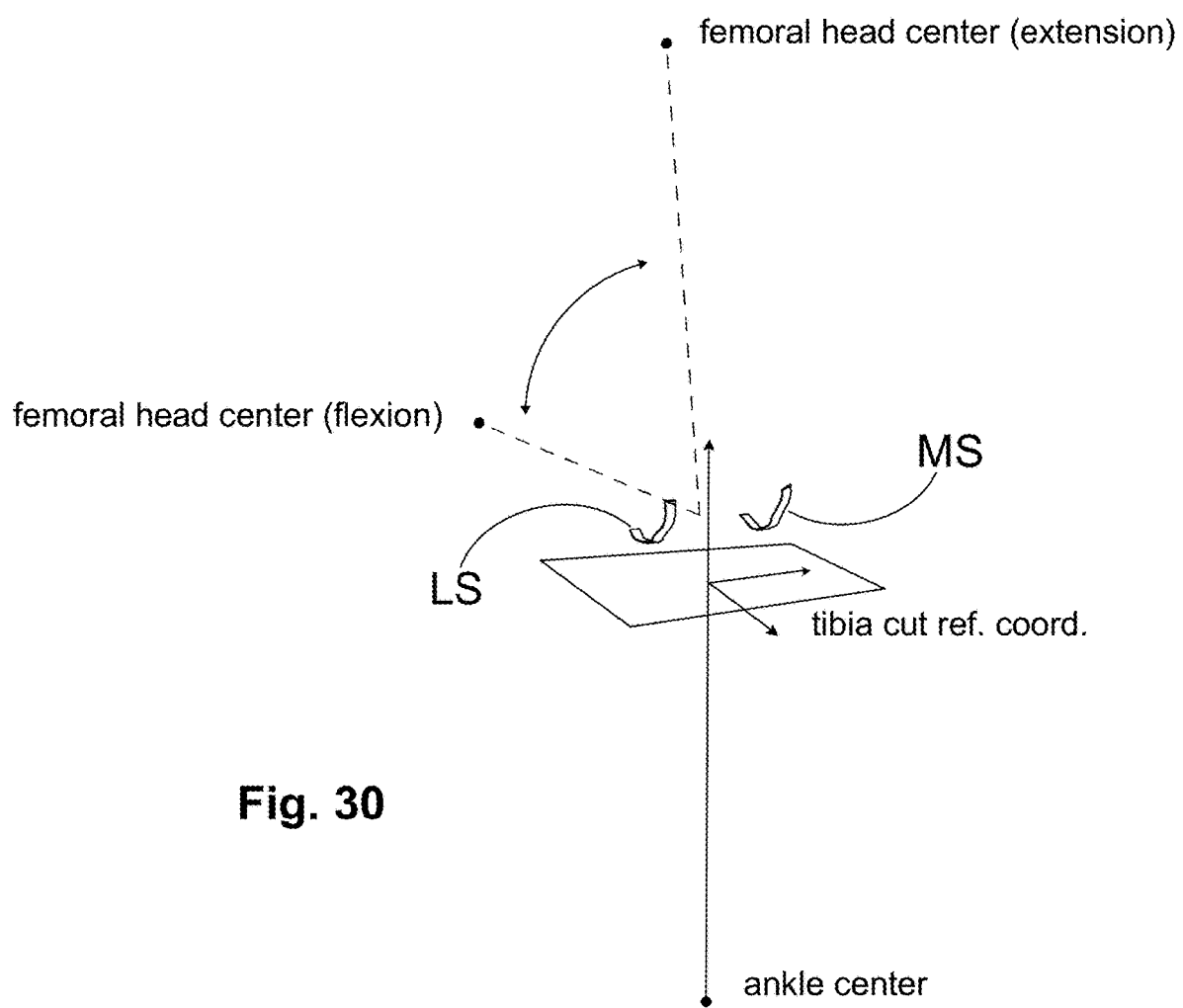
FIG. 30 is a diagram illustrating data collected by tensioner-balancer and tracking markers.

FIG. 30 illustrates the organization of the data collected by the tracking markers in the tensioner-balancer 40. It can be seen that the overall modeling of the complex 3D knee geometry (i.e. a digital geometric model) can be reduced for practical purposes to a relatively small set of elements including: tibial plateau cut plane, the medial and lateral splines, the position of the medial and lateral spine contacts on the tibial plateau cut plane, an axis or vector passing from the ankle center through the tibial plateau cut plane, and a femoral axis passing through the femoral head.

Figure 1:
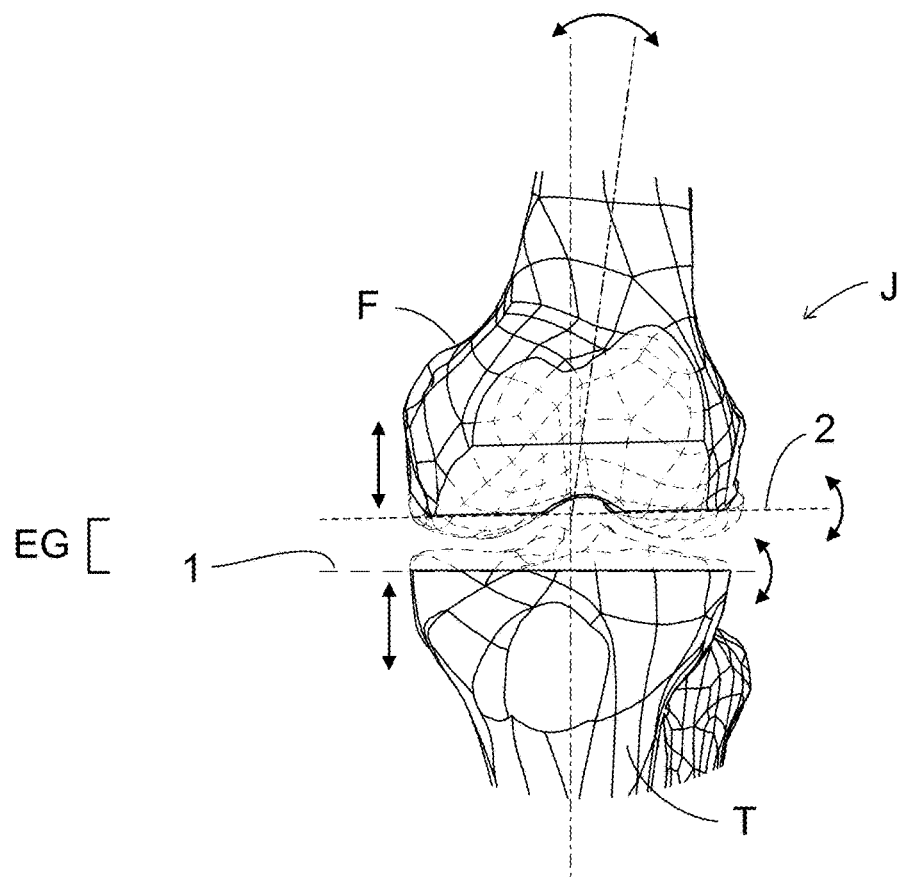
FIG. 1 is a view of the anterior aspect of the human knee joint in extension showing cutting planes for a total knee arthroscopy.
Figure 2:
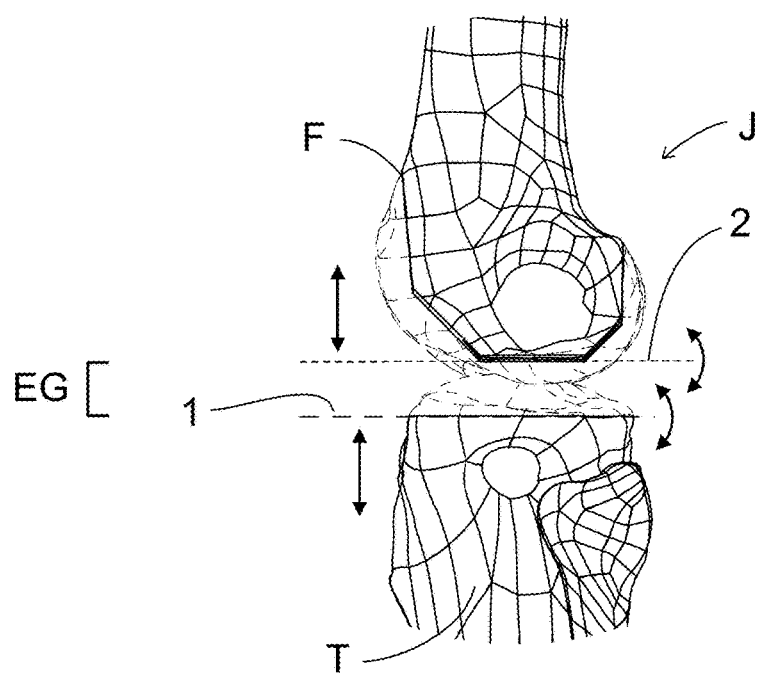
FIG. 2 is a view of the lateral aspect of the human knee joint of FIG. 1.
Figure 3:
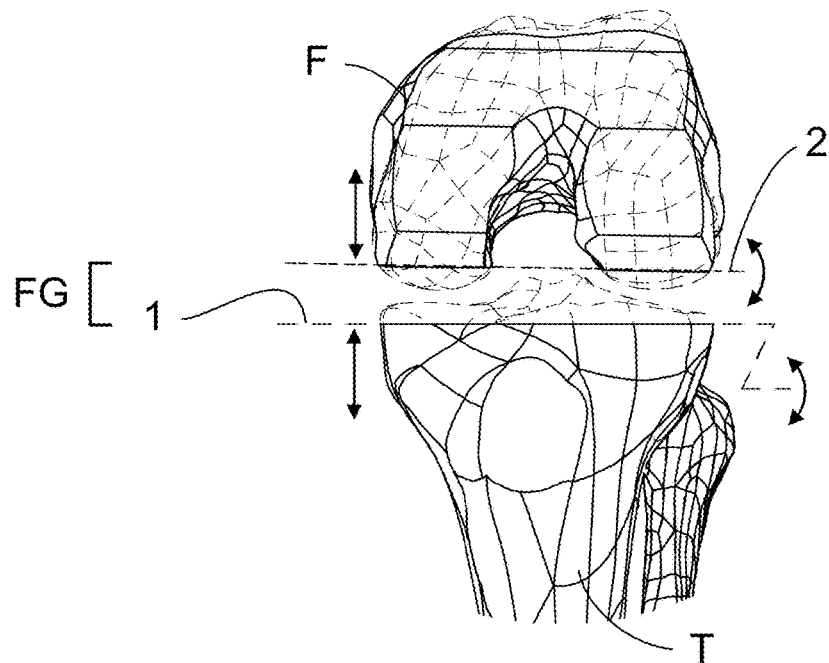
FIG. 3 is a view of the anterior aspect of the human knee joint in flexion showing cutting planes for a total knee arthroscopy.
Figure 4:
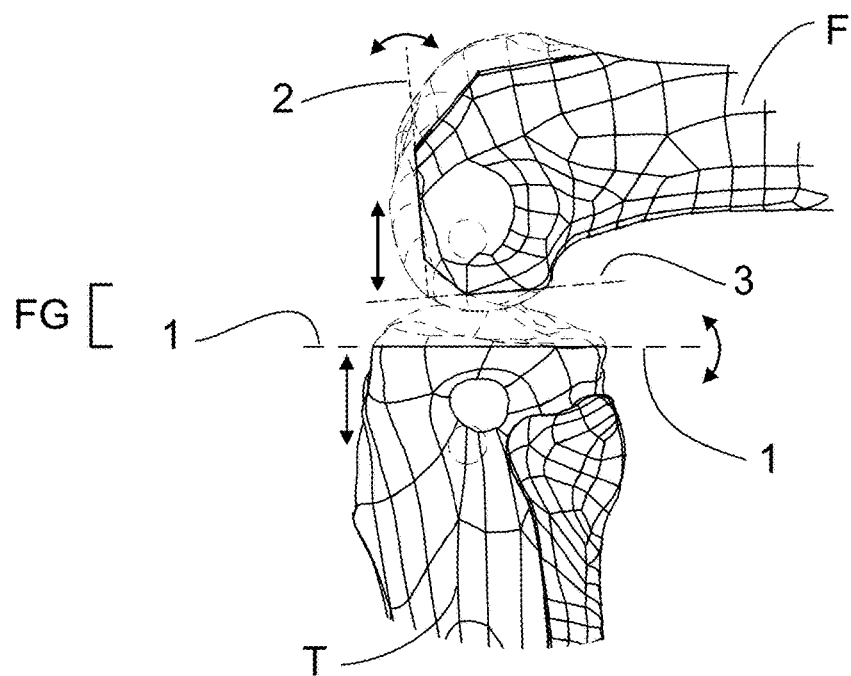
FIG. 4 is a view of the lateral aspect of the human knee joint of FIG. 3.
Figure 5:
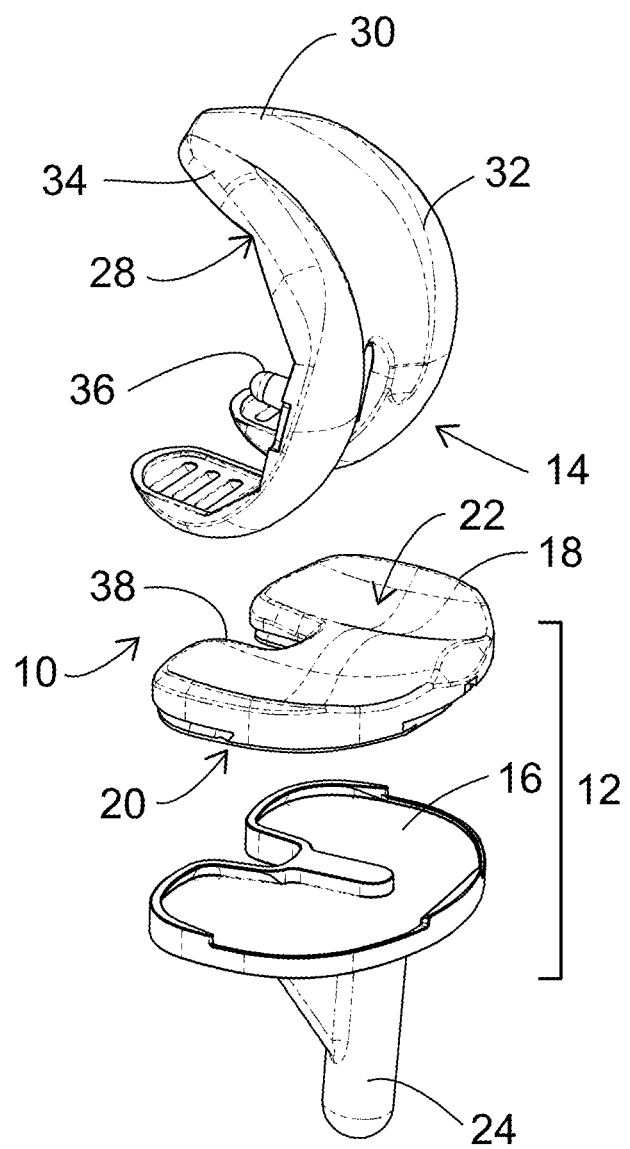
FIG. 5 is an exploded perspective view of a representative knee endoprosthesis.
Figure 6:
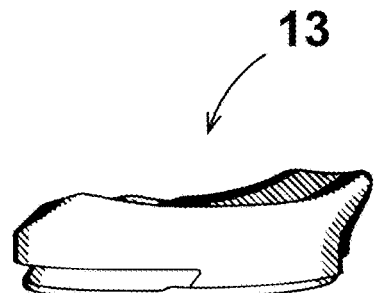
FIG. 6 is a view of the lateral aspect of a constrained-type tibial component.
Figure 7:
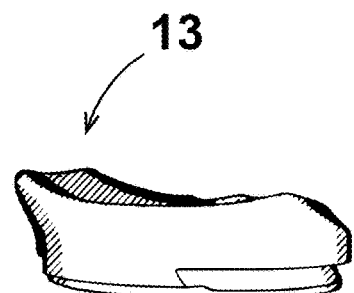
FIG. 7 is a view of the medial aspect of the tibial component of FIG. 6.
Figure 8:
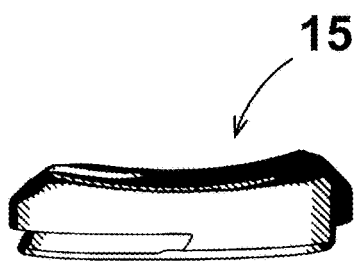
FIG. 8 is a view of the lateral aspect of a medial-pivot tibial component.
Figure 9:
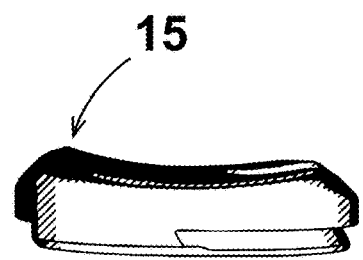
FIG. 9 is a view of the medial aspect of the tibial component of FIG. 8.
Figure 10:
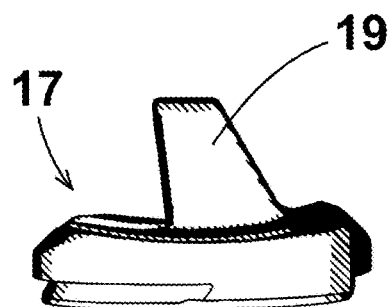
FIG. 10 is a view of the lateral aspect of a posterior-stabilized type tibial component.
Figure 11:
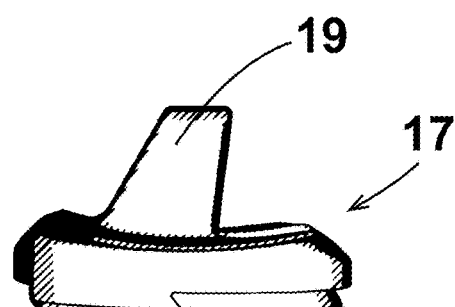
FIG. 11 is a view of the medial aspect of the tibial component of FIG. 10.

A nominal distal femoral cutting plane 2 (FIG. 2) may be determined by anatomical analysis using known anatomical references and techniques. For example, this plane 2 could be uniformly spaced away from and parallel to the tibial cutting plane 1 (i.e., a nominal cut). Alternatively, this plane 2 could be at an oblique angle to the tibial cutting plane 1, in one or more planes (i.e., simple or compound tilted cut, potentially usable as a corrective cut).

Figure 31:
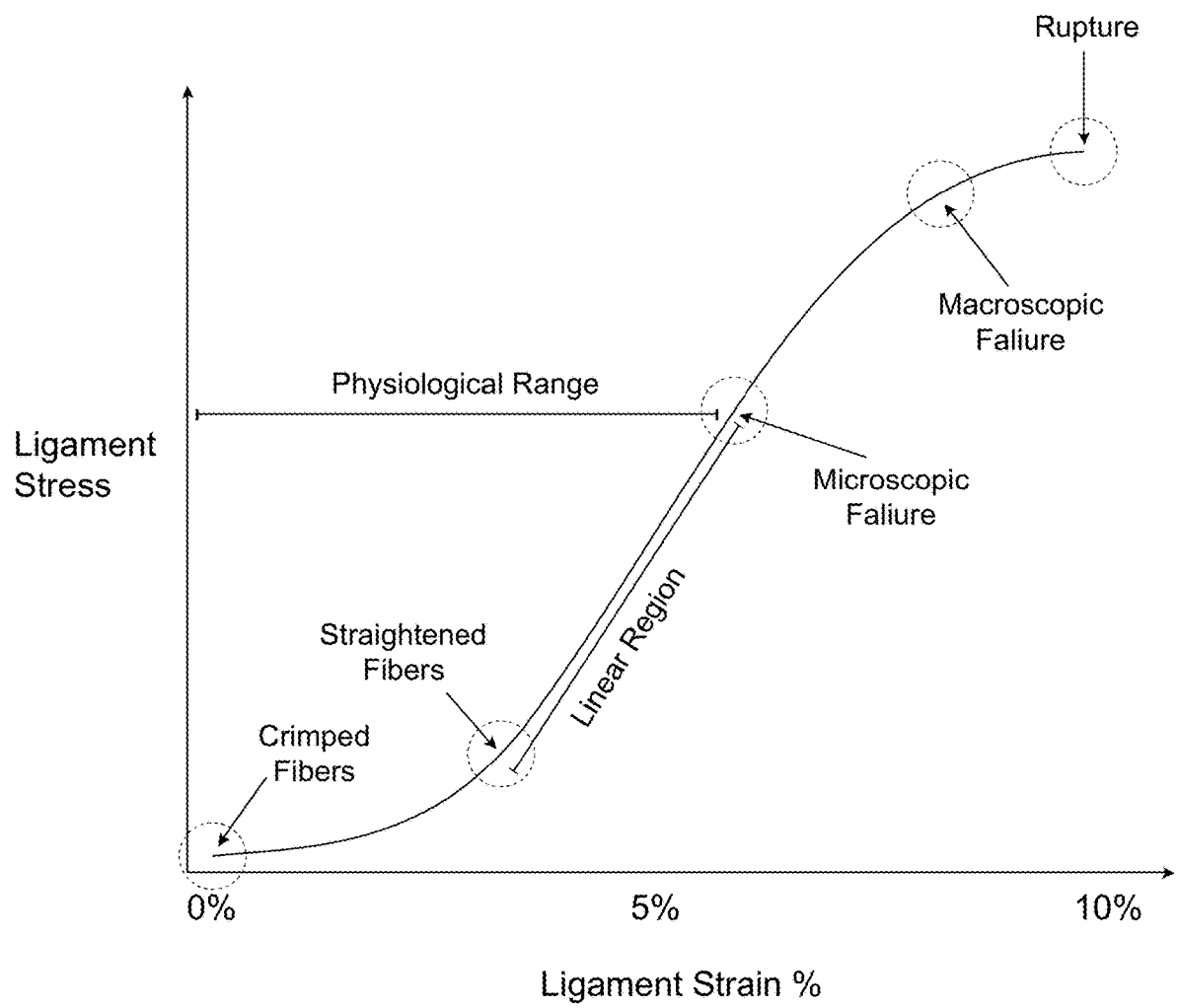
FIG. 31 is a representative stress-strain curve of a ligament of a human joint.
Figure 32:
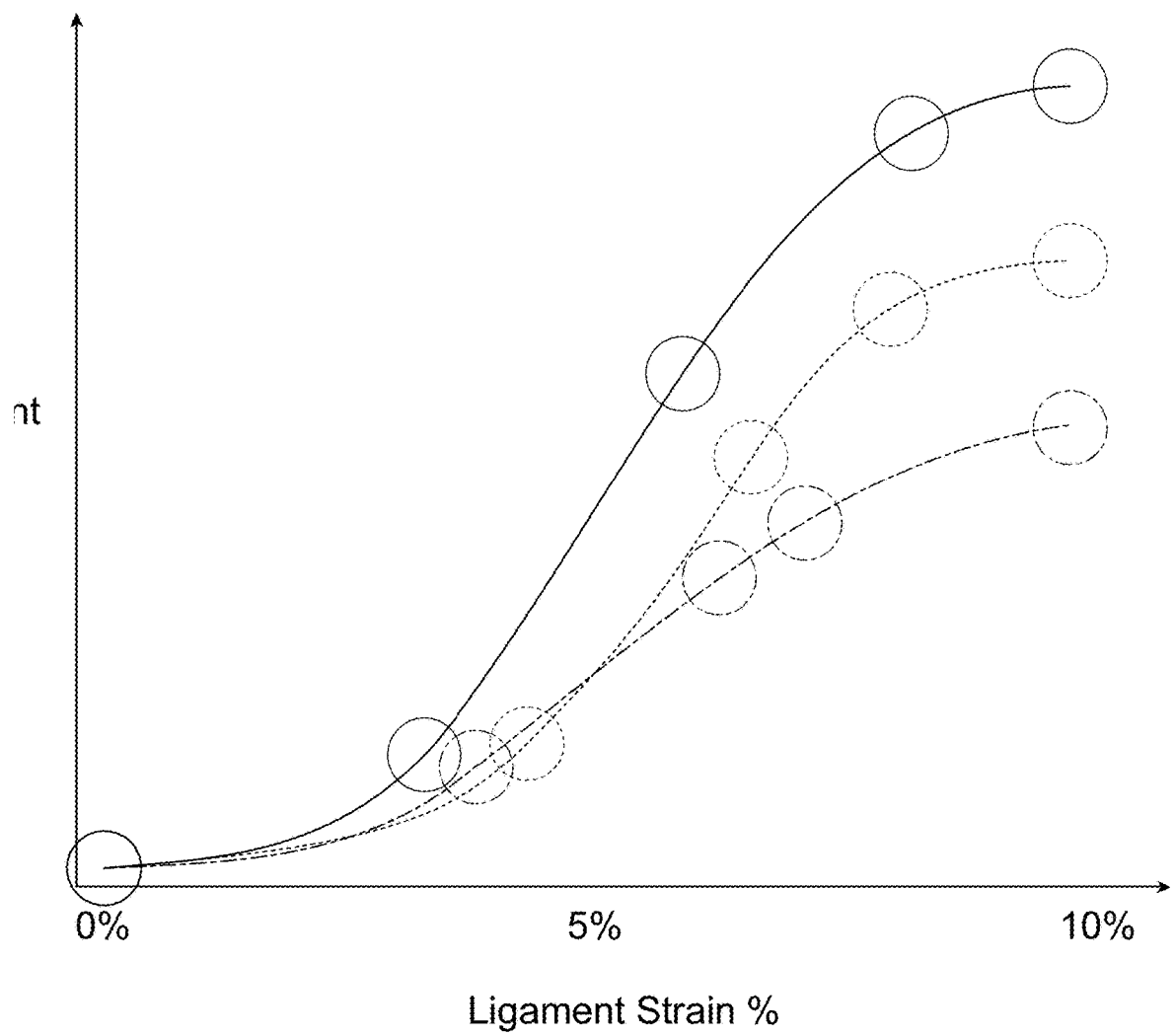
FIG. 32 is a series of stress-strain curves of human ligaments for different individuals.

FIG. 31 is a schematic diagram representing the stiffness of a human knee ligament. This is a stress-strain curve illustrating ligament percent strain on the X-axis and ligament stress on the Y-axis. Beginning at the curve origin it can be seen that there is an initial nonlinear range as the individual ligament fibers are strained and tend to "align" themselves from laxity to parallel paths under a very low initial tension when a load is applied (i.e. strain is applied without any resultant loading), followed by a generally linear region where the ligament is seen to behave more elastically and/or viscoelastically. It will be understood that within this region, the data may not represent a pure line according to a mathematical definition of the form y=mx+b. However, it will generally be a close approximation thereof. Accordingly, for convenient reference purposes, this portion of the curve may be referred to as a "linear" region. As stress is increased, microscopic failures began, giving way to macroscopic failure and finally to rupture of the ligament when its breaking strength is exceeded. This curve indicates the overall characteristic of a given ligament. However, it will be understood that the specific tensile characteristics will vary for an individual patient or patient population based on numerous factors such as age, gender, body mass, physique, level of athletic training, and existence or absence of pathology. In FIG. 32, the solid line is representative of a healthy young athlete, while the dotted line is representative of an elderly person, and the dot-dash line is representative of a person having soft tissue damage.

Figure 33:
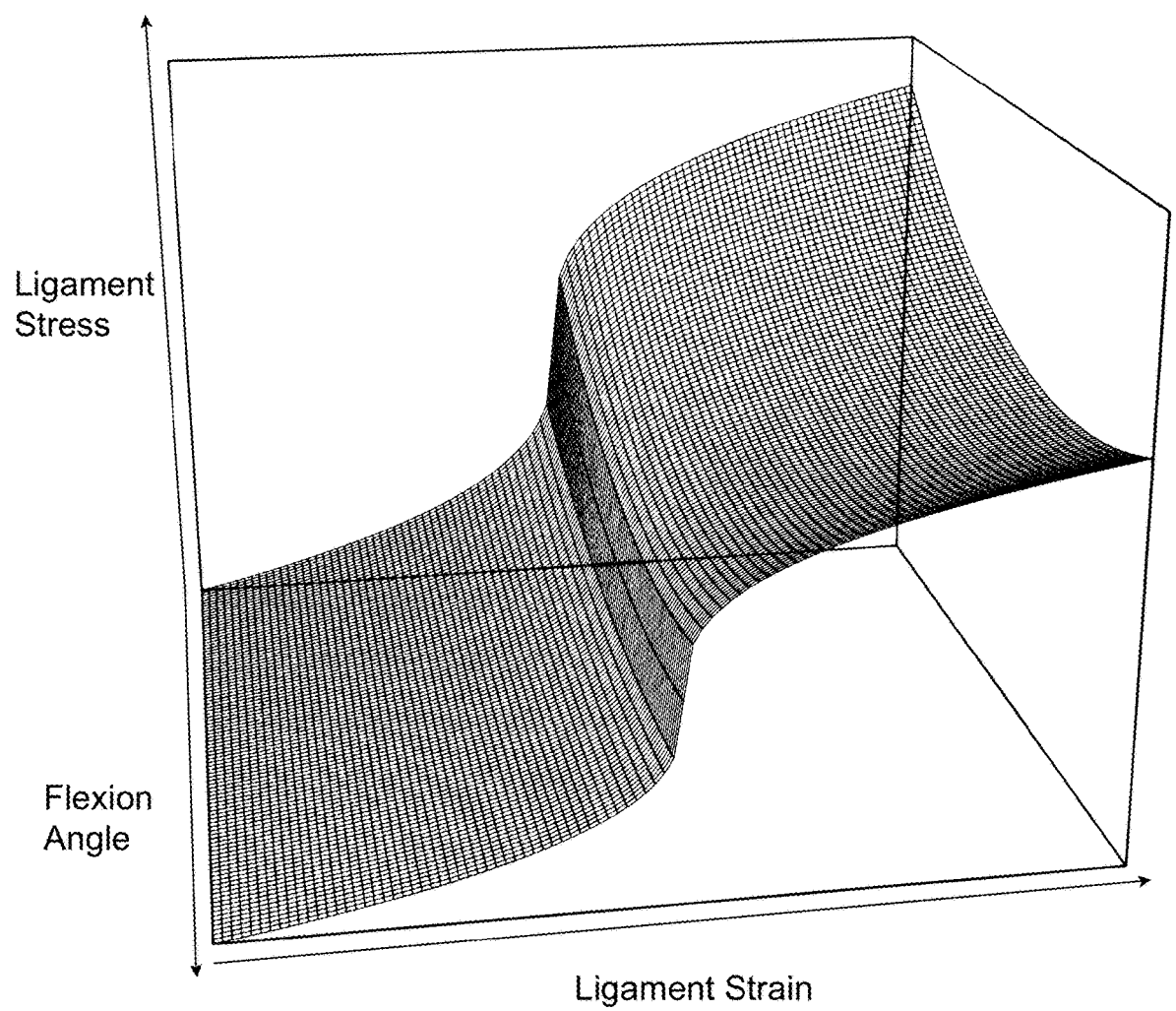
FIG. 33 is a 3D plot of stress-strain curves of human ligaments for a human knee joint of a specific individual, over a range of knee flexion angles.

It will be understood that the stress-strain characteristics are dynamic in nature and can vary with the flexion angle of the knee joint J. Referring to FIG. 33, this is a three-dimensional plot of ligament stress versus strain over a range of flexion angles. This is due to the fact that the ligaments are in fact not point-to-point lines, but are masses of soft tissue which engage and disengage different parts of their bone attachment "footprints" as the joint is flexed.

It will be understood that the ligament properties and characteristics described above can be determined by the tensioner-balancer device as a stand-alone measurement apparatus with the use of mathematical computations derived from an understanding of forces acting on the joint and anatomical measurements.

It will be understood that anatomical measurements may include ligament geometry including length, width, diameter, cross-sectional-area, angle, and footprint area. Mechanical and anatomical axes, as well as a live reading of the flexion angle of the knee, may be measured in 6 degrees of freedom with body-worn tracking markers, non-line-of-sight trackers, inertial measurement units, goniometers, or the like.

Figure 34:
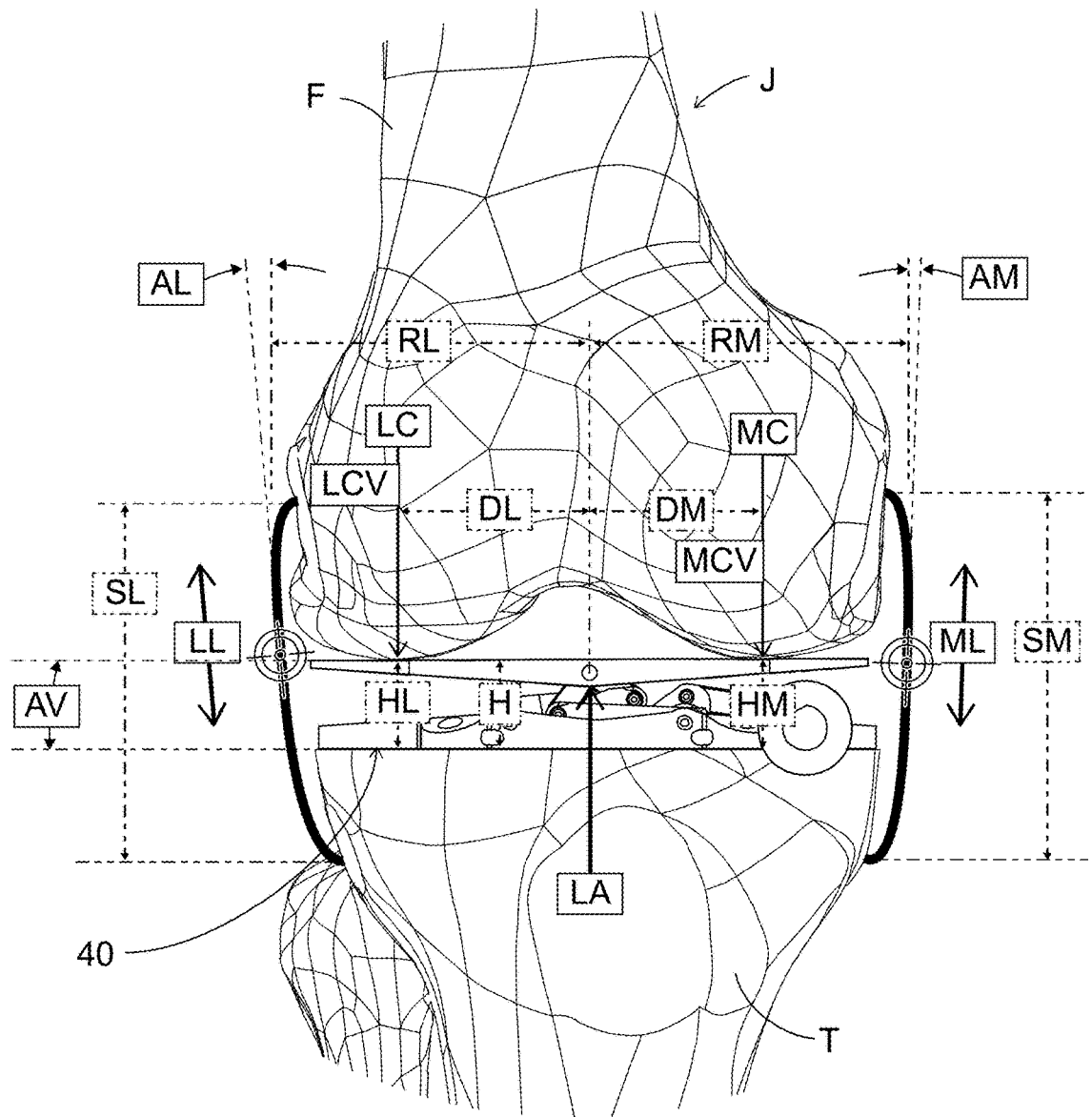
FIG. 34 is a schematic diagram of a knee joint in an extended position, with a tensioner-balancer inserted therein.
Figure 35:
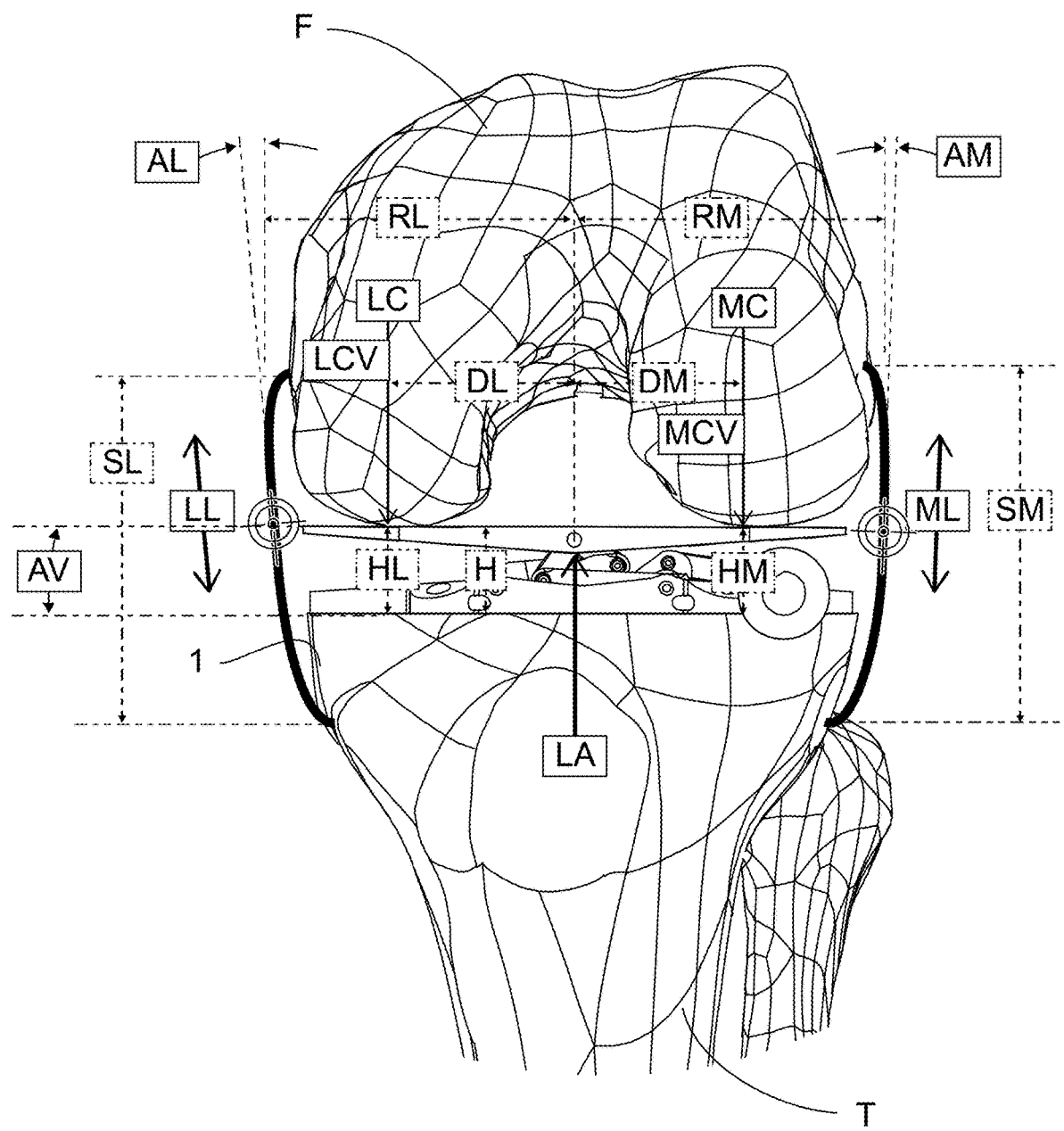
FIG. 35 is a schematic diagram of the knee joint of FIG. 34, in a flexed position.
Figure 36:
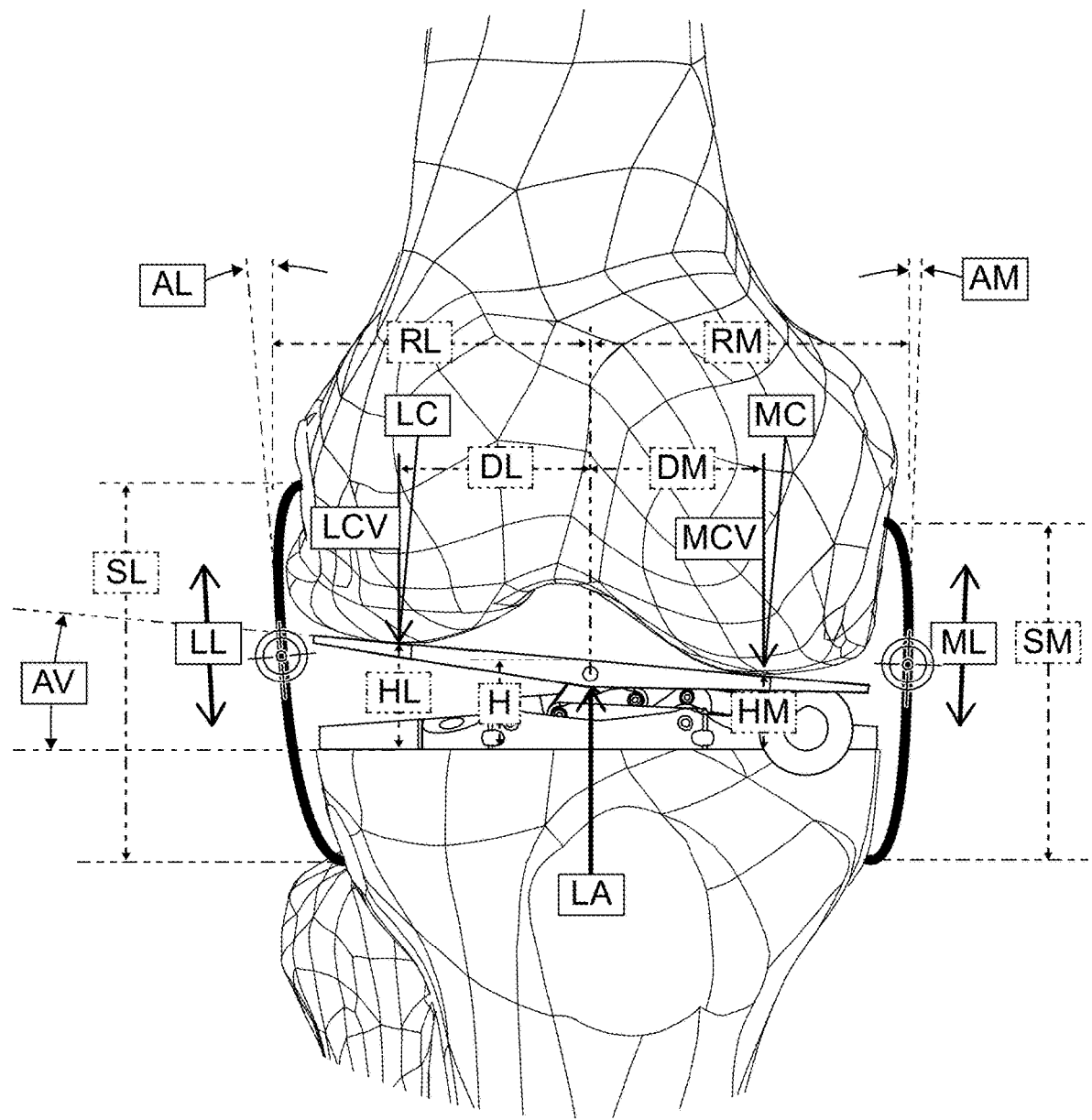
FIG. 36 is a schematic diagram of a knee joint in an extended position, with a tensioner-balancer inserted therein.

One method of measuring ligament stiffness may be understood with reference to FIGS. 34-36. FIG. 34 is a schematic diagram of a knee joint J with a tensioner-balancer 40 inserted therein in an extended position (e.g., 0 degrees flexion), while FIG. 35 shows the knee joint J in a flexed position. Various measurements and parameters are labeled on diagram. Dimension "HL" is a measured height at the lateral condyle. Dimension "HM" is a height at the medial condyle. "H" is a height at the pivot axis 47 of the top plate 46. Arrow "LC" represents compressive force acting through the pivot axis 47 of the top plate 46 (see FIG. 12). Arrow "LC" represents compressive force acting through the lateral condyle, and arrow "LCV" is a vertical component of LC. Arrow "LA" represents compressive force acting through the pivot axis 47 of the top plate 46. Arrow LA vector is normal to the base plate 42 and represents a "vertical" direction for purposes of explanation. Arrow "MC" represents compressive force acting through the medial condyle, and arrow "MCV" is a vertical component of MC. Dimension "DL" represents the distance between the pivot axis 47 of the top plate 46 and the line of action of compressive force LC. Dimension "DM" represents the distance between the pivot axis 47 of the top plate 46 and the line of action of compressive force MC. Dimension "AV" represents the tilt angle of the top plate 46. It will be understood from the description above that the tensioner-balancer 40 is sufficiently instrumented that the values HL, HM, LA, LC, MC, DL, and DM can all be determined either through direct sensing or computation of values based on sensor inputs, such as inputs from the strain gages 58 described above. This information can be used to compute pertinent physical characteristics of the soft tissue, namely the medial collateral ligament (MCL) and the lateral collateral ligament (LCL).

In FIG. 34, the dimension "RM" represents the distance between the pivot axis 47 of the top plate 46 and the lateral location of the area centroid of the MCL (designated by a cross-hair symbol). The dimension "RL" represents the distance between the pivot axis 47 of the top plate 46 and the lateral location of the area centroid of the LCL (designated by a cross-hair symbol). Dimension "AM" represents the angle in the coronal plane of the line of action of the MCL measured from vertical. Dimension "AL" represents the angle in the coronal plane of the line of action of the LCL measured from vertical. Dimension "SM" represents the overall length of the MCL. Dimension "SL" represents the overall length of the LCL. Arrow "ML" represents the tensile load on the MCL. Arrow "LL" represents the tensile load on the LCL.

In one example, knowing the medial-side deflection (i.e., the change in dimension HM) as well as distance DM and distance RM, a geometric transformation may be performed to determine the deflection of the MCL (i.e., the change in dimension SM). The required computations may be carried out using a software application. A similar geometric transformation may be carried out to determine the deflection of the LCL (i.e., the change in dimension SL) when the change in dimension HL, distance DM, and distance RL are known). In another example, knowing the medial-side compressive load MC, as well as distance DM and distance RM, computation may be performed to determine the medial-side tensile load ML. In another example, knowing the lateral-side compressive load LC, as well as distance DL and distance RL, computation may be performed to determine the lateral-side tensile load LL. In computing the deflections and loads on the MCL and/or LCL, the orientation of the ligaments may be taken into account. The above-described computations will result in the vertical components of ML or LL, or vertical components of change in SM or SL. If the angles AM or AL are non-zero, a geometric transformation may be performed to determine the actual values of the ligament parameters acting along their lines of action.

For the purposes of the above-described computations, the distances RM and RL may be measured directly, measured indirectly, or may be determined by reference to a database or other source of statistical information. For example, a database may contain average joint dimensions based on population characteristics. E.g., a 5 percentile female or a 95 percentile male.

The following is an example of a computation for determining the vertical ligament load from calculated or measured contact load orthogonal to the top plate 46. This method uses trigonometric relationships to convert between orthogonal component and vertical component.

a. $LCV=LC/\cos(AV)$ b. $MCV=MC/\cos(AV)$ c. $LL=(LA*(RL/(RL+RM)))/\cos(AL)$ d. $ML=(LA*RM/(RL+RM))/\cos(AM)$ e. $HL=H*(1+\sin(AV))$ f. $HM=H*(1-\sin(AV))$ The above-described computations may be extended to the stress (force/area) in the ligaments by dividing the measured or computed load (force) by the cross-sectional area of the relevant ligament. The cross-sectional areas of the ligaments may be measured directly, measured indirectly, or may be determined by reference to a database or other source of statistical information.

Figure 37:
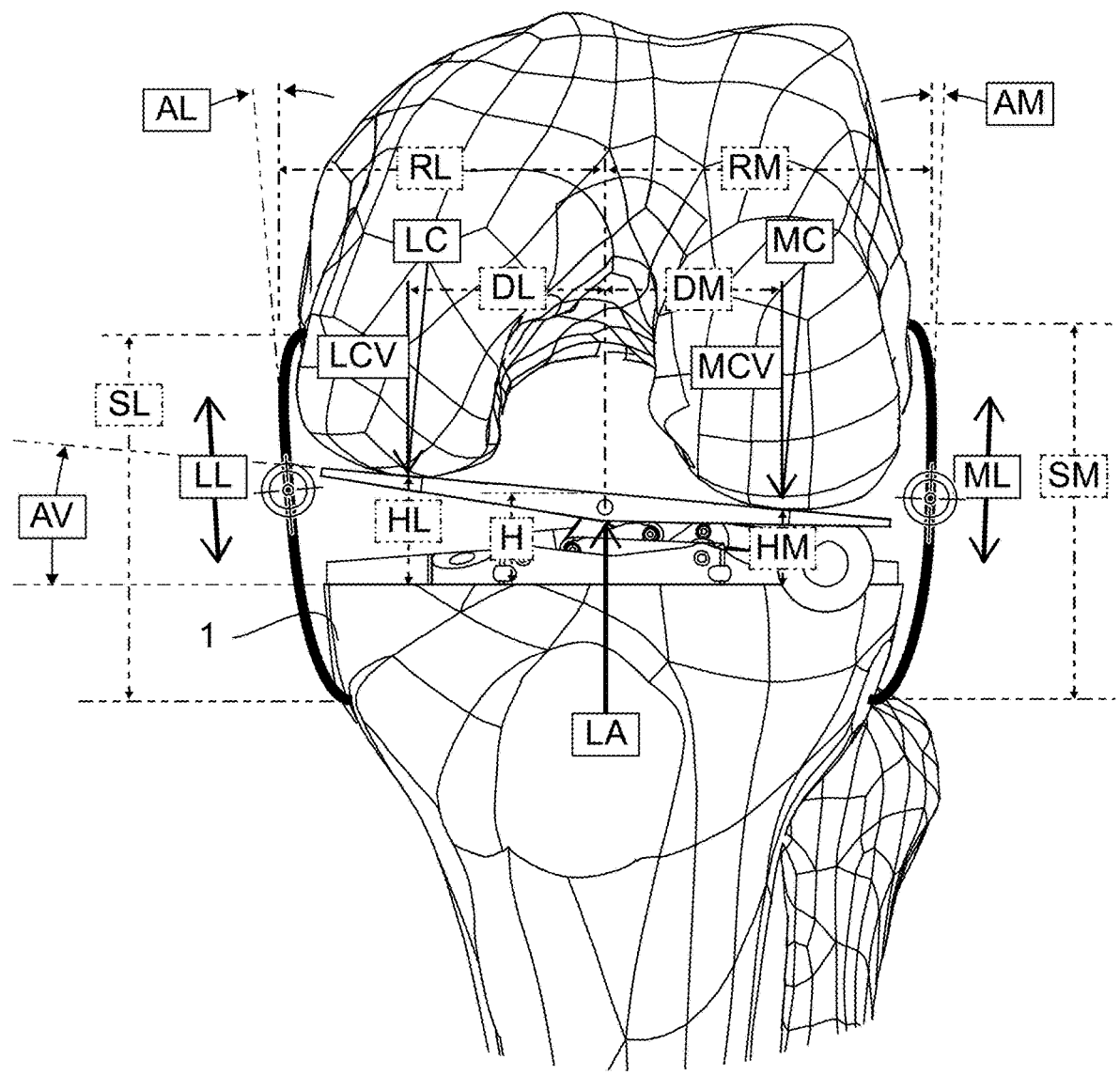
FIG. 37 is a schematic diagram of the knee joint of FIG. 36, in a flexed position.

In the example shown in FIGS. 34 and 35, the top plate angle AV is approximately zero. Accordingly, the values LC and MC as sensed have only a vertical component and may be used directly for additional computations. In other circumstances, the top plate angle AV may be nonzero. Examples experienced in actual patients can include angles of up to about 7 degrees. FIGS. 36 and 37 illustrate a knee joint J where top plate angle AV has a substantial nonzero value, for example about 5 degrees. As can be seen in FIG. 36, this has the consequence that values LC and MC act along non-vertical lines. It will be understood that in subsequent computations, it is desirable to know the vertical components of these values. Accordingly, where top plate angle AV is nonzero, a trigonometric transformation may be performed on the values LC and MC to derive their vertical components.

Figure 38:
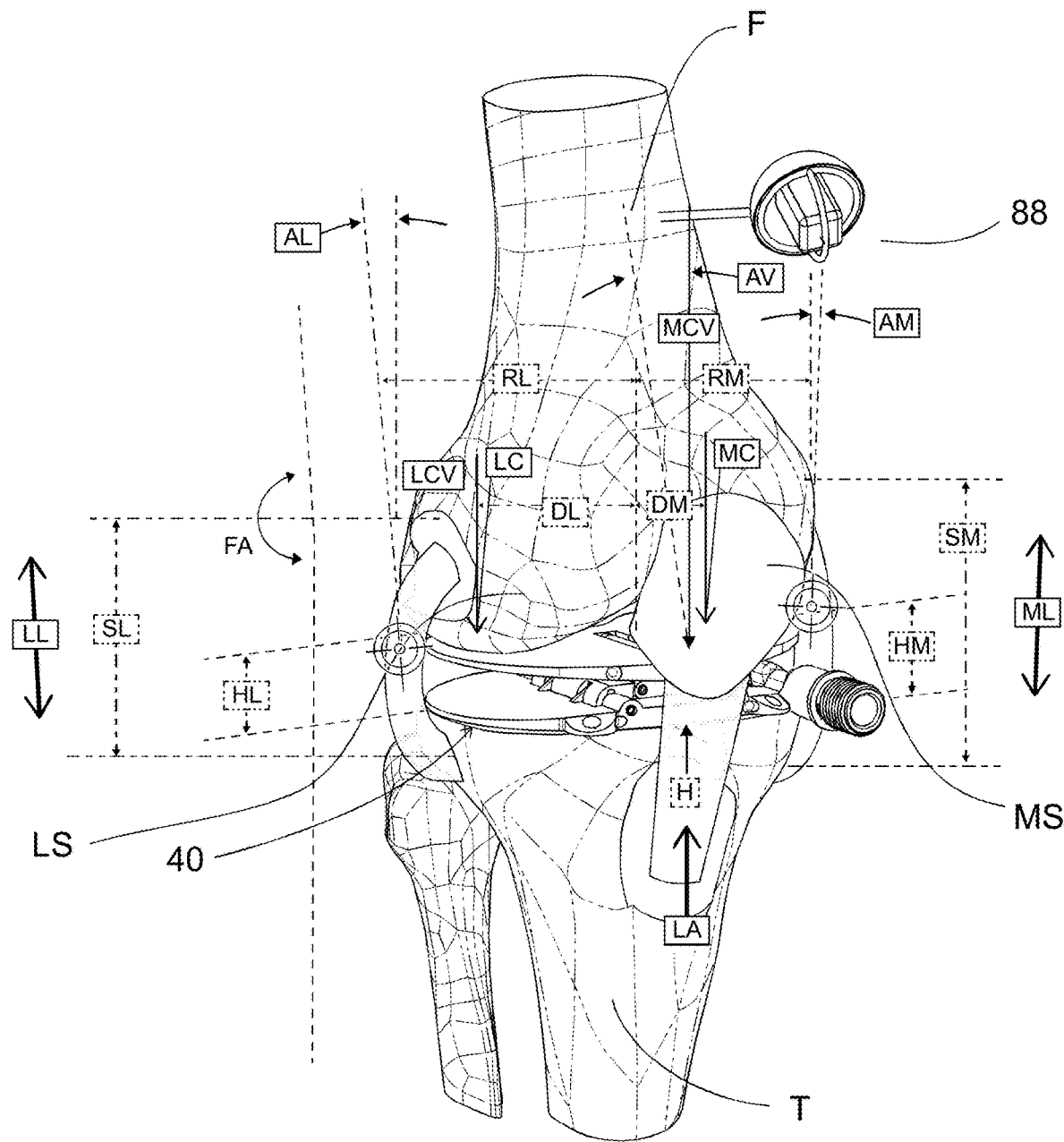
FIG. 38 is a perspective view of a knee joint J in an extended position, with a tensioner-balancer inserted therein.
Figure 39:
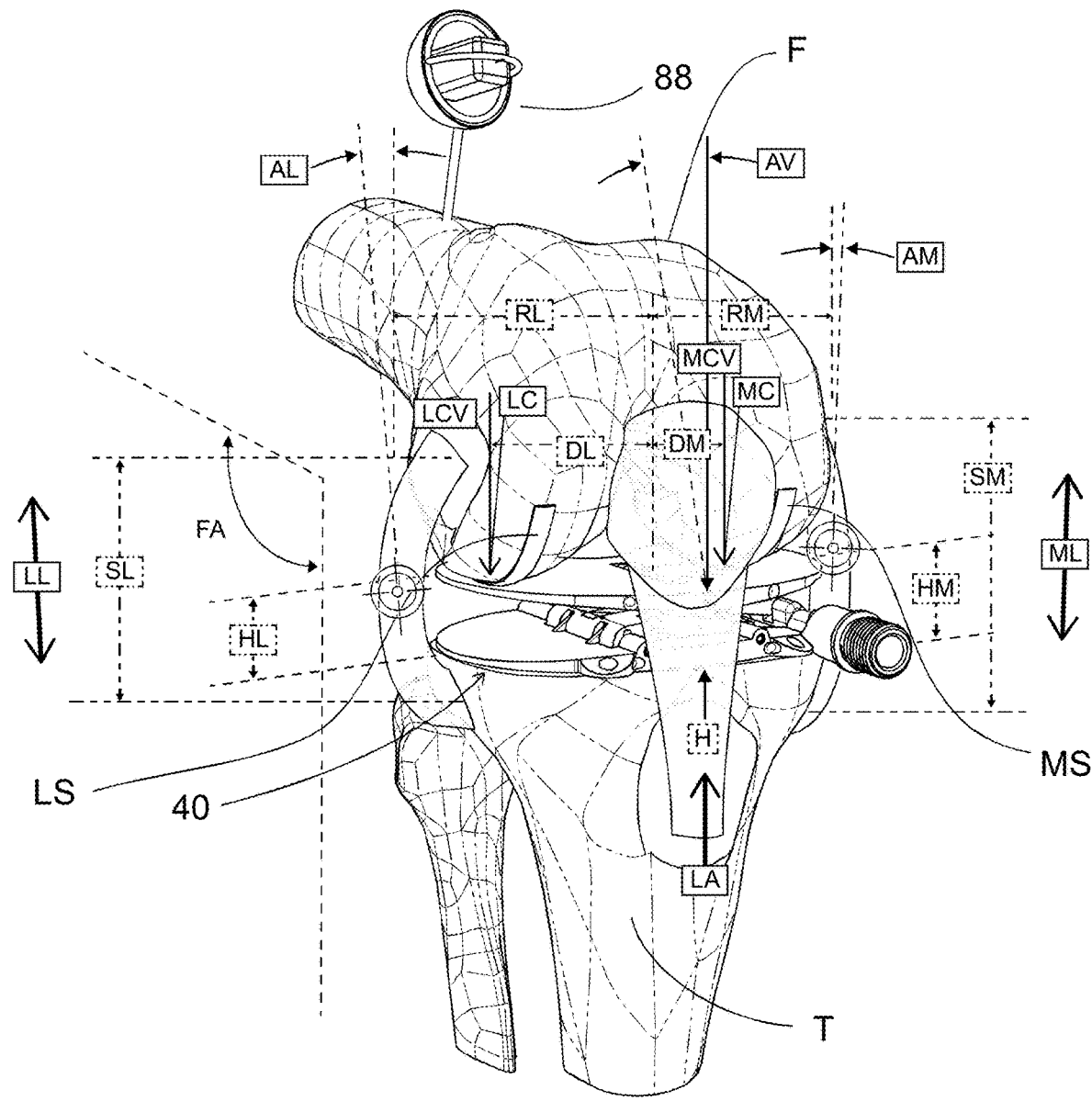
FIG. 39 is a perspective view of a knee joint in a flexed position, with a tensioner-balancer inserted therein.

The above-described ligament evaluation methods have focused on information detailed in a view orthogonal to the coronal plane. It is also possible to determine physical characteristics of the ligaments and their influence on knee kinematics in a view orthogonal to the sagittal plane. FIGS. 38 and 39 illustrate a knee joint J having a tensioner-balancer 40 as described above inserted therein. Given that the anterior-posterior location of condylar contact may be resolved as described above, the movement of ligaments in a view orthogonal to the sagittal plane may also resolved. Ligament angles as viewed orthogonal to the sagittal plane may be measured and used in addition to coronal plane measurements to compute ligament stress and load with the addition of a second trigonometric operation on the measured load values LC and MC.

It will be understood that the patellofemoral tendon and PCL (posterior cruciate ligament) may also play a role in the knee kinematics and may be accounted for in the ligament characterization model. For example, a portion of the distraction load applied may be realized as stress in the patellofemoral tendon or PCL. It is understood that this stress is dependent on flexion angle and may depend on flexion angle. In general, the patellofemoral tendon will have a greater influence on knee kinematics in flexion that it will in extension. Similarly, in general the PCL will have a greater influence in mid-flexion and deep flexion (e.g., beyond 90 degrees). These effects of the patella and related structures are inherently accounted for by the apparatus and method described herein, as the patella may be left in place during the evaluation and measurement procedure.

FIGS. 40 through 44 illustrate various aspects of the measurement and evaluation method.

Referring to FIG. 40, a joint J is illustrated along with charts showing the load-deformation characteristics of the medial and lateral soft-tissue complexes, juxtaposed with charts showing the stress-strain characteristics. It can be seen that the trend line of load versus elongation generally tracks the trend line of stress versus strain, and includes a region of generally constant linear slope, or close approximation thereof. In practice, the tensioner-balancer 40 is used to directly measure forces and loads on the joint J; stresses and strains can be computationally derived from these forces and loads, as noted above.

The apparatus and method described herein may be used to measure the actual load versus deflection curves of a patient's soft tissues, for example the curve shown at the top of FIG. 40. It is noted that "deformation" and "deflection" may be used as synonyms herein when describing the ligament complexes. In one procedure, the tensioner-balancer 40 may be inserted into a knee in a retracted position, the knee joint J may be positioned at a desired flexion angle, then the tensioner-balancer 40 may be extended and data collected. This procedure may be repeated in a variety of flexion angles. It is also possible to collect this data dynamically, e.g., by extending the tensioner-balancer to a predetermined load and then maintaining that load while moving the knee joint J through a range of flexion angles and collecting data. "Moving the knee joint" in this context refers to articulating the knee joint. This may be accomplished by producing relative motion of the femur bone and the tibia bone. This may include any combination of moving the femur while holding the tibia stationary, moving the tibia while holding the femur stationary, or moving both bones. It is noted that while moving through the range of motion, the tensioner-balancer can unload partially or completely the load on the ligament as the joint is moved to a different flexion angle, and then reloads the joint to obtain the loading characteristics. It is further possible to implement a "ramped" motion profile allowing for force/deformation curve characterization at a particular flexion angle. This can be achieved by actuating the tensioner-balancer 40 with a "pulsing" type of motion at a relatively low frequency, e.g. 5 to 10 Hertz—to allow for a full range of independent F/D curves to be developed. The pulsing motion can be repeated, medially and laterally, throughout a range of knee flexion angles—to precisely define and describe a knee through the full range of motion. The knee joint J may be distracted with the PCL intact.

FIG. 41 through 43 illustrate measured force versus deformation curves for the lateral soft tissue complex and medial soft tissue complex of the knee joint J.

FIG. 41 illustrates the joint J in full extension (0 degrees flexion), while FIG. 42 illustrates a joint at 45 degrees flexion, and FIG. 43 illustrates the joint at 90 degrees flexion. From the charts it can be seen that the force versus deformation curve is different in each flexion position of the joint J. It can also be seen that in each instance, the lateral side of the joint is less stiff (the curve has a lower slope) than the medial side of the joint J. This is a characteristic that is commonly observed in patients' knees, namely that the LCL exhibits greater deflection at a given load, i.e. it is more "lax". In mechanistic terms, this could also be described as having a lower effective spring rate.

Figure 44:
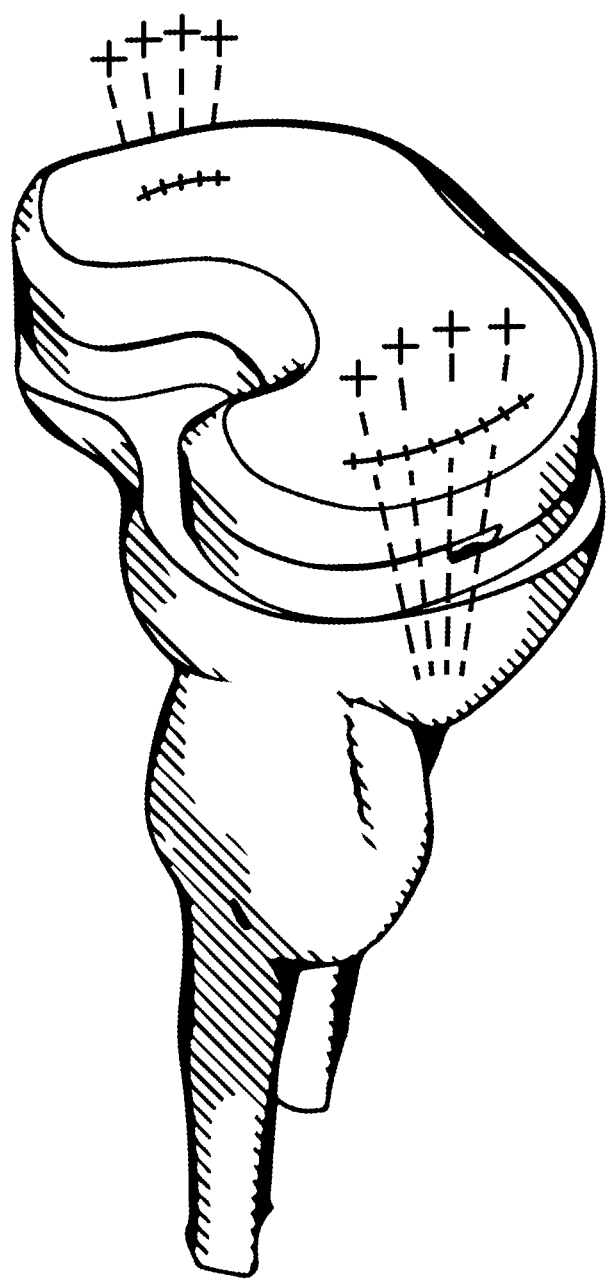
FIG. 44 is a perspective view of a tibia with an implanted prosthetic tibial component, illustrating the phenomena of medial pivot.

One important result of this asymmetric soft tissue characteristic is shown in FIG. 44. This shows the locus of contact points on the medial side MS and the lateral side LS of a tibial component 12 as the joint moves through extension to flexion. It can be seen that the locus of contact points on the medial side translates a relatively small amount while the locus of contact points on the lateral side translates a relatively larger amount. This results in a rotational motion of the tibia about an axis extending through the medial contact points; this phenomenon is referred to as "medial pivot". For best patient satisfaction, this medial pivot must be accounted for when constructing an arthroplasty. The apparatus and method described herein are highly suitable for measuring and accounting for the medial pivot.

The ligament stiffness data can show important characteristics of the knee joint J, especially when data is taken at flexion angles other than 0 degrees or 90 degrees, i.e. when data is taken at mid-flexion angles.

This information is helpful to a surgeon in determining the kind and magnitude of ligament augmentations, cutting plane adjustments, implant sizing, and so forth to account for a "design point" in operation of the Knee.

For example, it may be desired to provide a minimum predetermined degree of "tautness" for the knee joint J in all positions.

For example, in a knee joint exhibiting mid-flexion laxity, a desired minimum tautness would not be present at all flexion angles if the ligament stiffness data were used based on the extended or fully flexed positions. In this situation, a surgeon may elect to make surgical decisions based on the 45 degree flexed position data.

As a counter example, a knee joint can exhibit mid-flexion tautness. In this situation, a surgeon may elect to make surgical decisions based on the fully extended or fully flexed position data in order to avoid excessive tightness in the mid-flexion position.

One or more of the methods described herein may be incorporated into a complete surgical flow process. For purposes of explanation, the pre-operative knee joint J is assumed to have some wear, injury, or disease process and is referred to as a "pathological knee".

Initially, the surgeon will operatively measure the pathological knee by using the tensioner-balancer 40, tracking marker(s), and related apparatus described above and sweeping the knee through a range of motion while using the apparatus to collect data.

Based on the collected data, the software application builds a surgical plan. The surgical plan includes implant positioning and augmentation computation. Fundamentally, the surgical plan embodies an algorithm which takes as input the pre-existing conditions of the pathological knee, the desired end condition (i.e. the repaired knee), and computes one or more corrections necessary to achieve the desired end condition. Nonlimiting examples of required corrections are: implant size selection, implant contact surface/articular surface best curve fit, and soft tissue augmentations.

In modeling the soft tissue of a specific patient, an appropriate patient specific set of intraoperative and postoperative parameters for a plan of care may be developed. The parameters may be influenced or selected by populational and demographic data such as age, gender, stature, pathology, disease state, activity level, outcome goals, and lifestyle. The parameters described may include the total distraction load to be used for balancing the knee, patient-specific medial and lateral contact loads, patient-specific prosthesis geometry and sizing, flexion-angle-specific loads, ligament-specific loads, or position and tension applied to any implanted tensile members for ligament augmentation or reinforcement. In particular, the implant geometry will be imported into the digital geometric model of the knee joint as part of this process. Patient-specific parameters will also be influenced by a patient's individual anatomy and kinematics.

One important factor that has not been addressed systematically in the prior art is the desirability of constructing the arthroplasty such that the load applied to each ligament complex (medial and lateral) lies in a specific, desired portion of the force/deformation curve (or stress/strain curve) for that ligament complex. (For reference purposes, this curve may be referred to as a "characterization curve"). In many cases, the selected portion would be the linear portion of the characterization curve. This result may be achieved by proper selection of the type, size, shape, and position of the implant. These selections are facilitated by the apparatus and method described herein. It is also possible to construct the arthroplasty such that the load applied to each ligament complex lies in at a different selected characterization curve sub-portion or a different selected position on the characterization curve, for different selected flexion angles. For example, it could be configured to be more taut in the mid-flexion position and less taut in a flexed position.

Figure 45:
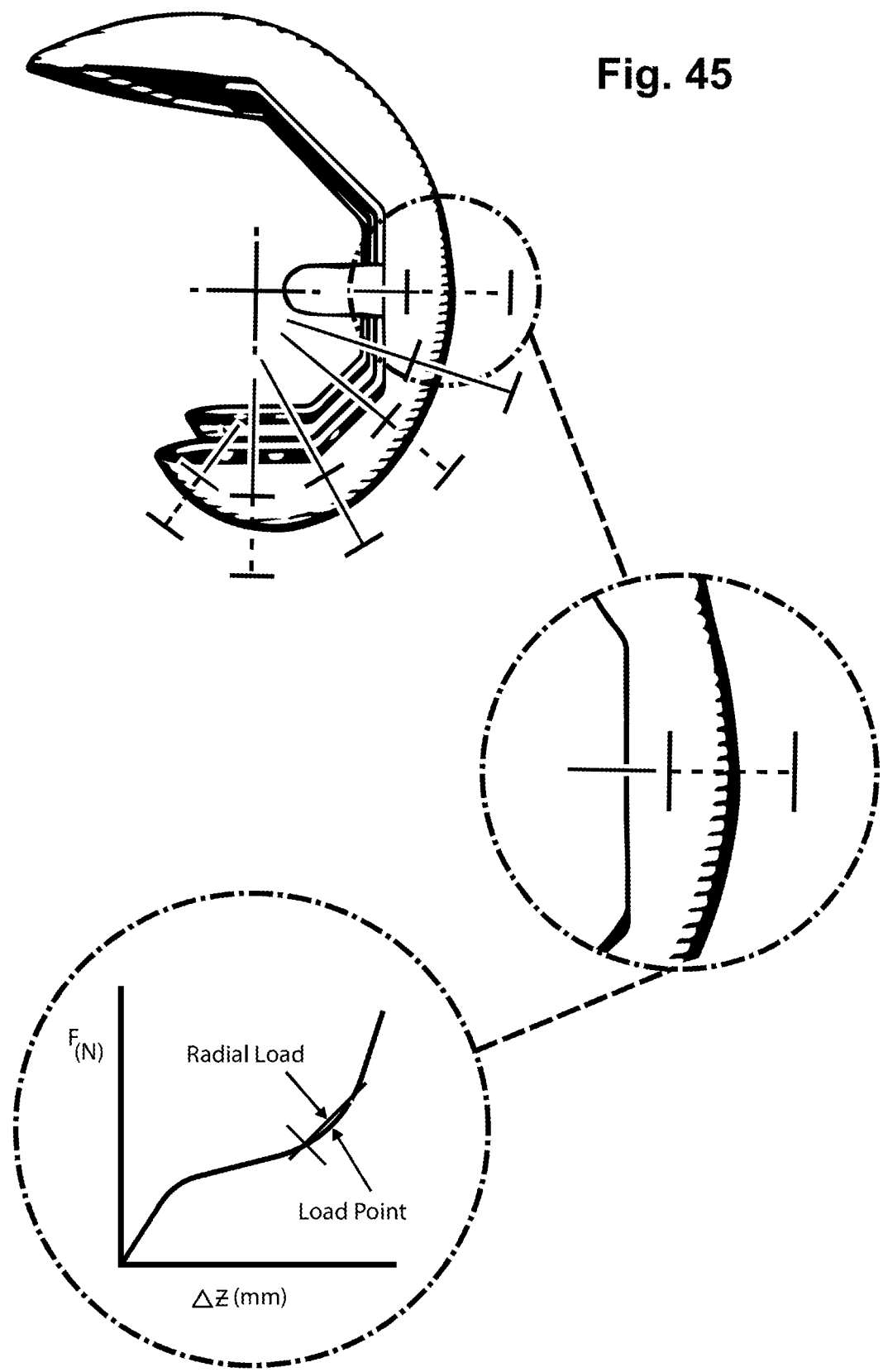
FIG. 45 is a diagram of a femoral component, showing the location of load measurements superimposed thereon.

FIG. 45 is a diagram illustrating the location of measurements relative to the flexion position of a femoral component 14 (and thus the knee as a whole). This example shows an example of a desired postoperative condition. Originating from a common center point, the radial lines indicate various flexion angles of the knee, for example 0 degrees, 30 degrees, 45 degrees, 60 degrees, 90 degrees, 120 degrees. The enlarged view shows the load measurement at the specific contact point along the articular surface in the given flexion angle. It will be understood that there are independent measurements of the medial side and lateral side; specific example shows the lateral side measurement. The example breakout view shows that the specific load measured lies within the lower and upper bounds of the linear portion of the load/deflection curve; i.e. in the desired zone or band for this specific example.

Ideally, the type, size, and position of the implant will result in the measured load lying within the desired range of the force/deflection curve, for example in the linear response zone, for both medial and lateral sides, over the entirety of the range of extension-flexion.

When such a result is achieved, the knee joint J can be expected to have a consistent behavior over the range of motion, without excessive tautness or laxity in certain positions.

The software application may employ a best-fit algorithm given existing knee and implant conditions to approximate this result as closely as possible. The output of the software application would generate the cutting planes (in the femur and/or the tibia) required to achieve this best-fit result. The digital geographic model may be updated with the computed cutting planes.

Using the information generated in the above-described process, a guided surgical workflow may be carried out. This could be using augmented reality, robotic guidance, or the like.

As part of a surgical procedure, one or more marking and guiding devices may be used to locate cutting planes and make cuts on the knee joint J.

Figure 46:
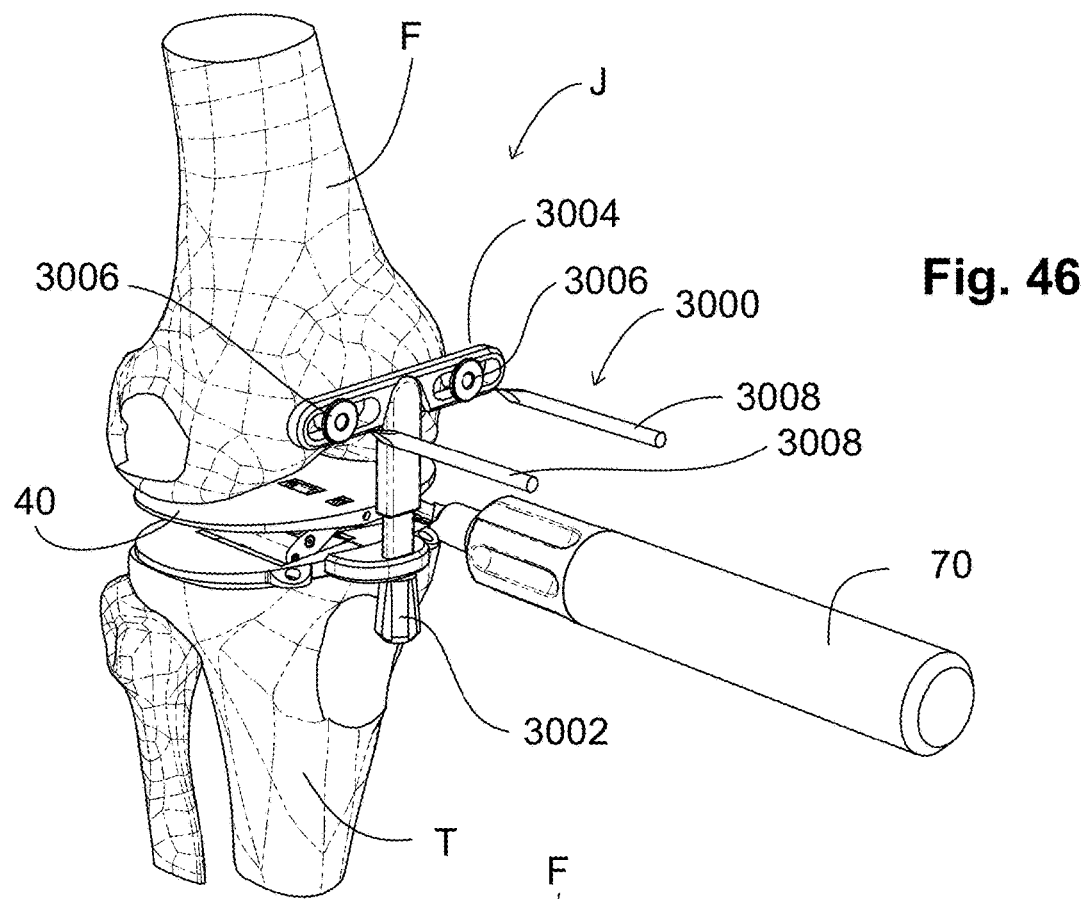
FIG. 46 is a perspective view of a knee joint in an extended position, with a tensioner-balancer inserted therein, and a marking guide attached to the tensioner-balancer.

FIG. 46 illustrates knee joint J with a tensioner-balancer 40 inserted therein and the instrument 70 coupled to the tensioner-balancer 40. Tensioner-balancer 40 is in the extended position and can be seen that a tibial plateau cut has already been made. A T-shaped marking guide 3000 has a shaft 3002 which is mounted to the tensioner-balancer 40 by an appropriate mechanical connection and a cross-beam 3004. The shaft 3002 is adjustable in a vertical direction V. The cross-beam 3004 carries a pair of spaced-apart guide bushings 3006. These are adjustable in a lateral direction L relative to the cross-beam 3004. The marking guide 3000 may be used by coupling it to the tensioner-balancer 40, adjusting in the vertical and lateral directions such that each of the guide bushings 3006 are at a desired location relative to the femur F, and then marking or spotting locations on the anterior aspect of the femur F. In the illustrated example, this may be carried out by using the guide bushings 3006 to guide drills 3008 to form holes in the femur F. These holes may subsequently receive guide pins used to mount a guide block (described below).

Figure 47:
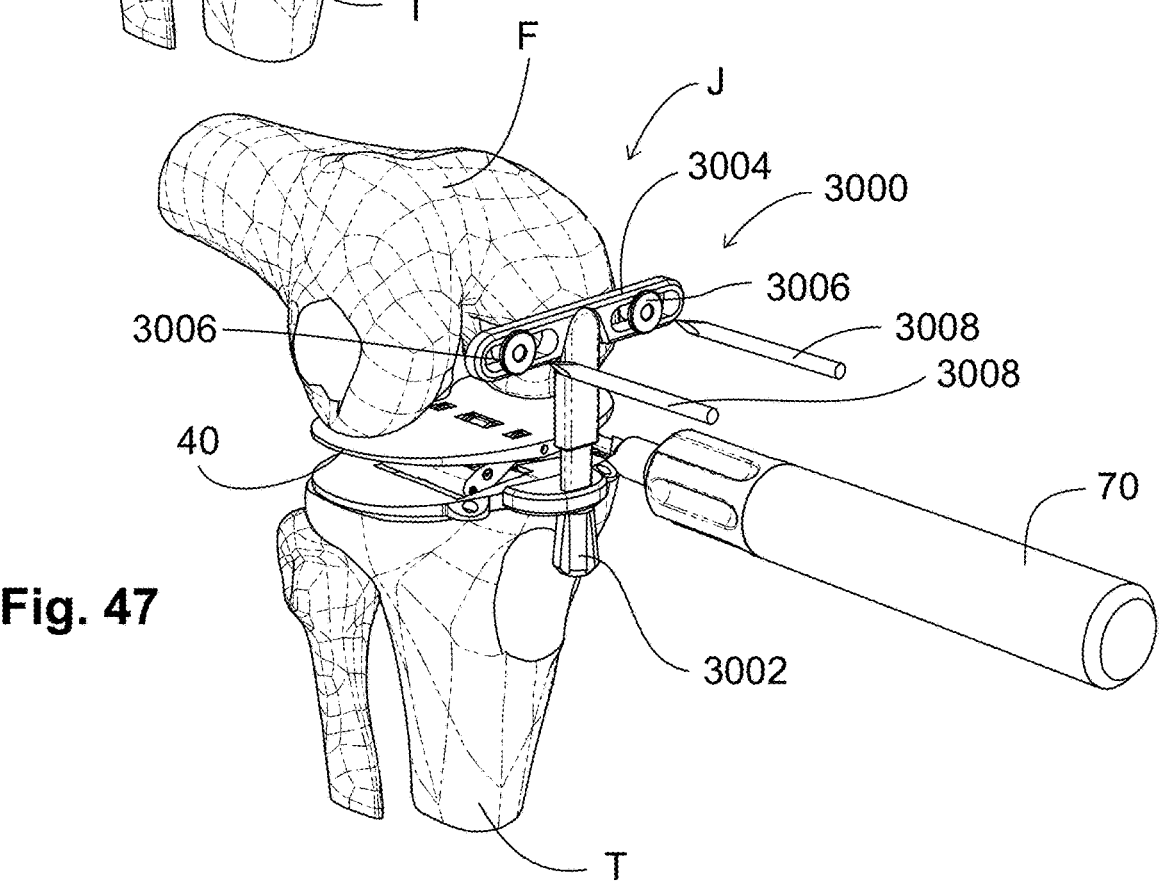
FIG. 47 is a perspective view of a knee joint in a flexed position, with a tensioner-balancer inserted therein, and a marking guide attached to the tensioner-balancer.

Similarly, as shown in FIG. 47, the adjustable marking guide 3000 may be used to mark guide holes in a distal aspect of the femur F. To do this, the marking guide 3000 would be used to described above, with the knee J in a flexed position.

Figure 48:
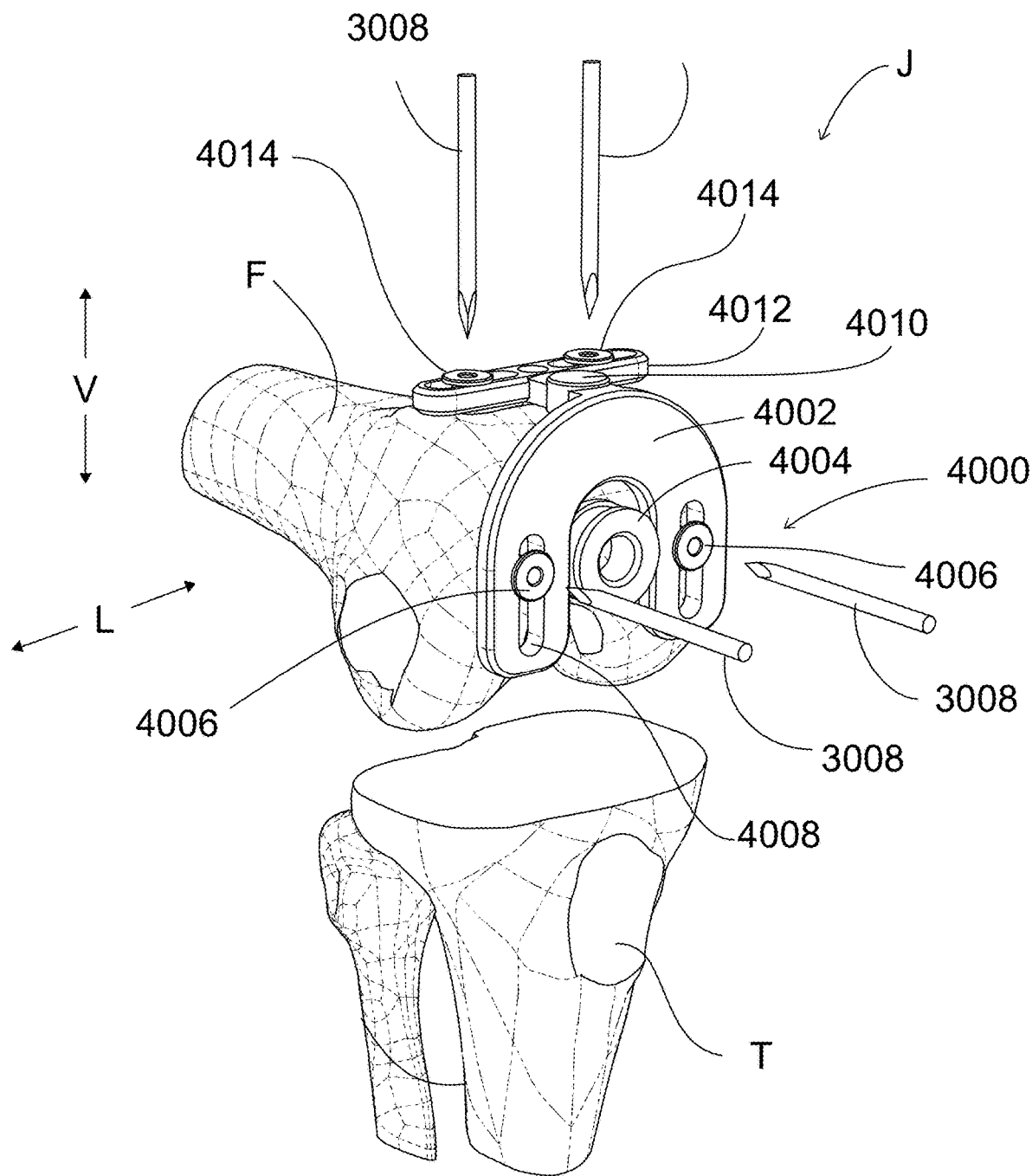
FIG. 48 is a perspective view of a knee joint in a flexed position, with a alternative marking guide attached thereto.

FIG. 48 illustrates an alternative marking guide 4000. This includes U-shaped baseplate 4002 with a central hub 4004. Each leg of the baseplate 4002 includes a guide bushing 4006 slidably adjustable in a slot 4008, in a vertical direction V. In adjustable shaft 4010 extends perpendicular to the plane of the baseplate 4002. A cross-beam 4012 extends from an end of the adjustable shaft 4010. The cross-beam 4012 carries a pair of spaced-apart guide bushings 4014. These are adjustable in a lateral direction L relative the cross beam 4012. The marking guide 4000 may be used by first coupling it to the femur F. For example, the central hub 4004 may be aligned with the trochlear groove of the femur F. Optionally, a locating instrument may be passed through the central hole of the central hub 4004, or if a medullary nail is present, it could be used to align the central hub 4004. The guide bushings 4006 would then be adjusted in the vertical direction such that each of the guide bushings 4006 is in a desired position relative to the posterior aspect of the femur F. The guide bushings 4014 would then be adjusted in axial and lateral directions such that each of the guide bushings 4014 are at a desired location relative to the anterior aspect of the femur F. Locations would then be marked or spotted on the anterior and distal aspects of the femur F. In the illustrated example, this may be carried out by using the guide bushings 4006 and 4014 to guide drills 3008 to form holes in the femur F. These holes may subsequently receive guide pins used to mount a guide block (described below).

Figure 49:
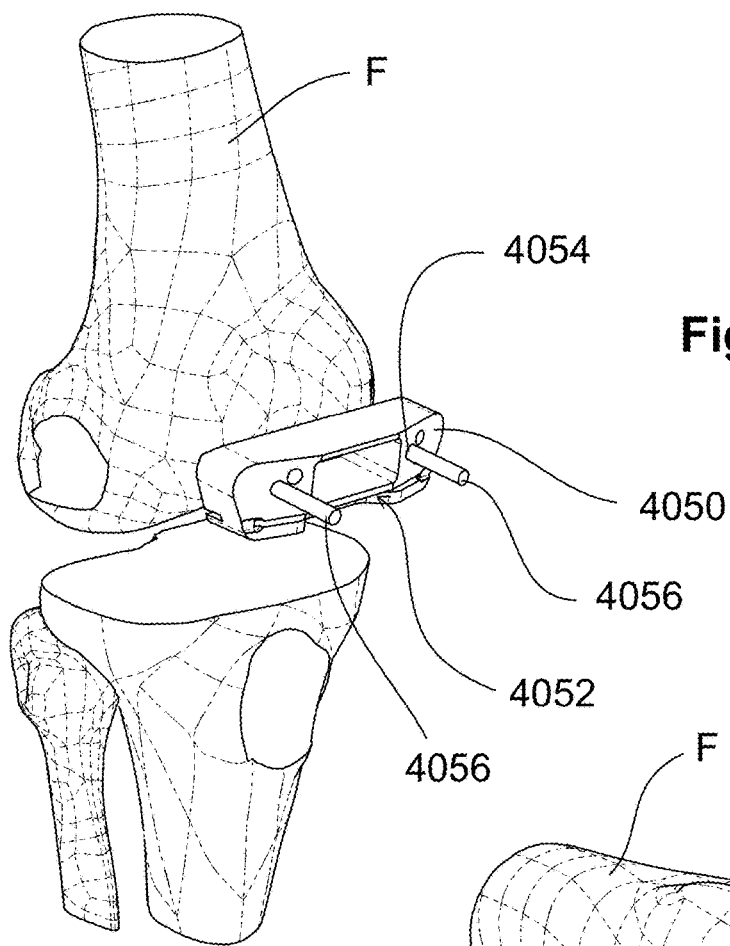
FIG. 49 is a perspective view of a knee joint in an extended position, with a guide block attached to and anterior aspect thereof.

Once the guide holes are spotted, they may be used to mount guide blocks for making cuts on the femur F. For example, FIG. 49 illustrates a guide block 4050 having a reference surface 4052 positioned and aligned to guide a distal femoral cut. The guide block 4050 has holes 4054 which receive guide pins 4056 that pass through the guide block 4050 and are received in guide holes formed as described above. When mounted to the femur F, the blade of a cutting tool (not shown) may be placed in contact with the reference surface 4052 and used to make a distal femoral cut.

Figure 50:
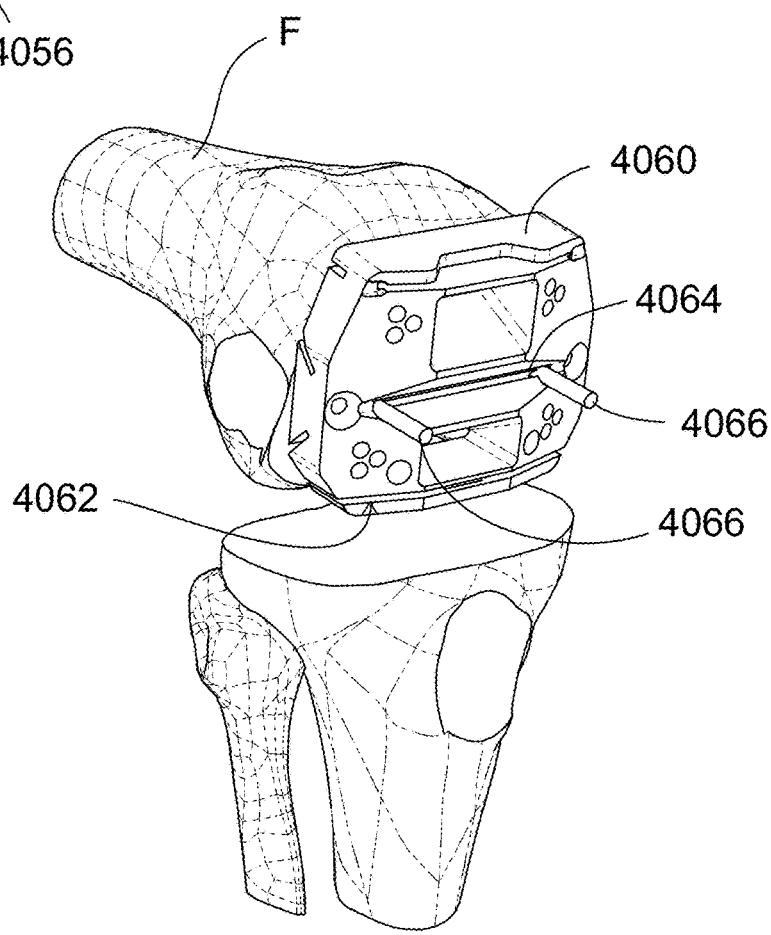
FIG. 50 is a perspective view of the knee joint in a flexed position, with a guide block attached to a distal aspect thereof.

As another example, FIG. 50 illustrates a guide block 4060 having a reference surface 4062 positioned and aligned to guide a posterior femoral cut. The guide block 4060 has holes 4064 which receive guide pins 4066 that pass through the guide 4060 and are received in guide holes formed as described above. When mounted to the femur F, the blade of a cutting tool (not shown) may be placed in contact with the reference surface 4062 and used to make a posterior femoral cut.

Figure 51:
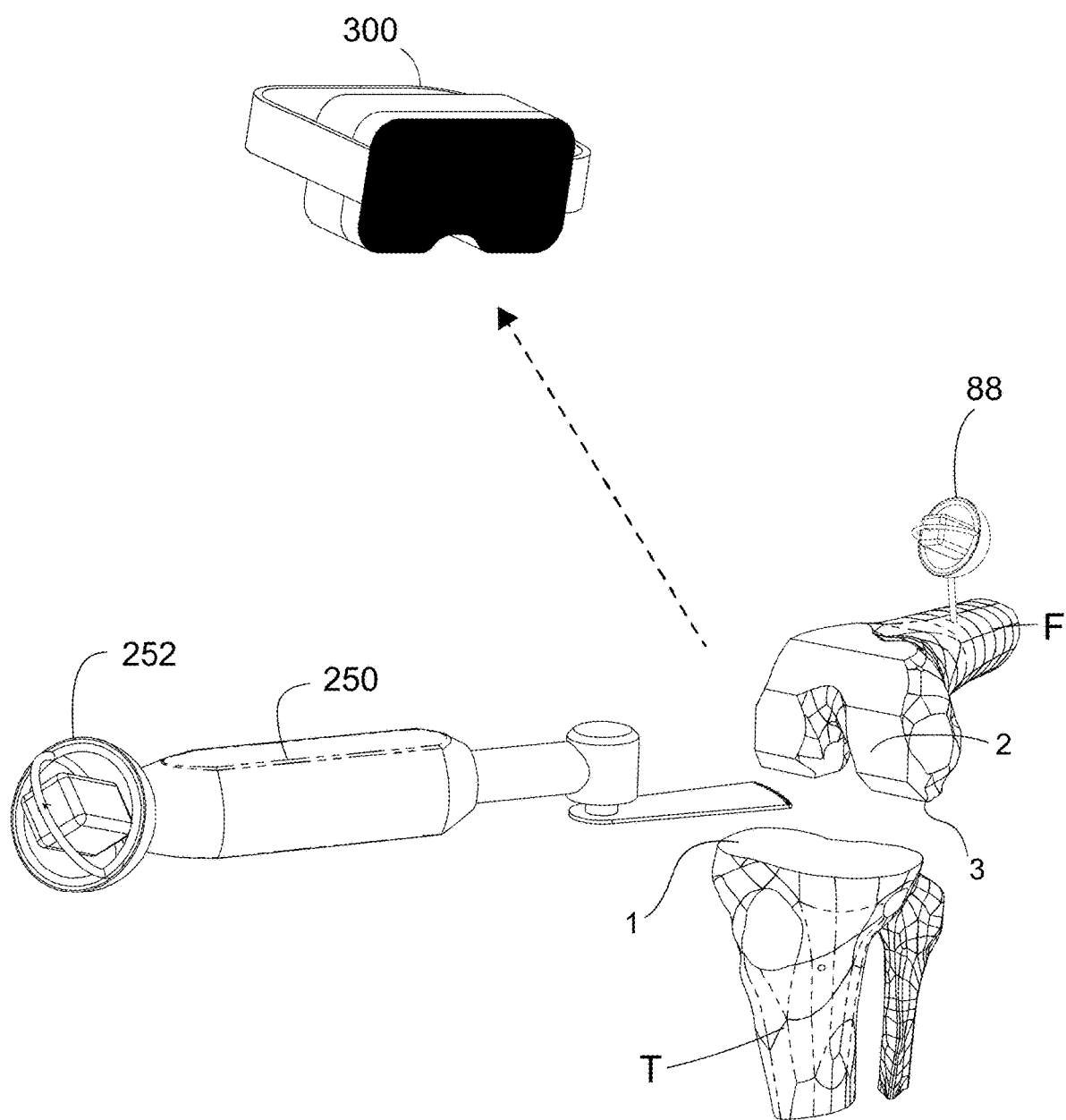
FIG. 51 is a perspective view of a human knee joint in conjunction with a mixed reality display device and an instrumented bone saw.

As an alternative to the guide blocks described above, information from the tensioner-balancer 40 and tracking markers may be used with hand-held equipment. Once the cutting planes are determined, the tracking markers 86, 88, or 90 may be used to guide a bone saw 250 equipped with a tracking marker 252 to make the distal femoral cut 2 at appropriate angle and location, as depicted in FIG. 51. In this context, the cutting plane (or a portion thereof) defines a computed tool path. This guidance is possible because intercommunication between the bone saw 250 and the associated tracking marker 252 will give the relative position and orientation of the bone saw 250 to that tracking marker. The cutting guidance may be provided in the form of information displayed on the remote display 84 described above. For this purpose, two-way data communications may be provided between and among the bone saw 250 (or other surgical instrument), the tracking markers 86, 88, or 90, and the remote display 84.

Figure 52:
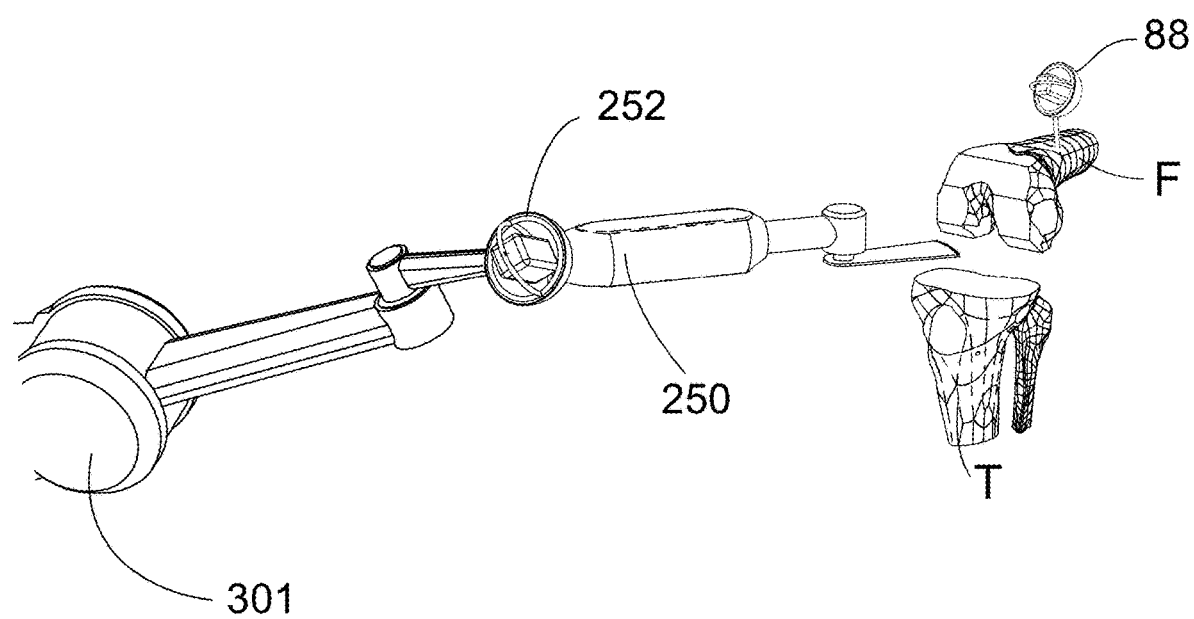
FIG. 52 is a perspective view of a human knee joint in conjunction with an instrumented bone saw coupled to a robot.

It should be noted that the bone saw 250 can be guided with reference to only a single tracking marker 88 coupled to the femur F. Alternatively, the cutting guidance (optionally along with other information, such as the virtual future position of the drilled holes and implants used) may be displayed on a body-worn display providing 2D or 3D graphics or providing a holographic heads-up display with an information panel (e.g., a Virtual Reality or augmented reality or mixed reality headset 300). Alternatively, the cutting guidance may be provided to a conventional robot 301 (FIG. 52) to which the bone saw is mounted.

Figure 53:
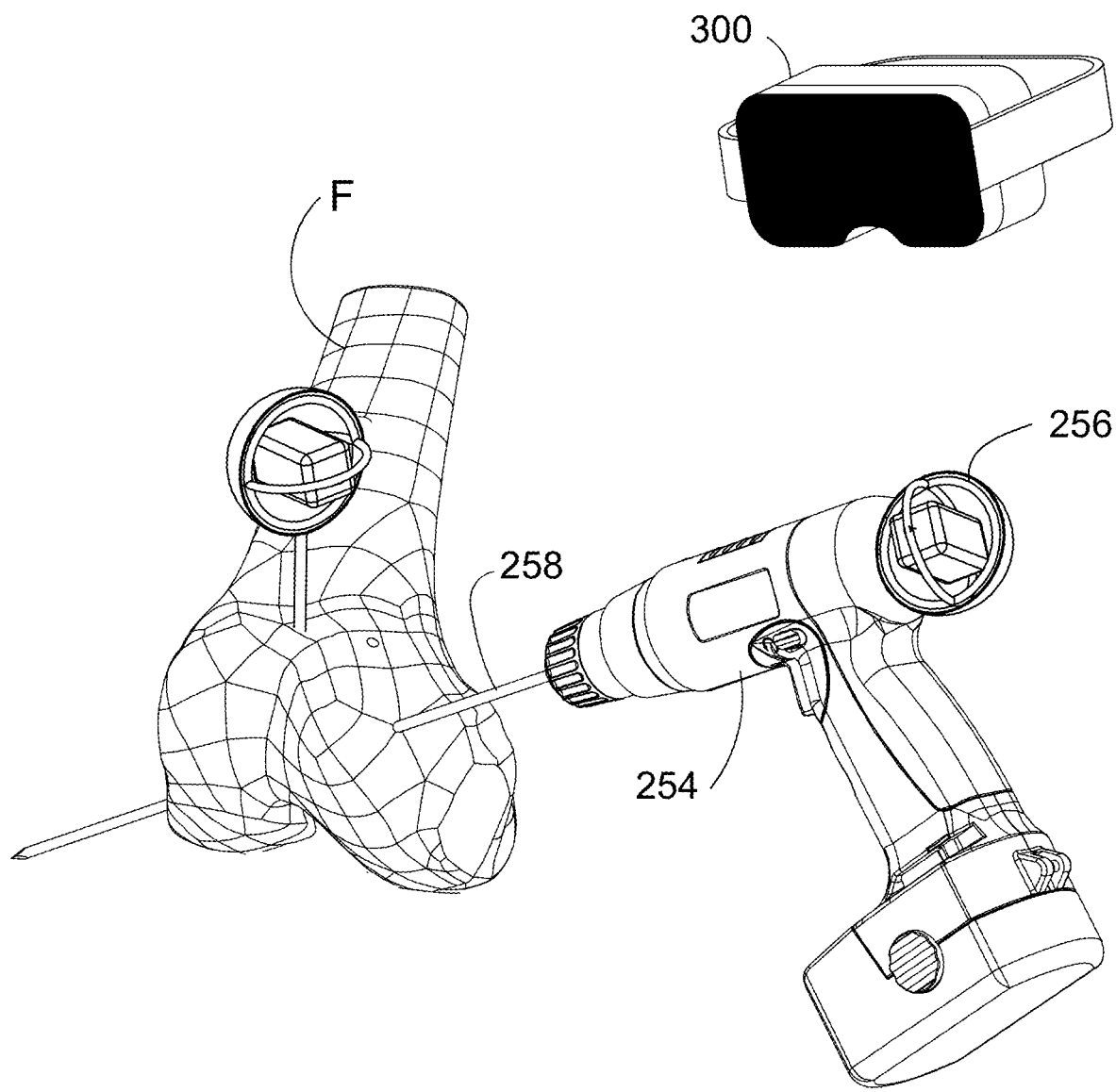
FIG. 53 is a perspective view of a human knee joint in conjunction with a mixed reality display device and an instrumented drill.
Figure 54:
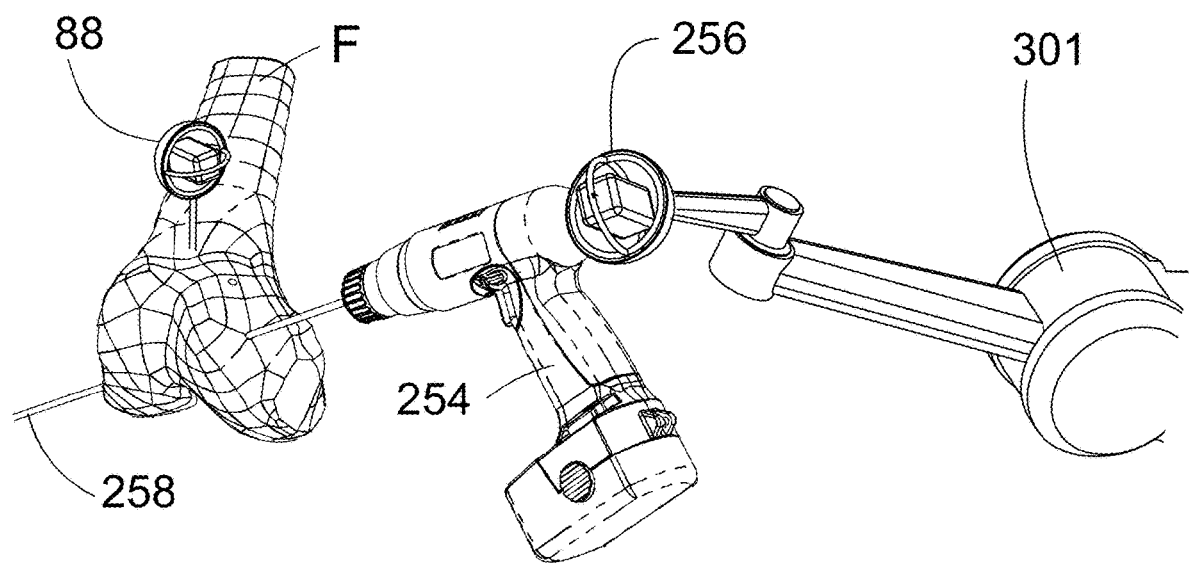
FIG. 54 is a perspective view of a human knee joint in conjunction with an instrumented drill coupled to a robot.

Information from the tensioner-balancer 40 and tracking markers may optionally be used for drilling holes, for example to anchor tensile elements. Referring to FIG. 53, once a position of a hole to be drilled is determined, the tracking markers 86, 88, or 90 may be used to guide a cordless drill 254 equipped with a tracking marker 256 to drill a hole, with the drill bit 258 extending an appropriate angle. In this context, the hole to be drilled (or a portion thereof) defines a computed tool path. Guidance along the tool path is possible because intercommunication between the cordless drill 254 and the tracking marker 256 will give the relative position and orientation of the cordless drill 254 to those markers. The drilling guidance may be provided in the form of information displayed on the remote display 84 described above. For this purpose, two-way data communications may be provided between and among the cordless drill 254 (or other surgical instrument), the tracking markers 86, 88, or 90, the actuating instrument 70, and the remote display 84. It should be noted that the drill 254 can be guided with reference to only a single tracking marker 88 coupled to the femur F. Alternatively, the drilling guidance (optionally along with other information, such as the virtual future position of the drilled holes and implants used) may be displayed on a body-worn display providing 2D or 3D graphics or providing a holographic heads-up display with an information panel (e.g., a Virtual Reality or augmented reality or mixed reality headset 300 or glasses or surgical protective screen. Alternatively, the drilling guidance may be provided to a conventional robot 301 (FIG. 54) to which the bone saw is mounted.

Figure 55:
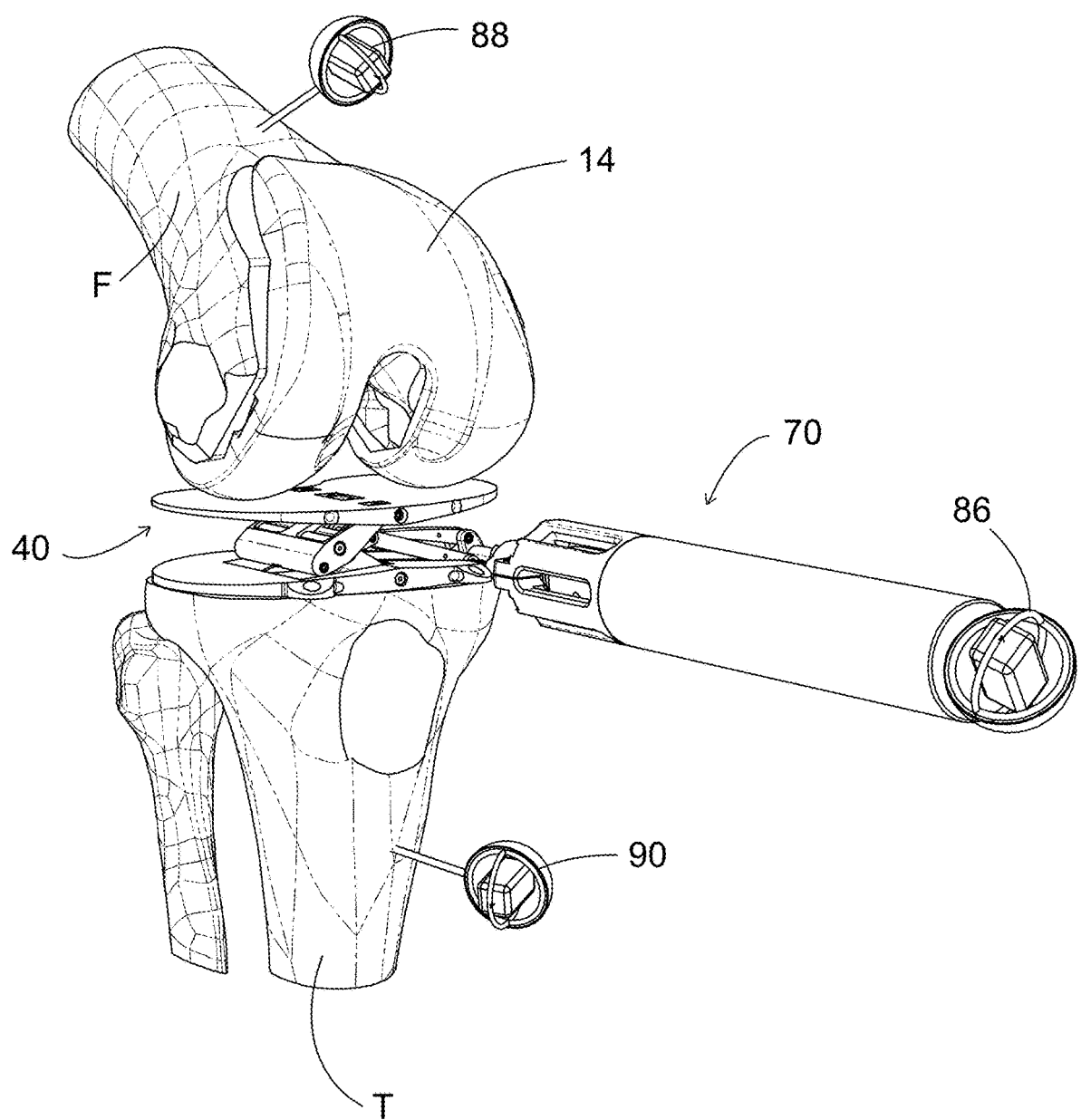
FIG. 55 is a perspective view of a human knee joint having a trial endoprosthesis device implanted, in conjunction with a tensioner-balancer.

As seen in FIG. 55, the tensioner-balancer 40 may be used with a trial implant (femoral component 14) to collect data and evaluate the femoral component 14.

In addition to retaining the patients' PCL in a knee arthroplasty, it may be augmented (reinforced) using one or more artificial tensile members. The term "tensile member" as used herein generally refers to any flexible element capable of transmitting a tensile force. Nonlimiting examples of known types of tensile members include sutures and orthopedic cables. Commercially-available tensile members intended to be implanted in the human body may have a diameter ranging from tens of microns in diameter to multiple millimeters in diameter. Commercially-available tensile members may be made from a variety of materials such as polymers or metal alloys. Nonlimiting examples of suitable materials include absorbable and resorbable polymers, nylon, ultrahigh molecular weight polyethylene ("UHMWPE") or polypropylene titanium alloys, or stainless steel alloys. Known physical configurations of tensile members include monofilament, braided, twisted, woven, and wrapped. Optionally, the tensile member may be made from a shape memory material, such as a temperature-responsive or moisture-response material.

Figure 56:
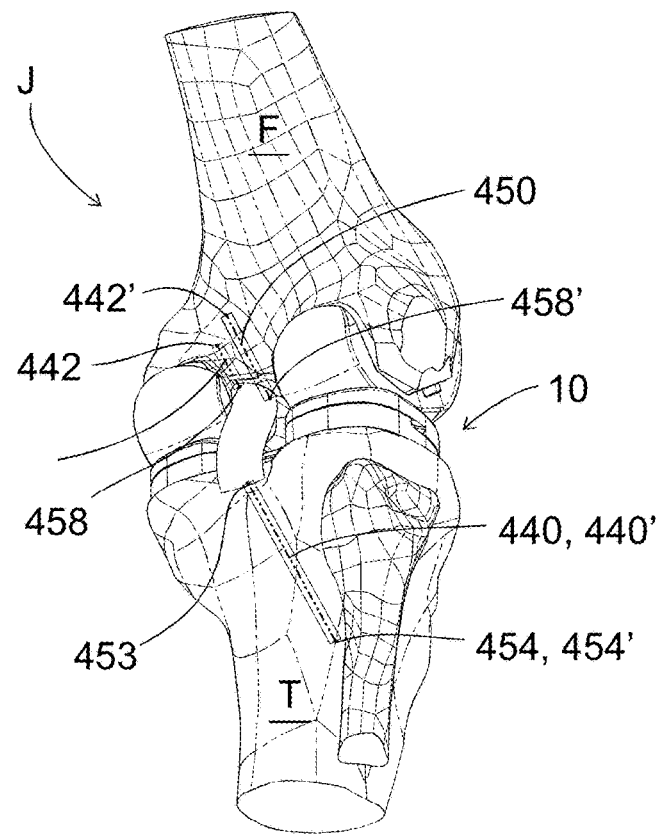
FIG. 56 is a perspective view of a posterior aspect of a human knee joint having a posterior cruciate ligament reinforced by artificial tensile member.
Figure 57:
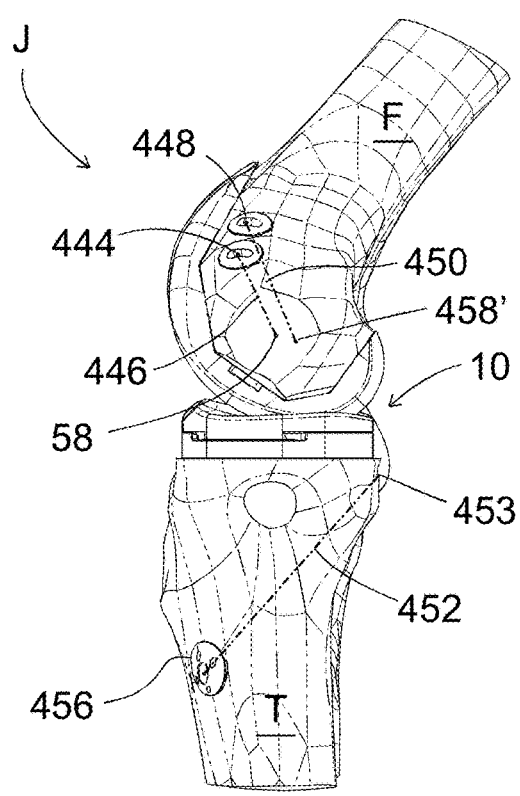
FIG. 57 is a view of the medial aspect of the human knee joint of FIG. 56.

FIGS. 56 and 57 illustrate a tensile member passing through transosseous passages formed in bone (e.g., by drilling), fixed by anchors, and routed across the posterior aspect of a human knee joint J. The tensile member replaces or augments or reinforces or tethers the PCL. A similar method can be used for MCL or LCL or other local ligament augmentation.

In the illustrated example, two tensile members are present, referred to as first and second tensile members 440, 440' respectively.

The first tensile member 440 has a first end 442 secured to the femur F on the outboard side thereof, by a first anchor 444. (With reference to this example, the terms "inboard" and "outboard" are used to describe locations relative to their distance from the meeting articular surfaces of the joint J. For example, the endoprosthetic 10 would be considered "inboard" of the joint J, while the anchor 444 would be considered "outboard"). The first tensile member 440 passes through a first femoral passage 446 formed in the femur F, exiting the inboard side of the femur F.

The second tensile member 440' has a first end 442' secured to the femur F on the outboard side thereof, by a second anchor 448. The second tensile member 440' passes through a second femoral passage 450 formed in the femur F, exiting the inboard side of the femur F.

The first and second tensile members 440, 440' span the gap between femur F and tibia T and enter a tibial passage 452 at an inboard side. The first and second tensile members 440, 440' pass through the tibial passage 452 at a single entry 453, exiting the outboard side of the tibia T. Second ends 454, 454' of the first and second tensile members 440, 442' are secured with a third anchor 456.

The term "anchor" as it relates to elements 444, 448, and 456 refers to any device which is effective to secure a tensile member passing therethrough. Nonlimiting examples of anchors include washers, buttons, flip-anchors, adjustable loop devices, fixed loop devices, interference screw devices, screw plates, ferrules, swages, or crimp anchors.

The tensile members 440, 440' can be routed through or along the PCL.

Figure 58:
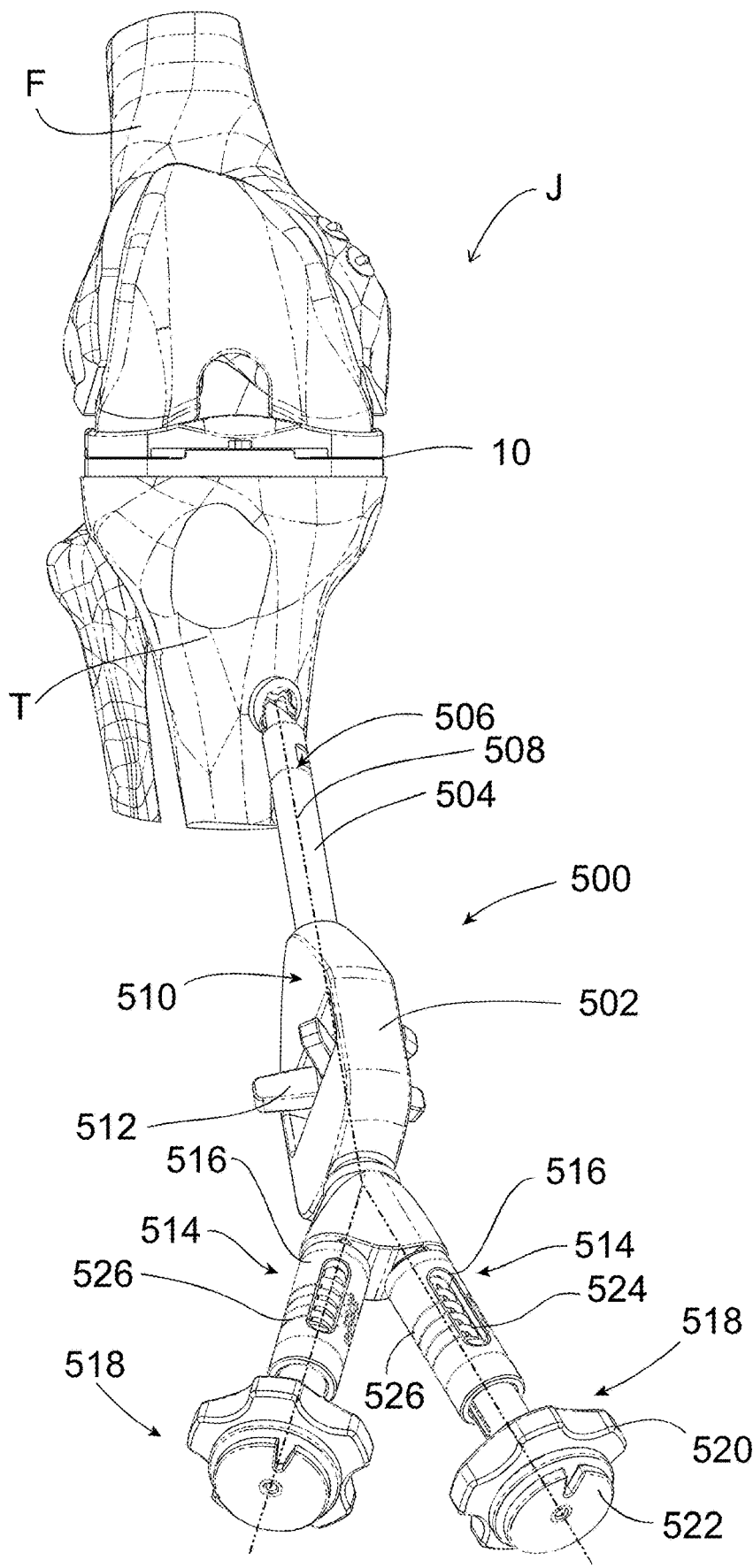
FIG. 58 is a view of the anterior aspect of the human knee joint in combination with an instrument for tensioning an artificial tensile member.

FIG. 58 illustrates an exemplary insertion instrument 500 which may be used to insert, tension, and activate swage-type anchors. The basic components of the insertion instrument 500 are a body 502, a stem 504 extending from the body 502 and having an anchor connection mechanism 506 disposed at a distal end thereof, a hollow pushrod 508 extending through the stem 504 and slidably movable between retracted and extended positions, and a driving mechanism 510 for moving the pushrod 508 between retracted and extended positions. The stem 504 and the pushrod 508 may be rigid or flexible.

In the illustrated example, the driving mechanism 510 comprises an internal threaded mechanism which is manually operated by a star wheel 512.

A tensioner 514 is part of or connected to the insertion instrument 500. It has a housing 516. A shuttle assembly 518 including an adjustment knob 520 and a grooved spool 522 is received inside the housing 516. A compression spring 524 is captured between the shuttle assembly 518 and the housing 516. The shuttle assembly 518 can translate forward and aft relative to the housing 516 in response to rotation of the adjustment knob 520.

In use, a first end of a tensile member 440 passes through the hollow interior of tensioner 514 and is secured to the spool 522. The tension applied to the tensile member 440 may be indicated, for example, by observing the position of the shuttle assembly 518 relative to a calibrated scale 526 on the housing 516. When a suitable final tension is achieved, the star wheel 512 may be operated to actuate the pushrod 508, swaging the tensile member 440 and fracturing the breakaway structure of the anchor. In the illustrated example, two separate tensioners 514 are provided, allowing the tension of each of the tensile members to be set independently.

In one example procedure where two tensile members are used, a first provisional tension is applied to the first tensile member and a second provisional tension is applied to the second tensile member. The second tensile member may have the same or different tension at the first tensile member. Next, the provisional tensions evaluated to determined if they are suitable. In response to the evaluation, they may be increased or decreased. Finally, the anchor may be swaged to secure the tensile members and finalize the tension. In one example, the tension may be from about 0 N (0 lb.) to about 220 N (50 lb.)

The methods and apparatus described herein have numerous advantages. They will permit the repair or reconstruction of the knee joint with good post-operative results without requiring unusual skill from the surgeon.

The foregoing has described a knee arthroplasty method. All of the features disclosed in this specification, and/or all of the steps of any method or process so disclosed, may be combined in any combination, except combinations where at least some of such features and/or steps are mutually exclusive.

Each feature disclosed in this specification may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends, or to any novel one, or any novel combination, of the steps of any method or process so disclosed.

What is claimed is:

1. A method of evaluating a human knee joint which includes a femur bone, a tibia bone, and ligaments, wherein the ligaments are under anatomical tension to connect the bones together, the method comprising:

inserting into the knee joint a tensioner-balancer that includes:
  a femoral interface surface and a tibial interface surface; and
  a means of applying a distraction force to the knee joint;
moving the knee joint through at least a portion of its range of motion;
while moving the knee joint, using the tensioner-balancer to maintain a predetermined distraction force or a predetermined distraction height, and collecting distraction height data and distraction force data of the femur bone relative to the tibia bone from at least one sensor;
deriving ligament displacement data and load data from the distraction height data and distraction force data of the femur bone relative to the tibia bone;
processing the collected data to produce a digital geometric model of the knee joint, wherein the model includes a ligament force versus ligament displacement characterization curve for each of a plurality of flexion angles of the femur bone relative to the tibia bone;
selecting a portion of the characterization curve that represents a specific level of ligament tautness desired;
importing into the digital geometric model an implant geometry having a femoral component and a tibial component, each of the components having an articular surface and an opposed back surface;
updating the digital geometric model by computing a location of a femoral bone cut and a tibial bone cut, the cuts being positioned such that when the components are placed in the joint with their articular surfaces in contact with each other and their back surfaces against the respective bone cuts, the implant will position the knee joint to function in the selected portion of the characterization curve; and
storing the digital geometric model for further use.

2. The method of claim 1, wherein the tensioner-balancer includes a sensor configured to measure at least one of the distraction force and a distraction height.

3. The method of claim 1, wherein the selected portion of the characterization curve is a linear range thereof.

4. The method of claim 1, wherein the cuts are positioned such that the implant will position the knee joint to function at different locations on the characterization curve, to produce different tautness levels when the knee joint is at different flexion angles.

5. The method of claim 1, wherein at least one of the ligament displacement data and the ligament load data includes independent medial and lateral information.

6. The method of claim 1, further comprising:
connecting at least one tracking marker to the knee joint;
collecting position data from the at least one tracking marker while moving the knee joint;
while moving the knee joint, using an electronic receiving device to collect the position data from the at least one tracking marker.

7. The method of claim 1, further comprising generating a graphical representation of at least one of the ligaments of the knee joint, the graphical representation including:
the ligament displacement along a range of flexion angles of the femur bone relative to the tibia bone; and
the ligament stress or force along a range of flexion angles of the femur bone relative to the tibia bone.

8. The method of claim 1, wherein the knee joint includes a patella bone and the patella bone remains in its native anatomical position during all steps of the method.

9. The method of claim 1, wherein the digital geometric model further includes:
a medial spline representing a locus of points of contact of a medial condyle of the femur with the femoral interface surface, over a range of knee flexion angles; and
a lateral spline representing the locus of points of contact of the femur with the femoral interface surface over a range of knee flexion angles.

10. The method of claim 1, further comprising using the tensioner-balancer to distract the knee joint with a PCL of the knee joint intact.

11. The method of claim 1, further comprising performing a tibial plateau cut before inserting the tensioner-balancer into the knee joint.

12. The method of claim 1, further comprising using a marking guide to indicate positions on the femur bone to make one or more cuts on the femur bone.

13. The method of claim 12, wherein the marking guide is connected to the tensioner-balancer.

14. The method of claim 1, wherein the tensioner-balancer includes:
a baseplate;
a top plate; and
a linkage interconnecting the baseplate and the top plate and operable to move the gap tensioner between retracted and extended positions, wherein the top plate is pivotally connected to the linkage so as to be able to freely pivot about a pivot axis.

15. The method of claim 14, wherein the femoral interface surface is defined by the top plate, the top plate including a lateral cantilevered pad and a medial cantilevered pad, wherein each cantilevered pad is provided with one or more strain gages at the intersection between the respective cantilevered pad and a stationary portion of the top plate.

16. The method of claim 1, wherein the gap balancer includes one or more individual devices, each of the one or more individual devices placed within a single compartment of the knee joint.

17. The method of claim 1, further including:
defining a primary datum oriented and fixed in six degrees of freedom;
defining at least one secondary datum, each secondary datum having fixed origins relative to the primary datum;
associating continuous position and orientation of the at least one secondary datum with respect to the primary datum;
while moving the knee joint, using a measuring apparatus to collect data describing position and movement in six degrees of freedom of the at least one secondary datum relative to the primary datum;
incorporating the measuring apparatus data into the digital geometric model.

18. The method of claim 17, wherein the measuring apparatus includes one or more tracking devices.

19. The method of claim 17, wherein the primary datum is referenced relative to the femur bone before any cuts or resections have been made.

20. The method of claim 17, wherein a difference is computed between a geometric position data collected from the measuring apparatus and a final defined desired set of geometric position data.

21. The method of claim 20, wherein the computed difference is used to compute the desirable final best-fit position of an endoprosthesis with known geometry.

22. The method of claim 17, wherein the primary datum is positioned outside the knee joint, and each of the femur and tibia bones has a secondary datum associated therewith.

23. The method of claim 17, wherein the primary datum is fixed relative to one of the femur and tibia bones.

24. The method of claim 17, wherein a desirable best-fit position of an endoprosthesis is based on procedural outcomes from population data collected over time.

25. The method of claim 17, wherein an endoprosthesis is positioned relative to the bones of the knee joint from pre-operative measurement to assess joint kinematics.

26. The method of claim 17, wherein the digital geometric model is used to develop a patient-specific operative procedure.

27. The method of claim 17, wherein the digital geometric model is used to develop a patient-specific endoprosthesis.

28. The method of claim 17, wherein the digital geometric model is used to develop a patient-specific augmentation or replacement or repair, of a ligament or a tendon.

29. The method of claim 17, wherein a digital display is used to portray the evaluated joint.

30. The method of claim 17, wherein the primary datum is established by physically registering landmarks on at least one of the tensioner-balancer, the femur bone, and the tibia bone.

\* \* \* \* \*